United States Patent
Nelson et al.

(10) Patent No.: US 6,750,453 B1
(45) Date of Patent: Jun. 15, 2004

(54) METHODS OF AND APPARATUS FOR DETECTING LOW CONCENTRATIONS OF TARGET GASES IN THE FREE ATMOSPHERE

(75) Inventors: Loren D. Nelson, Evergreen, CO (US); Martin J. O'Brien, Pine, CO (US)

(73) Assignee: Ophir Corporation, Littleton, CO (US)

(*) Notice: Subject to any disclaimer, the term of this patent is extended or adjusted under 35 U.S.C. 154(b) by 134 days.

(21) Appl. No.: 10/155,770

(22) Filed: May 25, 2002

(51) Int. Cl.[7] .............................................. G01N 21/17
(52) U.S. Cl. ................................. 250/338.5; 250/458.1
(58) Field of Search .......................... 250/458.1, 459.1, 250/461.1, 338.1, 338.5, 339.01, 339.06, 339.07, 341.1

(56) References Cited

U.S. PATENT DOCUMENTS

| | | | |
|---|---|---|---|
| 4,394,575 A | 7/1983 | Nelson | 250/343 |
| 4,489,239 A | 12/1984 | Grant et al. | 250/339 |
| 4,507,558 A | 3/1985 | Bonne | 250/345 |
| 4,873,481 A | 10/1989 | Nelson et al. | 324/58.5 R |
| 4,874,572 A | 10/1989 | Nelson et al. | 376/256 |
| 4,958,076 A | 9/1990 | Bonne et al. | 250/343 |
| 5,583,877 A | 12/1996 | MacPherson et al. | 372/4 |
| 5,606,804 A | 3/1997 | Smith et al. | 34/261 |
| 5,696,778 A | 12/1997 | MacPherson | 372/4 |
| 5,748,325 A | 5/1998 | Tulip | 356/437 |
| 5,889,198 A | 3/1999 | Reitmeier et al. | 73/25.05 |
| 5,946,095 A | 8/1999 | Henningsen et al. | 356/346 |
| 6,008,928 A | * 12/1999 | Sachse et al. | 359/246 |
| 6,121,627 A | 9/2000 | Tulip | 250/559.4 |

OTHER PUBLICATIONS

Fried et al., "Intercomparison of Tunable Diode Laser and Gas Filter Correlation, Measurements of Ambient Carbon Monoxide", Sep. 27, 2001, pp. 2277–2284, Atmospheric Environment, F–283, vol. No. V25(A) #10, 1991, Great Britain.

Herget et al., "Infrared gas–filter correlation instrument for in situ measurement of gaseous pollutant concentrations", pp. 1222–1228, May 1976, Applied Optics, vol. 15, No. 5.

Sandsten et al., "Gas imaging by infrared gas–correlation spectrometry", pp. 1945–1947, Dec. 1, 1996, Optics Letters, vol. 21, No. 23, Optics Letters.

* cited by examiner

Primary Examiner—Constantine Hannaher
Assistant Examiner—Timothy Moran
(74) Attorney, Agent, or Firm—Martine & Penilla, LLP

(57) ABSTRACT

A source directs broadband modulated light into a region the free atmosphere in which target gas may be present. A gas correlation radiometer responds to light transmitted through the region. Separate radiometer channels respond to a single beam of light after transmission through the region. A beam splitter separates the beam into two beams, one directed into each of the channels. The two channels separately and simultaneously respond to a respective one of the light beams for separately and simultaneously generating signals that together indicate whether the target gas is in the free atmosphere. A method provides an optimal bandpass of an IR filter that filters the light before transmission to the radiometers. Another method uses a null factor in computing an output that determines the concentration of the target gas in the free atmosphere. Long distance detection embodiments may be borne by vehicles such as trucks or aircraft.

63 Claims, 23 Drawing Sheets

METHODS OF AND APPARATUS FOR DETECTING LOW CONCENTRATIONS OF TARGET GASES IN THE FREE ATMOSPHERE

BACKGROUND OF THE INVENTION

1. Field of the Invention

The present invention relates generally to detecting gases, and more particularly to methods of and apparatus for detecting trace amounts of target gases, such as natural gas, remotely along long-range paths in the free atmosphere, wherein the exemplary natural gas detection is enabled by simultaneously remotely detecting methane and ethane along the same long-range path in the free atmosphere.

2. Description of the Related Art

In the field of gas detection, attempts are made to detect one specific, or "target", gas even though local conditions render such detection difficult. Such difficulty may be based, for example, on the fact that the target gas may only be present in "trace amounts", such as one or a few parts per billion (PPB). Moreover, the target gas may be mixed with, or present with, water vapor and/or undesired (non-target) background, or "competitive", gases that may be in the same atmosphere as contains the target gas, for example. The background gases are referred to as "competitive" gases because there are overlaps in absorption spectra of the trace gases and the background gases, e.g., in the infrared absorption spectra of such gases.

Many industries require facilities to detect target gases, such that there is a general need for accurate, fast and cost-competitive detection of target gases. However, the natural gas pipeline distribution system is the largest chemical distribution system in the United States. As a result, although equipment for detecting target gases other than natural gas has wide application in the United States, for example, the natural gas pipeline industry has the greatest need for accurate, fast, and cost-competitive chemical leak detection equipment and methods. This need relates in part to regulations that require gas utilities to perform periodic surveys for natural gas leaks.

Initially, in target gas detection for the natural gas industry, there is a need to distinguish between natural gas as a target gas, and other combustible gases. The main constituents of natural gas are methane and ethane, with methane being the primary component. However, methane is produced by many natural biological sources, including animal and plant. Thus, if an elevated methane level is sensed, it does not necessarily mean that there is a natural gas leak. In contrast, there are no substantial natural ethane emission sources. However, ethane generally does not exceed twenty-percent of natural gas. As a result, ethane is both more difficult to detect, but is a better indicator of natural gas than methane. Thus, to have an optimal natural gas detector, there is a need for the detector to simultaneously detect both methane and ethane to assure that the detected gas is from a natural gas leak and not from a natural emission source.

This need to simultaneously and independently detect both ethane and methane is not met by current gas detection equipment. For example, flame ionization detectors (FID) cannot distinguish natural gas from such competitive gases. As a result, when currently available FID equipment is used in an attempt to detect natural gas, the FID equipment provides "false natural gas alarms" based on the detection of leaking propane tanks, leaking gasoline cans, so-called "sewer gas", and all other combustible gases. A natural gas pipeline utility using the FID equipment must respond to each false natural gas alarm although there is in fact no natural gas leak. Another limitation of the FID equipment is that during the detection process, it is generally necessary to place the equipment very close to the ground and within a "cloud" of the target gas that is to be detected. As a result, the FID detection process is relatively slow, and FID equipment cannot be used at a place remote from the locale of the gas leak, for example.

Also, Fourier Transform Infrared (FT-IR) spectroradiometers use an interferometer to determine the spectral content of light passing through the free atmosphere. However, the output of such FT-IR instruments is based on a combination of all of the gases that are optically "active" (e.g., infrared absorptive). within the spectral region of the instrument. Thus, their temporal response is generally poor. Moreover, FT-IR systems are expensive, have very limited detection range through the free atmosphere, and cannot detect very low concentrations of target gases.

Further, in contrast to the FID and FT-IR techniques, tunable diode laser absorption Spectroscopy (TDLAS), laser absorption spectroscopy (LAS), and differential absorption laser-based radar (DIAL) all use laser emission sources that are narrow band. For example, the DIAL devices typically monitor only one or two very narrow spectral absorption lines. Laser-based techniques are more costly to manufacture, maintain and use compared to broadband techniques such as gas correlation radiometry (GCR). However, gas correlation radiometry (GCR) is generally a passive technique that relies on solar illumination or scattering, or on thermal emission background. Thus, GCR instruments do not have an active source of energy that is directed through the free atmosphere to the instrument. Further, while GCR instruments may be provided with filters that improve a signal to noise ratio by generally limiting the overall bandwidth of light admitted to a detector of the GCR instrument, such filters do not provide an optimized bandwidth around an optimized central bandpass wavelength. As a result, the sensitivity of such GCR instruments may be as low as 10 to 100 parts per million (PPM).

Moreover, the FT-IR, TDLAS, LAS, DIAL and GCR technologies provide separate background gas and target gas channels that are interrogated sequentially. That is, light transmitted along a path through the free atmosphere and then through the background channel may be detected by a detector first. After such detection, the light transmitted through the same path through the free atmosphere and then through the target gas channel is detected by the same detector. The resulting temporal, or sequential, spacing of the alternating detection of the background channel and the target gas channel may vary from 0.1 second to several minutes. That is, it generally takes more than 0.1 seconds for these systems to provide a complete data set consisting of a target gas absorption measurement and an atmospheric background measurement, and during that lime period, there may be changes in the atmospheric conditions along the path of the light. Thus, the light that is transmitted along the path and through the target gas channel may have been subjected to different atmospheric conditions along the light path (e.g., atmospheric turbulence and variability) than the light transmitted through the background channel. As a result, the accuracy of these instruments is subject to a sensitivity limitation when used in a dynamic atmosphere. Atmospheric turbulence and variability generally limit the ultimate sensitivity of these instruments in that the same value of instrument output provided at different times may not be based on the same amount of the target gas. Further, attempts to avoid such atmospheric-induced inaccuracies, e.g., attempts to distinguish between signals generated based on a target gas and on the varying atmospheric conditions, have generally been limited to situations in which light is transmitted only a few feet through a detection path that may contain the target gas to be detected. For example, it may be practical to provide known modulation imposed on light transmitted along a detection path that is only a few feet long from transmitter to detector. Given the few feet between the transmitter and the detector, a conductor may easily input the characteristics of the know modulation to the detector so that demodulation will be accurate. However, problems are faced in accurately demodulating the modulated light when the detection path must, for practical purposes, be hundreds or thousands of feet long.

In addition to the accuracy limitation due to limited sensitivity of these prior instruments that interrogate the separate background gas and trace gas channels sequentially, such instruments have limitations when attempts are made to use the instrument on a mobile platform, such as a truck or airborne vehicle. For example, by the very motion of the mobile platform, there is a dynamic, or different, atmosphere through which the light is transmitted. As a result, the problems of atmospheric turbulence and variability limit the ultimate sensitivity of the instrument used on this type of platform. Remote sensing systems mounted on moving platforms have the additional problem of variable surface reflectivity. Prior remote sensing instruments mounted on mobile platforms suffered additional sensitivity limitations due to the temporally sequential manner of monitoring separate background and trace gas channels.

Some have attempted to avoid these and other limitations of atmospheric turbulence and variability by isolating samples of the target gas in a closed chamber that is controlled to avoid turbulence and variability. However, the need to capture such samples from a possible location of a gas leak, and other time factors, render the local sampling of the target gas impractical for detecting trace amounts of target gases such as natural gas along miles and miles of pipeline, for example.

Another problem faced in detecting target gases is isolation of a signal representing the target gas from other signals caused by background emissions. For example, although some types of gas detectors modulate the light just before the light impinges on a light receiver to remove thermal emission due to a warm instrument housing, such modulation at the receiver does not remove other background emissions such as atmospheric turbulence, jitter, beam wander, changes in the index of refraction, or the constant thermal emission of the atmosphere and the Earth.

What is needed, then, in the general field of detecting gases, is a way to distinguish between the presence of one target gas and other gases that are normally present in the free atmosphere at the same time and in the same place as the target gas. What is also needed in target gas detection, such as for the natural gas industry, is to be able to distinguish between natural gas as a target gas and other combustible gases. Moreover, there is a need for an optimal natural gas detector that simultaneously detects both methane and ethane to assure that the detected gas is from a natural gas leak, so as to avoid false natural gas alarms based on the detection, for example, of the noted leaking propane tanks, etc. In addition, there is a need to increase detection distance, that is, to increase the distance from a target gas detection instrument to a remote location of the target gas that is to be detected, and to also increase the detecting speed of such instruments. As well, there is a need to provide an instrument that will have a high sensitivity independently of atmospheric turbulence and variability. Finally, there is a need to remove undesired influences from the target gas signal so as to isolate detector signals representing the target gas. Such undesired influences include, for example, stray atmospheric fluctuations, such as humidity, atmospheric turbulence, changes in the index of refraction, and beam path variation; stray back light, such as the constant thermal emission of the atmosphere and the Earth; and system influences, such as jitter, beam wander and drift, and variation of source illumination.

SUMMARY OF THE INVENTION

Broadly speaking, the present invention fills these needs by providing, for the general field of detecting gases, methods of and apparatus for distinguishing between a target gas and other gases that are normally in the free atmosphere at the same time and in the same place as the target gas. The present invention fills the needs for trace gas detection in the natural gas industry by an ability to distinguish between natural gas as a trace gas and other combustible gases. The present invention also provides a more optimal natural gas detector that simultaneously detects both methane and ethane to assure that the detected methane is from a natural gas leak, so as to avoid false natural gas alarms based on the detection, for example, of leaking propane tanks, etc. The present invention also fills these needs by substantially increasing the detection distance. That is, by the present invention the distance from the detection instrument to a location of the target gas that is to be detected may be up to about fifty-three hundred feet. As a result, mobile platforms, such as trucks and aircraft, may be used to carry the equipment of the present invention during high-speed remote monitoring along long detection paths. In addition, the equipment of the present invention is provided with high sensitivity independently of atmospheric turbulence and variability, and the above-described undesired influences are removed from the trace gas signal so as to isolate detector signals representing the trace gas.

In one embodiment of the present invention, apparatus is provided for detecting at least one target gas in the free atmosphere, and includes a source of light configured to direct light into a region in which the at least one target gas may be present. For detection, there is also at least one gas conelation radiometer for responding to light transmitted through the region. A modulator is included for modulating the light at the source, i.e., before the light is directed into the region. This source modulation is one aspect of removing the above-described undesired influences from the trace gas signal so as to isolate detector signals representing the trace gas.

The present invention also contemplates an embodiment in which the light directed into the free atmosphere is broadband light and the modulator is configured to output the broadband light having either modulated amplitude or modulated frequency.

In yet another embodiment of the present invention relating to such removal of the above-described undesired influences, at least two gas correlation radiometer channels are provided for response to a single beam of light after transmission of the beam through the region. A beam splitter separates the single beam of light into two beams and directs one of the two beams to a separate one of the channels of the gas correlation radiometer. In an optimal configuration, the two separate channels separately and simultaneously respond to the respective one of the two light beams for separately and simultaneously generating signals that together indicate that the target gas is in the free atmosphere through which the single light beam was transmitted.

Another embodiment of the present invention relates to achieving substantially the same instrument conditions for separate light detectors of the separate channels of the gas correlation radiometers. The light detectors have a response to light that is a function of the light received, detector ambient temperature, and a bias voltage input to the detector. A voltage supply is configured to provide each of the detectors with a common bias voltage. A temperature stabilizer very accurately controls the ambient temperature of each of the detectors. As a result, different responses of the two detectors to the light are independent of detector ambient temperature and of the bias voltage input to the detector, but are dependent on the light received by the respective detector.

In another embodiment, the gas correlation radiometer is configured to respond to light transmitted through the region, wherein the wavelength of the light to which the radiometer responds is within a band selected as corresponding to strong infrared (IR) absorption by the target gas and also weak IR absorption by gases present in the free atmosphere as compared to the strong absorption by the target gas.

In another embodiment for use in the natural gas industry, the target gas is each of methane and ethane, and the source of light is configured to direct light into a region in which the methane and the ethane may be present. Further, there are two gas correlation radiometers. An optimized one of the radiometers is configured to respond to light transmitted through the region and having a wavelength within a band of about 1000 to about 3500 cm$^{-1}$. The other optimized one of the radiometers is configured to respond to light transmitted through the region and having a wavelength within a band of about 2970 to about 3005 cm$^{-1}$. The two optimized gas correlation radiometers are configured to simultaneously detect any respective ethane and methane in the region into which the light is transmitted so that the combined simultaneous output of the two optimized gas correlation radiometers may indicate the presence in the region of natural gas.

In a natural gas detection embodiment that is configured to be mounted on a vehicle, such as a ground-based vehicle or an aircraft, the apparatus is configured with two gas correlation radiometers, each having a separate background channel and a separate gas channel. The background channel of the methane gas correlation radiometer is configured with a blank cell to output blank methane data that varies according to whether there is methane in the region. The gas channel of the methane gas correlation radiometer is configured with a methane cell to output methane data that is independent of whether there is methane in the region. The background channel of the ethane gas correlation radiometer is configured with a blank cell to output blank ethane data that varies according to whether there is ethane in the region. The gas channel of the ethane gas correlation radiometer is configured with an ethane cell to output ethane data that is independent of whether there is ethane in the region. The sensitivity of the apparatus to methane and ethane is rendered independent of atmospheric turbulence and variability by providing a computer programmed to process the data resulting from the simultaneous detection of the ethane and methane in the region into which the light is transmitted. For the ethane data and the methane data, the computer is programmed to compute an output based on Equations (1) and (2), as follows:

$$\text{output for ethane} = (\text{Ratio}_{measured\ E}/\text{Ratio}_{null\ E}) - 1; \quad \text{Equation (1)}$$

wherein $\text{Ratio}_{measured\ E}$ is the ratio of the ethane data to the blank ethane data, and wherein $\text{Ratio}_{null\ E}$ is the ratio of the ethane data measured without the ethane cell in the respective gas channel of the respective gas correlation radiometer, to the blank ethane data measured without the blank cell in the respective blank channel of the respective gas correlation radiometer, $$\text{output for methane} = (\text{Ratio}_{measured\ M}/\text{Ratio}_{null\ M}) - 1; \quad \text{Equation (2)}$$

wherein $\text{Ratio}_{measured\ M}$ is the ratio of the methane data to the blank methane data, and wherein $\text{Ratio}_{null\ M}$ is the ratio of the methane data measured without the methane cell in the respective gas channel of the respective gas correlation radiometer, to the blank methane data measured without the blank cell in the respective blank channel of the respective gas correlation radiometer.

Embodiments of the present invention include a method of selecting an optimum center wavelength and an optimum bandpass of wavelengths of light to be processed by a gas correlation radiometer after transmission of the light through the free atmosphere in which there may be a trace amount of a target gas and in which there is likely to be at least one competitive other gas the presence of which in the free atmosphere may interfere with detection of the target gas. The optimum center wavelength and the optimum bandpass are used in optimizing a response of a gas correlation radiometer to the trace amount of the target gas. The method may include an operation of determining a set of similarity data as a function of overlap regions within a spectral region. The overlap regions are for each competitive gas and the target gas and are those regions within the spectral region in which respective absorption spectra of both the target gas and the competitive gas have absorption characteristics. The set of similarity data include a plurality of data items within each of a plurality of bandpasses, wherein one of the data items corresponds to a center wavelength within each bandpass. The method may also include an operation of determining a set of contrast data as a function of non-overlap regions within the spectral region, the non-overlap regions being for each of the competitive gas and the target gas and being those regions within the spectral region in which the first absorption spectrum has high absorption characteristics but the second absorption spectrum has low absorption characteristics. The set of contrast data include a plurality of data items within each of a plurality of bandpasses, wherein one of the data items corresponds to a center wavelength within each bandpass. Optimization is completed by selecting the center wavelength and bandpass of an infrared filter for use with the gas correlation radiometer. Such selection is based on plotting a curve for each of various bandpasses. Each curve plots the contrast data item minus the similarity data item as a function of the center wavelength. The selected center wavelength and bandpass have the highest value of contrast data item minus the similarity data item.

The invention also provides a lock-in amplifier configured to receive electronic signals produced by first and second detectors of a gas correlation radiometer. The amplifier isolates the source-modulated broadband light signal from any ambient steady-state thermal emission background that may be present along a target gas detection path.

BRIEF DESCRIPTION OF THE DRAWINGS

The present invention will be readily understood by reference to the following detailed description in conjunction with the accompanying drawings, in which like reference numerals designate like structural elements.

DETAILED DESCRIPTION OF THE PREFERRED EMBODIMENTS

An invention is described for a method of and apparatus for detecting gases, especially trace amounts of target gases, such as natural gas, remotely along long-range paths in the free atmosphere. The exemplary natural gas detection is preferrably enabled by simultaneously remotely detecting methane and ethane along the same long-range path in the free atmosphere. Details are described for systems and methods in which an active gas correlation radiometer is configured with separate and simultaneously operating background and gas channels. The background channel is configured with a blank cell to output data that varies according to whether there is target gas along the path in the free atmosphere. The gas channel is configured with a target gas cell to output other data that is independent of whether there is target gas along the path in the free atmosphere. It will be obvious, however, to one skilled in the art, that the present invention may be practiced without some or all of these specific details. In other instances, well known apparatus or process operations have not been described in detail in order not to obscure the present invention.

Figure 1A:
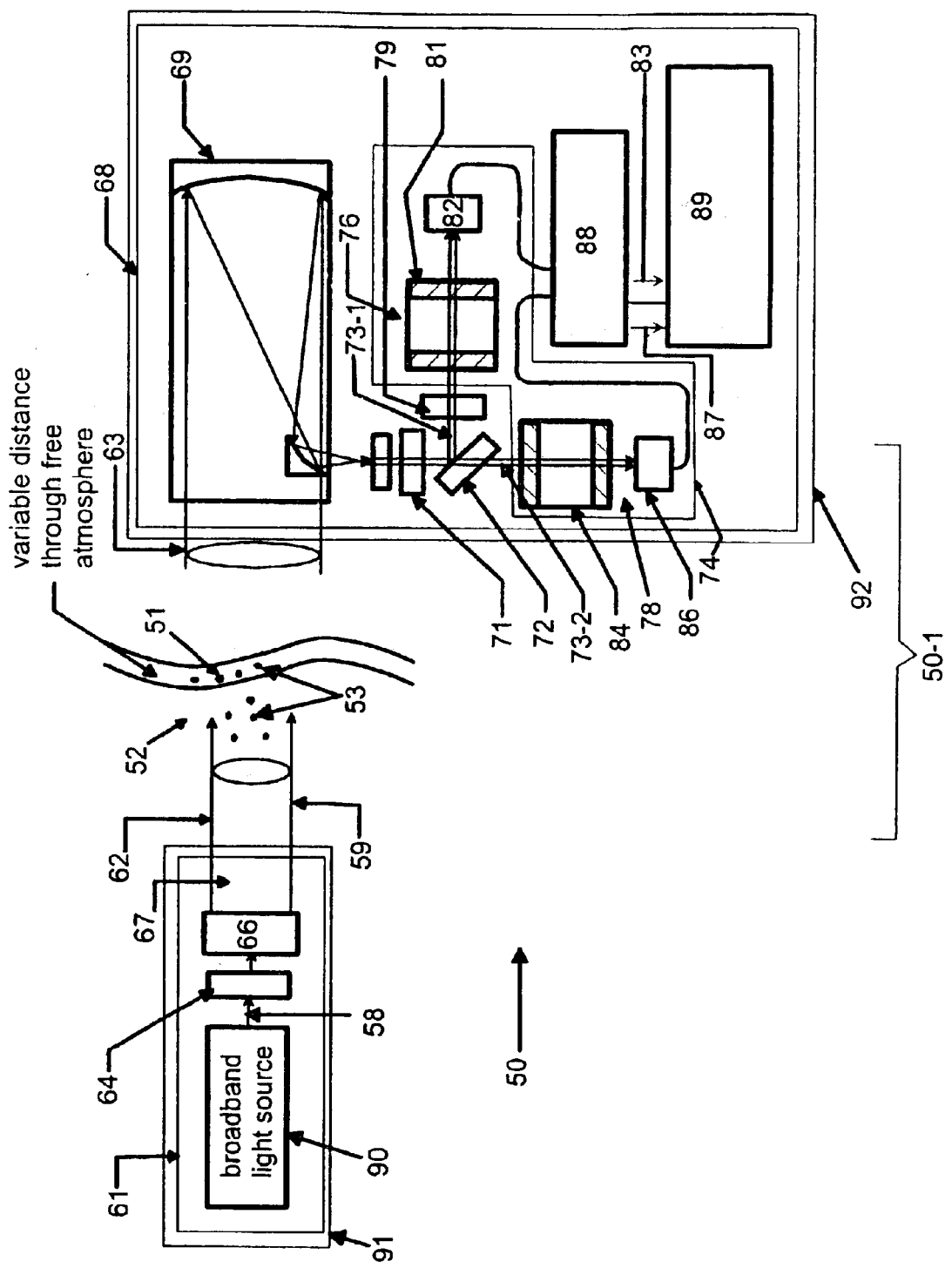
FIG. 1A is a schematic diagram of a system of the present invention illustrating an apparatus for detecting trace amounts of target gases, such as natural gas, remotely along a fence line detection path in the free atmosphere.
Figure 4:
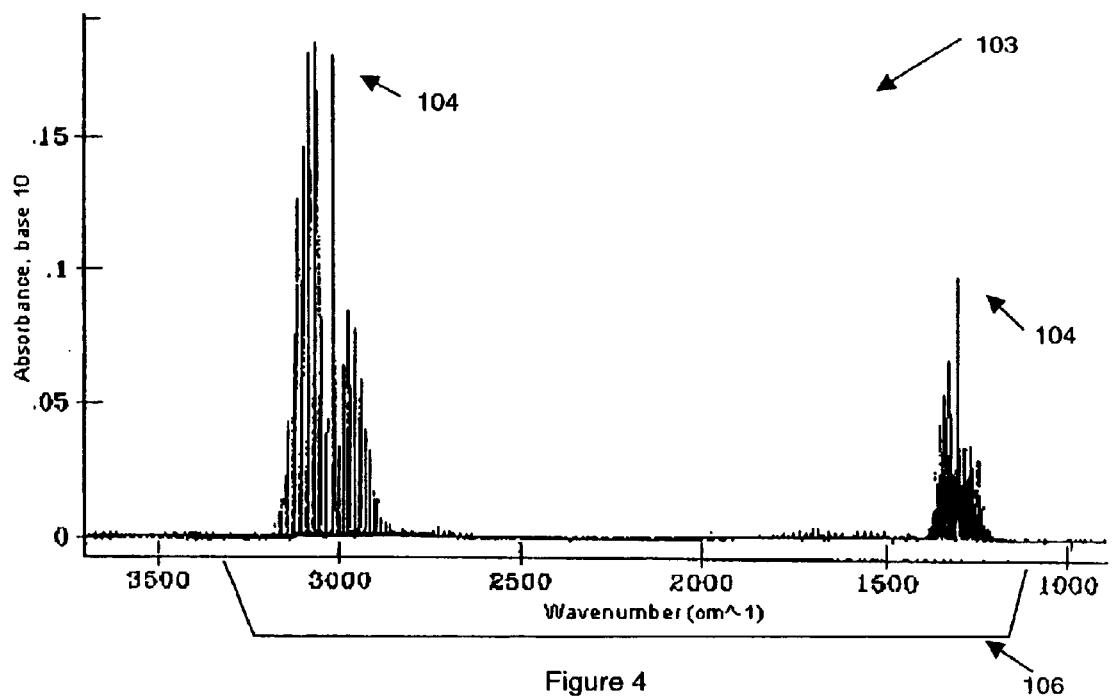
FIG. 4 is a graph illustrating an exemplary infrared absorption spectrum for the target gas methane as provided by an operation of the method of FIGS. 3A and 3B.

A system 50 of the present invention is shown in FIG. 1A for detecting the presence of trace amounts of a specific gas 51 within the free atmosphere 52. The specific gas 51 is one gas of many gases that may exist in the free atmosphere 52. For purposes of description, the gases that may exist in the free atmosphere 52 other than the specific gas 51 are referred to as background, or competitive, gases 53. In the sense that in the system 50 the specific gas 51 is "targeted", i.e., specifically identified for detection, and during detection the specific gas 51 is not confused with any of the many other competitive gases 53, the specific gas 51 is referred to as the "target" gas. Similarly, in the sense that in the system 50 there may be many specific gases 51 that are "targeted" for detection and during detection the specific gases are not confused with any of the many other competitive gases 53, the specific gases 51 are referred to as the "target" gases. Reference herein to one target gas 51 may include reference to more than one target gas 51 as the context permits. The potential target gases 51 which may be detected by the system include, but are not limited to, CH4, NO, SO2, NO2, NH3, HNO3, OH, HF, HCl, HBr, HI, COI, OCS, H2CO, HOCl, N2, HCN, CH3Cl, H2O2, C2H2, C2H6, and PH3. As described below in regard to FIG. 4, such target gases 51 have "rich" absorption spectra.

In the absence of the system 50, local conditions in the free atmosphere 52 may render such detection of the target gases 51 difficult. Such difficulty may be based, for example, on the fact that the target gases 51 may only be present in the free atmosphere 52 in trace amounts. Trace amounts may be in such low concentrations as about one or a few parts per billion (PPB), or in such concentrations as to approach a pure gas (~10×10⁸ PPB). Such low concentration of one or a few PPB is the lower end of a trace gas detection range of the system 50 with respect to certain trace gases 51, such as ethane, for example. Such lower end is also referred to as the "minimum detectable concentration" of the system 50.

In contrast to such trace amounts, the concentration of water vapor in the free atmosphere 53 is generally measured as 30,000 parts-per-million (PPM)-. The water vapor concentration within the free atmosphere 52 is highly variable and is determined by the season, altitude, latitude, and local weather events, for example. Generally, such water vapor concentration may vary from 1,000 to 40,000 PPM, whereas the concentration of the target gas methane 51 is due to natural background (biological) sources and is typically in the range of from about 0.5 PPM to about 5.0 PPM within the free atmosphere 52. Since natural gas is almost entirely comprised of methane, the methane concentration leaking from the pipe, at the site of the leak, approaches 8×10⁵ PPM (~80% of pure gas). However, the methane rapidly dilutes into the free atmosphere 52, and the methane concentration rapidly approaches that of the natural background methane concentration. Due to the limited sensitivity described above, the Flame Ionization Detectors have a combustible gas concentration threshold on the order to 10 to 100 PPM to indicate a potential natural gas pipeline leak. As described below, the system 50 may provide a minimum detectable methane concentration of approximately 50 PPB, which is a higher minimum detection concentration than for ethane because of the lower depth of IR absorption of the methane IR absorption spectrum as compared to the depth of IR absorption of the ethane IR absorption spectrum.

Figure 2A:
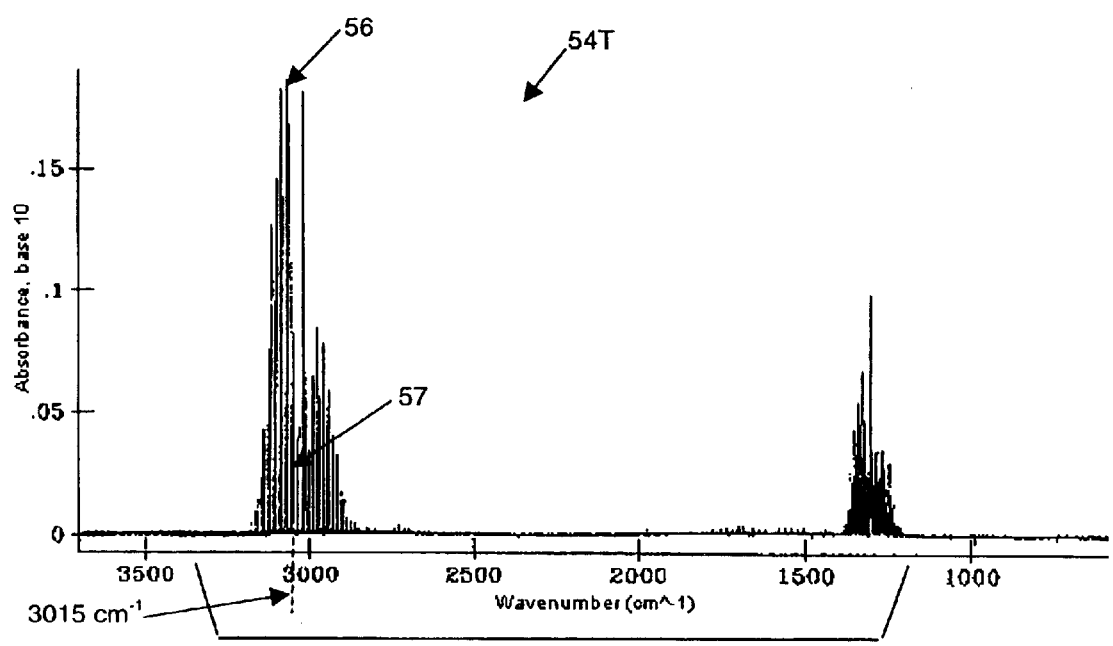
FIGS. 2A and 2B depict infrared absorption spectra of a respective target gas and competitive gas, illustrating overlapping lines of high infrared absorption of both gases.
Figure 2B:
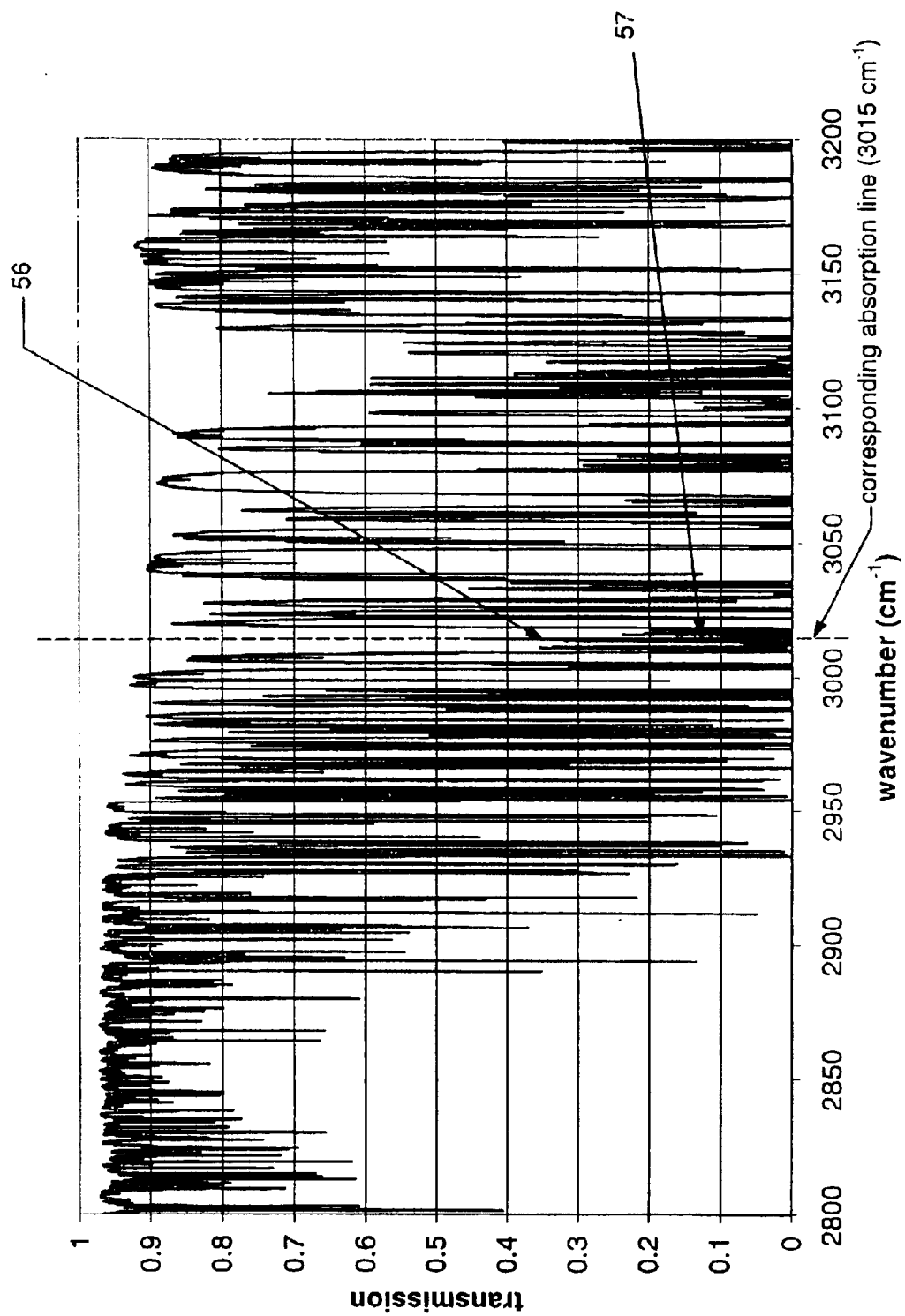

Difficulty of such detection may also result when the target gas 51 is mixed with, or present with, the competitive gases 53. The competitive gases 53 may include water vapor and/or undesired (non-target) background gases that may be in the same free atmosphere 52 as contains the target gas 51, for example. The competitive gases 53 are referred to as "competitive" gases because such gases 53 are not a target gas 51, yet there are overlaps 56 in absorption spectra 54 of the target gas 51 and the background gases 53. FIGS. 2A and 2B depict respective exemplary infrared absorption spectra 54T and 54C of such respective target gas 51 and competitive gases 53, wherein the overlap 56 is at an absorption line 57 having a wavenumber at about 3015 cm⁻¹. The spectrum 54C is a portion of a spectrum for United States Standard Atmosphere at certain conditions, and the spectrum 54T is a portion of a methane spectrum, for example.

The free atmosphere 52 shown in FIG. 1A is an open and uncontained part of the Earth's atmosphere. The free atmosphere 52 is distinguished from containers (not shown) in which samples of a target gas 53 may be received for analysis by prior art equipment (not shown). Such target gas 51 in the containers is not "free". The free atmosphere 52 is subject to weather-related changes in pressure, temperature, atmospheric turbulence and variability, for example, as well as changes due to industrial and residential events. Such events may include discharge into the free atmosphere 52 of target gas 51 and competitive gases 53, for example.

Light 58 transmitted by the system 50 may be directed along a detection path 59 through the free atmosphere 52. At any moment of time, the light 58 is subjected to the current conditions of the free atmosphere 52 at a particular place, or location, along the detection path 59. Light 58 arriving at that same particular location at a next moment of time is subjected to later, then-current, conditions of the free atmosphere 52. Because the conditions of any such particular location of the free atmosphere 52 along the detection path 59 may vary from time to time (e.g., from one tenth of a second to a next tenth of a second, for example) the conditions of the free atmosphere 52 vary temporally, and are said to be dynamic.

FIG. 1A also shows the system 50 configured with a source 61 of the light 58. The source 61 is active, that is, the source is configured to produce and direct the light 58 into the free atmosphere 52. The light 58 is directed along the detection path 59, which is a beam-like region in which the target gas 51 and the competitive gases 53 may be present. In a general sense, the light 58 is broadband radiation within a range of wavenumbers from about 0.2 micrometers to about one hundred micrometers. The source 61 of a fence line embodiment 50-1 (FIG. 1A) of the system 50, for example, may be configured to direct the light 58 from a transmission location at a near end 62 of the detection path 59 to a far end 63 at a receiver location spaced from the transmission location. Such spacing of the ends 62 and 63 may be from about thirty feet to about 5300 feet, which in turn provides a selected length of the detection path 59 as described below with respect to various embodiments 50-1 through 50-5 of the system 50.

At the transmission location, the source 61 may be provided with a modulator 64 and beam forming optics 66, to provide the light 58 in the form of a collimated modulated light beam 67. The collimated modulated light beam 67 is thus generated at the source 61 and is transmitted from the near end 62 along the detection path 59 through the free atmosphere 52 to the far end 63. In an embodiment 50-5 described below in which modulation of the light beam 67 is not required, the modulator 64 is not part of the source 61. The light beam 67 is transmitted along the detection path 59 through any competitive gas 53 and through any target gas 51. During such transmission, depending on the atmospheric conditions along the detection path 59, the light 61 may be absorbed, scattered, or reflected, and such, absorption, scattering, and reflection may vary with location along the detection path 59, or with time, or with respect to the length of the detection path 59, for example. While such scattering or reflection may divert the light beam 67 from the detection path 59, such absorption may result from infrared absorption typified by FIGS. 2A and 2B, for example. Such absorption, scattering, and reflection reduce the intensity of the light beam 67.

FIG. 1A shows the light beam 67 at the far end 63 of the detection path 59 entering a receiver 68 of the system 50. The receiver 68 is configured with a receiving telescope 69 that focuses the light beam 67 for transmission through an infrared (IR) filter 71. The IR filter 71 is configured with an optimized central wavelength and an optimized bandpass as described below to provide substantially increased sensitivity to a specific one of the target gases 51 and substantially increased selectivity of that target gas 51 to avoid erroneous detection of any competitive gas 53 as that target gas 51. The receiver 68 is configured so that the IR filter 71 transmits the light 58 having the now-optimized central wavelength and the now-optimized bandpass to a beam splitter 72. The beam splitter 72 is configured to provide two split light beams 73 that are transmitted simultaneously to, and simultaneously enter, a dual-channel gas correlation radiometer (GCR) subsystem 74.

The GCR subsystem 74 is configured with two separate channels 76 and 78 that simultaneously receive the respective split light beams 73 having the optimized central wavelength and the optimized bandpass. A first of the beams 73-1 is transmitted through the channel 76, which is configured with a neutral density filter 79 and a blank cell 81. The first channel 76 is configured with a first detector 82 which outputs blank channel data 83 that varies according to whether there is target gas 51 in the detection path 59 through which the light beam 67 was transmitted on the way to the receiver 68. A second of the beams 73-2 is transmitted through the channel 78, which is configured with a target gas cell 84. The second channel 78 is configured with a second detector 86 which outputs target gas channel data 87 that is independent of whether there is target gas 51 in the region, i.e. along the detection path 59 through which the light beam 67 was transmitted on the way to the receiver 68. The blank channel data 83 and the target channel data 87 are supplied to a lock-in amplifier 88, the output of which is applied to a display and data processor 89. The splitting of the light beam 67 in this manner results in the simultaneous reception by the processor 89 of the data 83 and 87 for simultaneous processing.

Figure 1B:
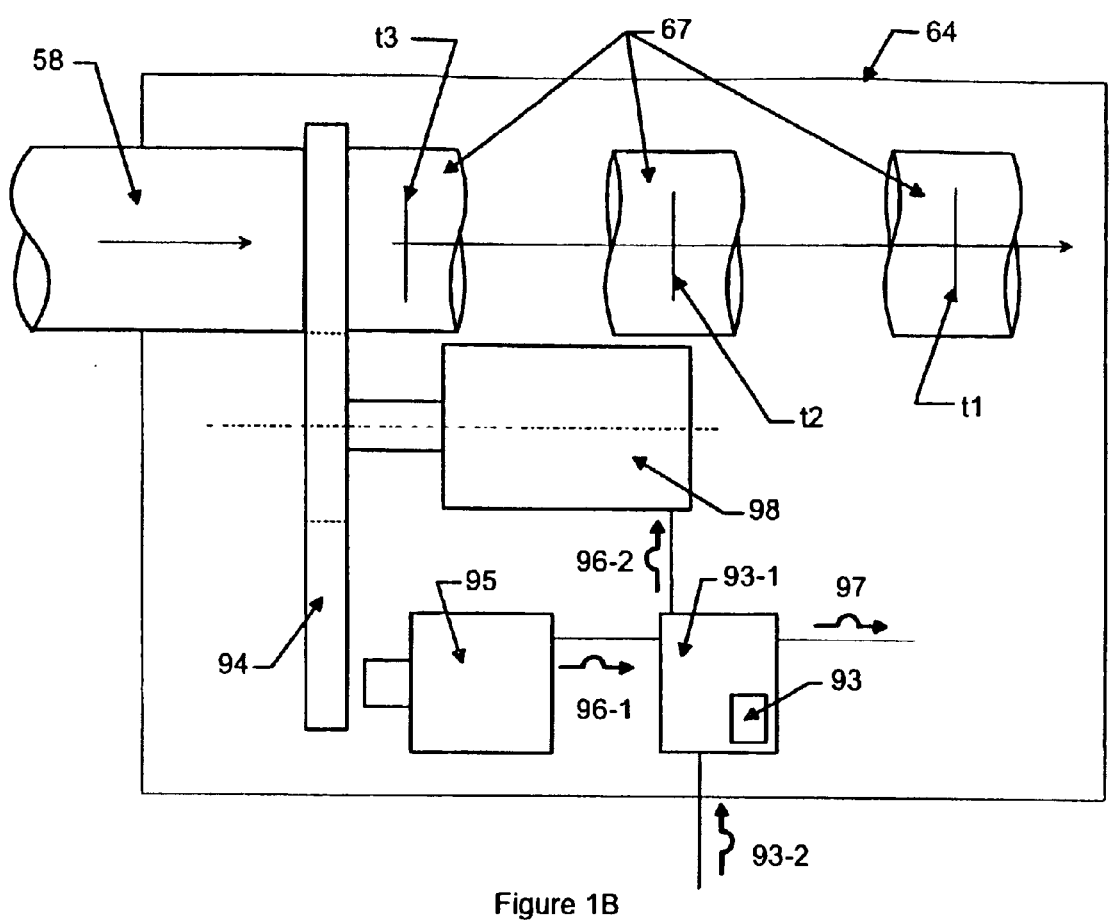
FIG. 1B is a schematic diagram illustrating a light source provided with a modulator configured with a crystal oscillator for controlling a rotating wheel that alternately blocks and passes a light beam from the source.

Because of the modulation at the source 61, the modulated collimated light beam 67 has been subjected to the atmospheric conditions along the detection path 59 at successive moments of time (see successively later times t1, t2, and t3, for example, in FIG. 1B) during which the light beam 67 is transmitted from the near end 62 to the far end 63 of the detection path 59. Such atmospheric conditions further modulate the light beam 67, but this further atmospheric modulation is different from the modulation by the modulator 64 at the source 61. The lock-in amplifier 88 selects from this combination of modulated light 58 only the light 58 having the modulation imposed by the modulator 64 at the source 61, such that the data 83 and 87 do not include the effects of atmospheric turbulence, jitter, beam wander, and changes in the index of refraction, for example. Thus, each of the data 83 and 87 received by the processor 89 at any moment of time represents the influence of the same current atmospheric conditions of the free atmosphere 52 as the light 58 is transmitted along the detection path 59, as may have been modified only by transmission through the respective channels 76 and 78. As described above, the first detector 82 outputs the blank channel data 83 that varies according to whether there is target gas 51 in the detection path 59 through which the light beam 67 was transmitted on the way to the receiver 68. The second detector 86 outputs target gas channel data 87 that is independent of whether there is target gas 51 in the region, i.e. along the detection path 59 through which the light beam 67 was transmitted on the way to the receiver 68. The channels 76 and 78 thus modify the light beam 67 so that together the data 83 and 87 represent various factors. The factors include whether or not there was target gas 51 along the detection path 59 during the successive moments of time t1, t2, t3, etc. during which the light beam 67 was transmitted from the near end 62 to the far end 63 along the detection path 59, and if target gas 51 was detected, the concentration of the target gas 51.

Considering the structure and operation of the system 50 shown in FIG. 1A in more detail, the source 61 is configured with a broadband light source 90 that may output the broadband light 58 described above. The light source 90 may be a thermal lamp configured for high infrared output. A suitable lamp is a blackbody source having an output spectrum that follows the universal blackbody relationship in which the intensity of the light 58 output is proportional to $T_{color}$, the color temperature of the lamp. For example, the following may be used for the light source 90: silicon carbide lamps (having a $T_{color}$ of ~1000 Kelvin (K)), halogen lamps (having a $T_{color}$ or of ~3000 K), Xe lamps (having a $T_{color}$ of ~6000 K), tungsten lamps (having a $T_{color}$ of ~5000 K), and plasma glow lamps (having an output equivalent to the Xe lamp). The Xe lamp, for example, can achieve a total optical power output of about seventy-five Watts. The plasma glow lamp may be a glowing one millimeter (mm) plasma sphere, mounted at the focal point of an elliptical reflective mirror. The plasma glow lamp has a surface emission temperature of 6000 K, a total optical output of 75 watts, and an output of ~6 milliwatts within the typical bandpass of the IR filter 71. Another blackbody source suitable for use as the light source 90 is an arc lamp, which may be physically smaller and more-efficient than the glowing plasma sphere. The arc lamp produces about three milliwatts in the optical bandwidth (about 2800 to 3200 $cm^{-1}$) required for detection of methane and ethane as the target gases 51. As the length of the detection path 59 increases, it is preferable to use the source 90 having the higher $T_{color}$.

Suitable broadband sources 61 must be capable of transmitting the generated light 58 into the free atmosphere 52. In order to assure that the source-generated light 58 is transmitted into the free atmosphere 52, the broadband source 61 is not encased in outer bulbs, and does not have other optical elements (collectively "optical components"), that do not transmit well at the wavelengths of interest for the detection of the target gas(es) 51. When the target gas 51 is either methane or ethane, for example, quartz, germanium, and silicon optical components are not used since they do not provide for the optimal transmission of the source-generated light 58 into the free atmosphere 52. In a preferred embodiment of the source 61, potassium bromide may be used for the optical components since it has adequate optical transmission. However, potassium bromide scratches easily. In a more preferred embodiment of the source 61, sapphire is used for the optical components because sapphire transmits well (>90%) in a range from the visible wavelengths to approximately 7 $\mu m$ and is more durable than potassium bromide.

In review, the wavelength of the light 58 output from the source 90 may be broadband, preferably in the range of about 0.2 micrometers to about one hundred micrometers, for example. More preferably, the wavelength of the light 58 output from the source 90 may be in the range of about 3 micrometers to about 10 micrometers. Most preferably, the wavelength of the light 58 output from the source 90 is in the range of about 3.12 micrometers to about 3.57 micrometers. Each such range of wavelengths may be referred to as being "broadband" in the sense that these ranges are substantially broader than the narrow emission spectra used in the TDLAS, laser absorption spectroscopy and DIAL instruments described above.

The fence line embodiment 50-1 of the system 50 shown in FIG. 1A may be provided with a transmitter housing 91 at the transmitter location adjacent to the near end 62 of the detection path 59. The fence line embodiment 50-1 may also be provided with a receiver housing 92 at the receiver location adjacent to the far end 63 of the detection path 59. When the detection path 59 is in a range of lengths from about thirty feet to about 100 feet, the modulator 64 may be hard-wired to the lock-in amplifier 88 for directly transmitting to the amplifier 88 a demodulator signal (not shown) that is in-phase and in-frequency with the modulating frequency of the modulator 64. However, when the detection path 59 is in a range of lengths from about 100 feet to about 5,300 feet, the modulator 64 cannot be hard-wired to the receiver 68. In this situation, as described below, based on receipt of data (or signals) derived from the source-modulated split light beams 73 the lock-in amplifier 88 determines the frequency and phase of the received split light beams 73 and locks to such frequency and phase.

Figure 13:
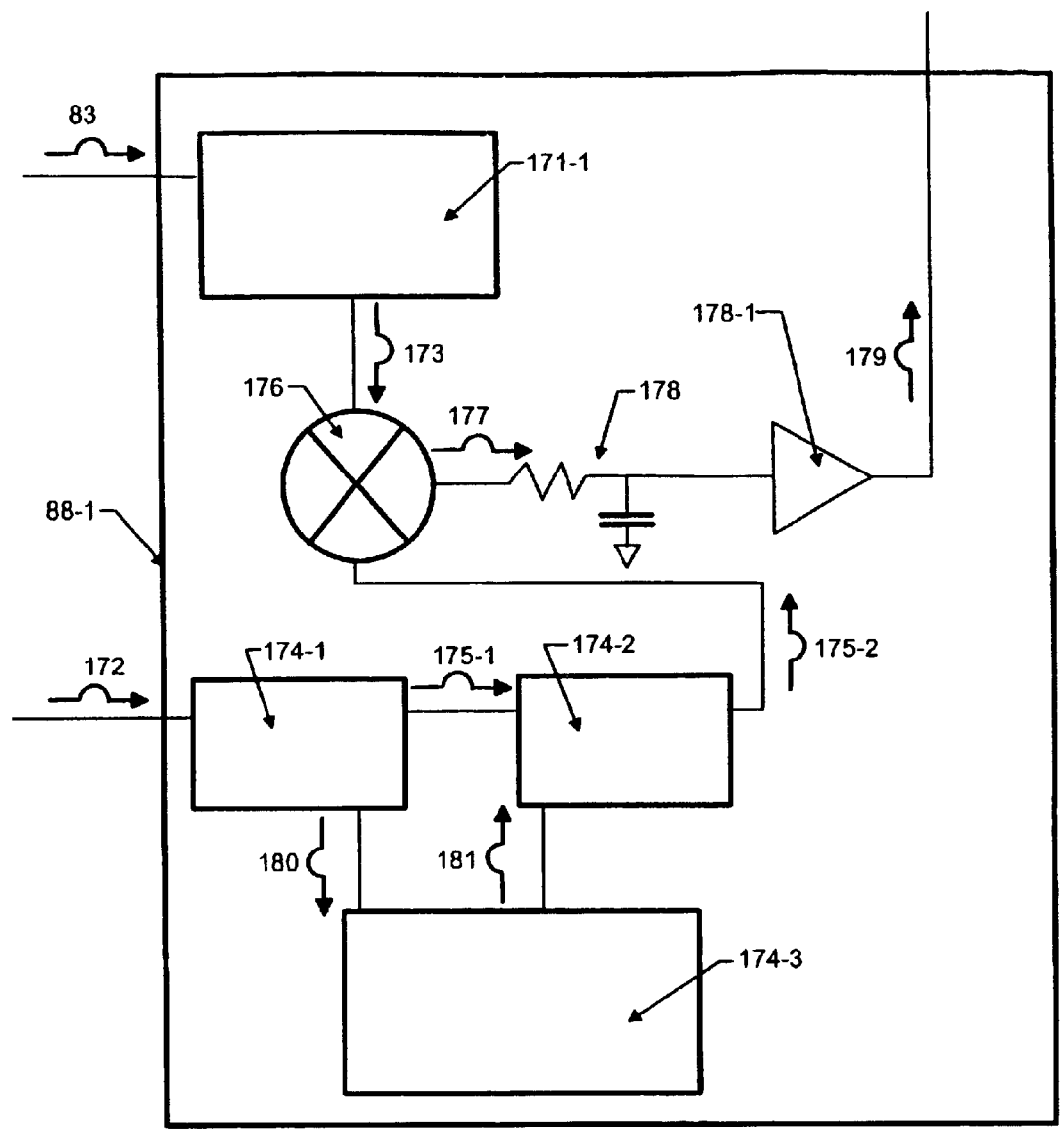
FIG. 13 is a schematic diagram illustrating lock-in amplifier circuitry of the system.

In one embodiment of the system 50 the source 61 may be configured with the modulator 64 for amplitude modulation, such as by use of a chopper having sequentially positioned openings, or an electro-magnetically driven tuning fork, for example. FIG. 1B shows a preferred embodiment in which the source 61 may be provided with the modulator 64 configured with an internal crystal oscillator 93 and motor control circuit 93-1 to provide closed-loop control of the modulation frequency. A rotating wheel 94 alternately blocks and passes the light beam 67. In this embodiment, the user selects the desired modulation rate through an external input 93-2. The motor control circuit 93-1 tunes the output of the internal oscillator 93 to this value. The modulator 64 includes an optical pick-off 95 associated with the wheel 94 for providing an output signal 96-1 that is provided to the motor control circuit 93-1. The motor control circuit 93-1 compares the optical pick-off output 96-1 with the output from the crystal oscillator 93, which was previously tuned to the user input 93-2. Then, the motor control circuit 93-1 either speeds-up or slows-down the rotation of the wheel 94 by providing appropriate drive signals 96-2 to a chopper motor 98. In this manner, the optical modulation frequency is precisely controlled to a user-selectable value using the precision crystal oscillator 93. In addition, the motor control circuit 93-1 provides a reference signal 97 which is precisely in phase with, and at the same frequency as, the optical modulation frequency. This reference signal 97 may be provided to the lock-in amplifier circuit 88 (FIG. 13). Using this arrangement, the optical modulator 64 provides a precision, selectable chopping or modulation, frequency, which preferably is 1 kHz±0.01 Hz, or 10 parts-per-million. In a more general sense, the modulation frequency is well above the 1/f noise of the detectors 82 and 86.

In another embodiment, the source 61 may be configured with the modulator 64 for frequency modulation, such as by use of a pressure cell through which the light 58 from the source 90 is transmitted.

FIG. 1A shows the beam forming optics 66, which may be an amateur-grade telescope having total reflectivity. Such telescopes are configured with totally reflective optics and an f-number of 4 (f/4). Such telescopes have the ability to direct the light beam 67 along a 5300 foot detection path 59 with a divergence of a few milliradians, so that if the light beam 67 is eight inches in diameter at the near end 62 the light beam 67 may have a diameter of approximately sixty inches at the far end 63 of the 5300 foot path 59. One advantage of the system 50 is that such telescope 66 having the totally reflective optics for use in the IR region is very low cost as compared to beam forming optics constructed from refractive optics. Such optics 66 may be supplied by Orion, Santa Cruz, Calif.; or Meade of Irvine, Calif., or Celestron International of Torrance, Calif., for example. The receiving telescope 69 may also be an amateur-grade telescope similar to the optics 66, having the ability to receive a portion of the light beam 67 having the diameter of approximately 60 inches at the end 63 of the 5300 foot path 59.

The IR filter 71 is configured (e.g., optimized) for each different target gas 51, such that the optimized central wavelength and the optimized bandpass provide substantially increased sensitivity to the particular target gas 51 and substantially increased selectivity of such target gas 51 to avoid erroneous detection of any competitive gas 53 as the target gas 51. In a preferred embodiment of the IR filter 71, the IR filter 71 is configured to respond to light wavelengths within a band corresponding to strong IR absorption by the specific target gas 51. The band also corresponds to weak IR absorption by gases 53 other than the specific target gas present 51 in the free atmosphere 52. The word "weak" is relative to the stronger IR absorption by the specific target gas 51. It may be said that such band provides a high degree of dissimilarity in the infrared absorption spectra of the respective target gas 51 and competitive gas 53.

Figure 3A:
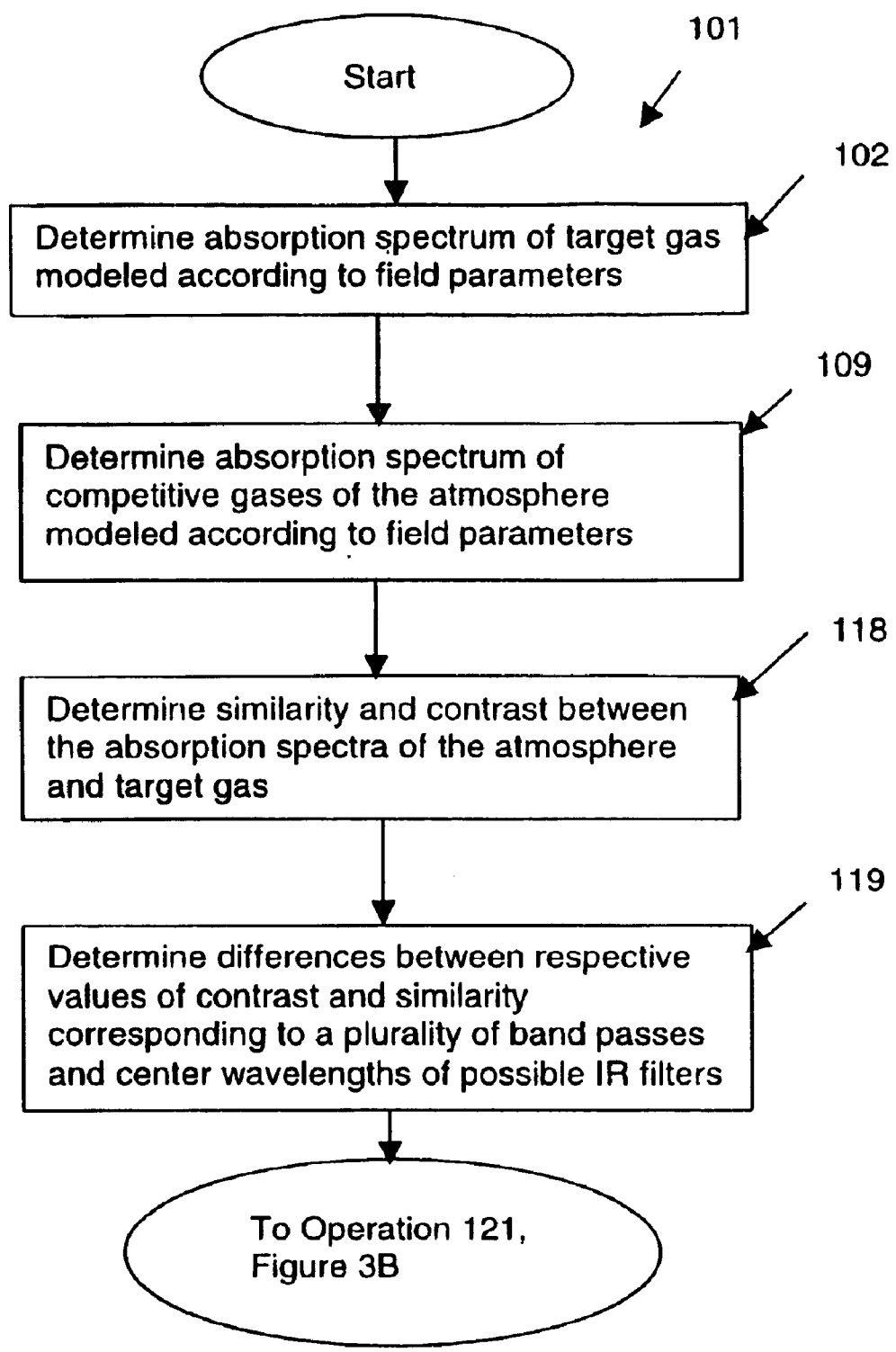
FIGS. 3A and 3B combine to define a flow chart illustrating operations of a method of the invention for determining an optimized central wavelength and an optimized bandpass of an IR filter for each particular target gas.
Figure 3B:
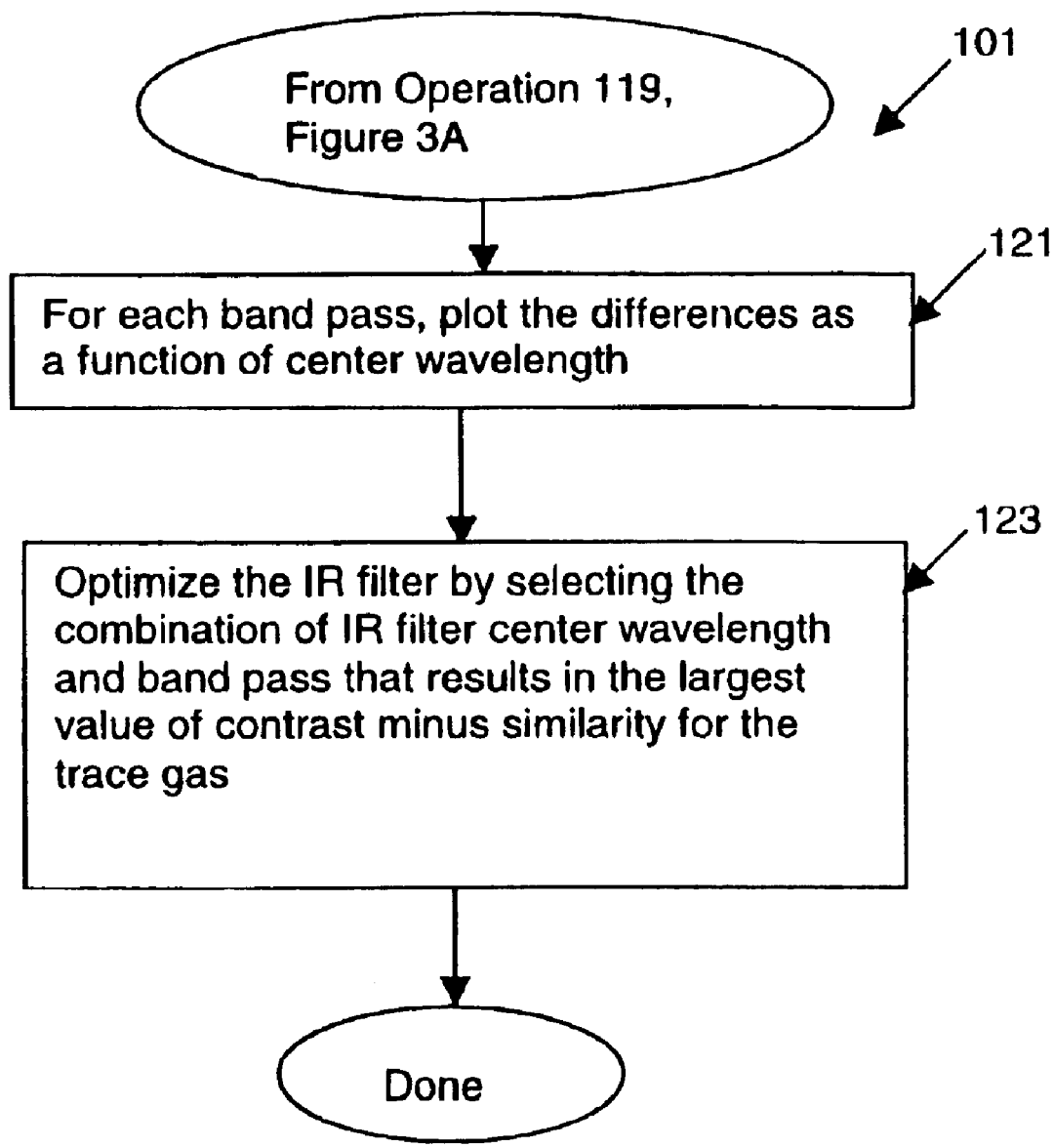

A method of the invention is used to determine the optimized central wavelength and the optimized bandpass for each particular target gas 51. FIGS. 3A and 3B show a flow chart 101 of the method. The method may start by moving to an operation 102 in which a modeled spectrum of the target gas 51 is determined. A typical initial spectrum that may be examined in operation 102 is the exemplary infrared (IR) absorption spectrum 103 shown in FIG. 4, which is for methane, and extends from about wavenumber 3600 $cm^{-1}$ to about wavenumber 700 $cm^{-1}$. This exemplary spectrum 103 may be obtained from the spectral database "Infrared Spectra For Quantitative Analysis of Gases" by P. L. Hanst and S. T. Hanst, Infrared Analysis Inc., Anaheim, Calif., for example. The target gas 51 preferably has a spectrum 103 that is "rich", in that there are strong absorption lines 104 in a wide range 106 of wavenumbers (e.g., from about 3200 to about 1300 $cm^{-1}$). The target gases 51 listed above are examples of target gases 51 having rich absorption spectra.

Figure 5:
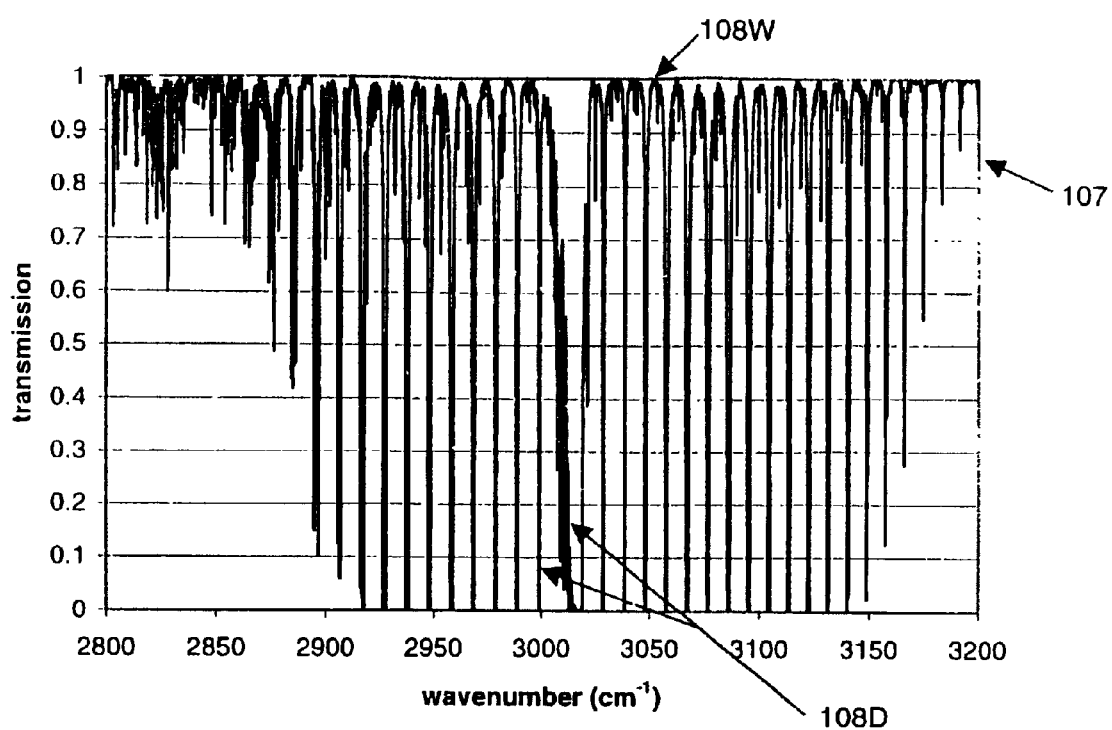
FIG. 5 is a graph illustrating a typical infrared transmission spectrum resulting from modeling of methane for selected parameters as provided by an operation of the method of FIGS. 3A and 3B.

The determination of the exemplary target gas IR spectrum 103 in operation 102 may also include modeling the absorption features for the target gas cell 84. Such modeling may be performed using a suitable line-by-line database, such as the U.S. Air Force Research Laboratory database High Transmission Database, U.S. AFRL, PL/GPOS, Hanscom AFB, Mass. (known as "HITRAN") The spectral absorption features for a specific optical geometry may be obtained by use of computer software such as the U.S. AFRL FASCODE ("Fast Atmospheric Signature Code"), U.S. AFRL, PL/GPOS, Hanscom AFB, Mass.; or a PCLNWIN program made by Ontar Corporation, North Andover, Mass., or the "HITRANPC" program of the University of South Florida. Preferably, the parameters used in such modeling should generally be those to be experienced in the free atmosphere 52 in actual field use of the system 50. More preferably, the parameters should be those reasonably expected to be present in the free atmosphere 52 in actual field use of the system 50. Most preferably, the parameters used in such modeling should be those known to exist most frequently in the particular location of the free atmosphere 52 in which the system 50 is to be used. This modeling provides, or tailors, the IR absorption spectrum (e.g., the spectrum 103 of FIG. 4) for such parameters, which may include the concentration, pressure and temperature of the target gas 51, and the pathlength through the optical geometry. For example, the wavelength, breadth and transmission characteristics of the target gas 51 change with changes in such parameters. FIG. 5 shows a typical transmission spectrum 107 resulting from such modeling of methane for the parameters one centimeter (cm) pathlength, 288.2 K methane temperature, and one atmosphere methane pressure. The exemplary temperature and pressure parameters are the same as the U.S. Standard Atmosphere model at sea level (see Anderson, G. P, et al., Report AFGL Atmospheric Constituent Profiles, 0–120 km, Report No. AFGL TR-86-0110, Air Force Geophysics Laboratory, Hanscom AFB, Mass., 1986, for example).

The exemplary modeled absorption spectrum 107 shown in FIG. 5 includes many deep, or highly absorbing, IR absorption lines 108D. It may be understood that FIG. 5 represents, for methane as an exemplary target gas 51, the results of the operation 102, which identifies a spectral region of a first absorption spectrum of the target gas 51. The spectral region is the wavenumber region from 2800 to 3200 cm$^{-1}$, and the spectrum corresponds to the above-described selected parameters of target gas concentration, target gas temperature, target gas pressure, and path length through the target gas 51. The spectral region has the plurality of high (or deep) absorption lines 108D and low absorption lines 108W. In summary, operation 102 (FIG. 3A) involves identifying a first absorption spectrum of the target gas 51 corresponding to selected gas concentration, temperature, pressure, and path length.

Figure 6:
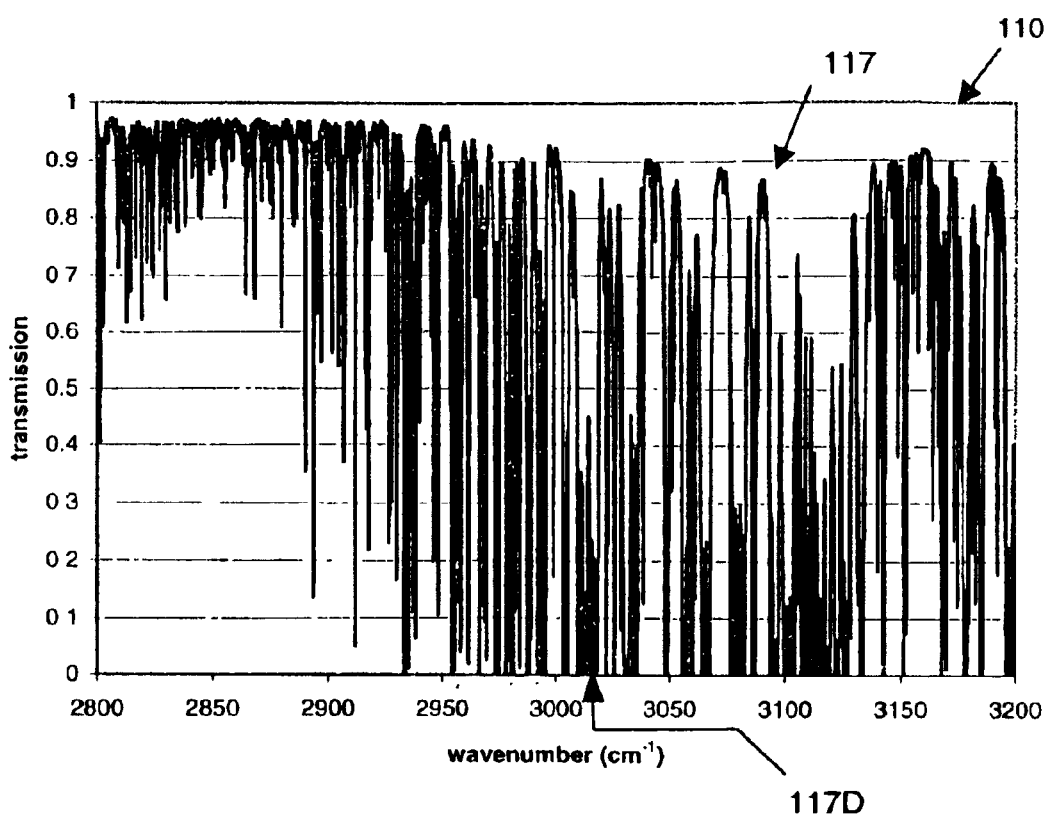
FIG. 6 is a graph illustrating a typical infrared transmission spectrum determined for at least one competitive gas as provided by an operation of the method of FIGS. 3A and 3B.

The method of flow chart 101 moves to operation 109 in which an absorption spectrum 110 (e.g., see FIG. 6) is determined for at least one competitive gas 53 that is, and preferably for all typical competitive gases 53 that are, expected to be in the free atmosphere 52 in the detection path 59 in the use of the system 50. Considering the spectrum 110 as corresponding to all such gases 53, the spectrum 110 may be that obtained from a suitable line-by-line database, such as the above-identified HITRAN database. The spectral absorption features for a specific optical geometry of all of the competitive gases 53 may be obtained by use of computer software, such as one of the above identified FASCODE, PCLNWIN or HITRANPC programs, for example. The order of preference of the parameters used in such modeling are as described above for the target gas 51. This modeling also tailors the combined absorption spectra of the competitive gases 53 for such parameters, which may include the concentration, pressure and temperature of the competitive gases 53, and the pathlength through the optical geometry. For example, the wavelength, breadth and transmission characteristics of the competitive gases 53 change with changes in such parameters. FIG. 6 shows a typical absorption spectrum resulting from such modeling of the competitive gases 53 in the U.S. Standard Atmosphere, modeled at sea level conditions for the parameters of: 23 km visibility aerosols, one km pathlength, 288.2 K atmospheric temperature, and one atmosphere gas pressure. The exemplary modeled absorption spectrum 110 shown in FIG. 6 also includes many deep, or highly absorbing, absorption lines 117D, and many weak absorbing lines 117W. The modeling represented by FIG. 6 includes competitive gases 53 such as H2O, O2, O3, N2O, CO, CO2, and CH4. Also, the U.S. Standard Atmosphere includes possible target gases 51 such as NO, SO2, NO2, NH3, HNO3, OH, HF, HCl, HBr, HI, ClO, OCS, H2CO, HOCl, N2, HCN, CH3Cl, H2O2, C2H2, C2H6, CH4 and PH3.

It may be understood that FIG. 6 represents, for all of the competitive gases 53 as exemplary competitive gases 53, the results of operation 109. FIG. 6 is for the spectral region from wavenumber 2800 to 3200 cm$^{-1}$, and provides the absorption spectrum 110 corresponding to the above-described parameters. The spectrum 110 includes the non-absorbing regions (the lines 117W) corresponding to the low-absorption characteristics (lines 108W, FIG. 3A) of the exemplary methane absorption spectrum 107, and the highly absorbing lines 117D corresponding to deep-absorption characteristics (lines 108D) of such absorption spectrum 107. In summary, operation 109 involves identifying a second absorption spectrum of each of at least one other competitive gas 53. The second absorption spectrum corresponds to the selected gas concentration, temperature, pressure, and path length.

Having the absorption spectra 107 and 110, a preferred embodiment of the invention may compare the IR absorption spectrum 107 to the IR absorption spectrum 110 to identify one wavelength range in which there is a high degree of dissimilarity in the IR absorption spectra. The dissimilarity is indicated by wavelengths in the range at which there is high IR absorption by the target gas 51 and low IR absorption by the at least one competitive gas 53.

A more preferred embodiment of the invention configures the IR filter 71 with a band pass that is optimal for detecting the trace amounts of the target gas 51. The optimal band pass includes infrared absorption features of the target gas 51 to be detected and a suitable transmission region of all common gaseous constituents of the free atmosphere 52 other than the target gas 51. Within the band pass there is a relatively small degree of spectral overlap between the IR absorption features of the target gas IR absorption spectrum 107 and that of the atmospheric IR absorption spectrum 110.

In a most preferred embodiment of the invention, the method moves to operation 118, which is a further part of determining optimal characteristics for possible IR filters 71. In a general sense, operation 118 involves determining both "similarity" and "contrast" that exist between the respective absorption spectra 107 and 110 of the target gas 51 (the IR filter 71) and that of the atmosphere (i.e., the competitive gases 53). Once values of contrast and similarity are determined, the method moves to an operation 119 in which the difference between the respective values of contrast and similarity is determined for several center wavelengths and bandpasses of possible IR filters 71.

Figure 7:
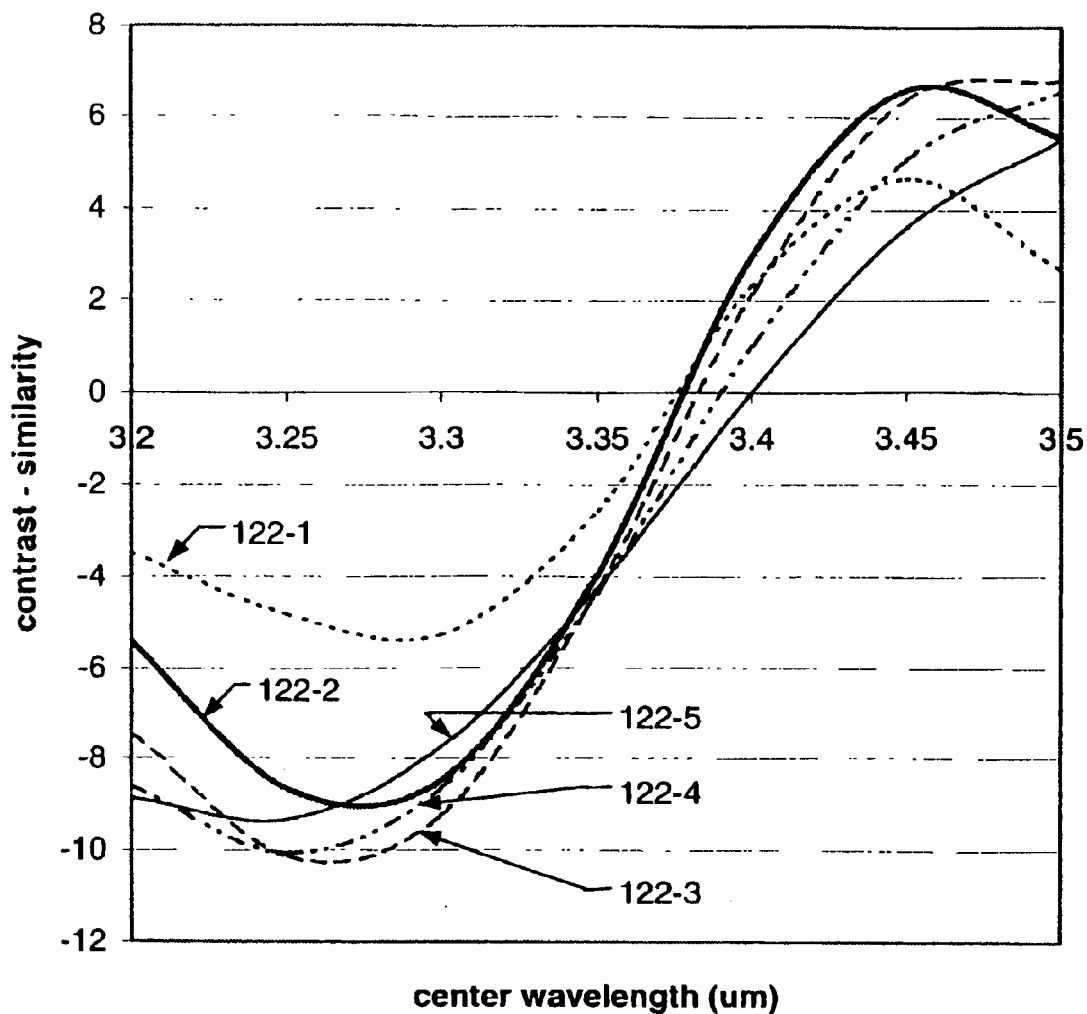
FIG. 7 is a graph illustrating results of an operation of the method of FIGS. 3A and 3B in which, for each of a plurality of potential IR filter bandwidths, a resultant value of the difference between contrast and similarity is plotted as a function of filter center wavelength.
Figure 7:
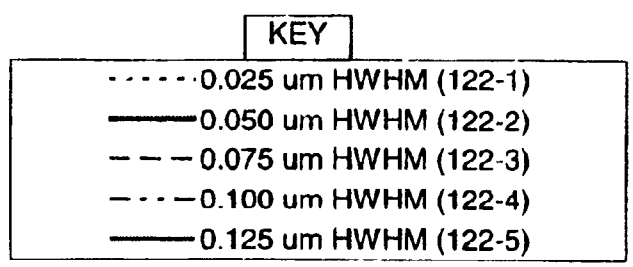

The method moves to an operation 121 (FIG. 3B) in which, for each potential IR filter bandpass, the resultant value of the difference between the contrast and similarity is plotted as a function of filter center wavelength (see FIG. 7). Each filter bandpass is plotted as a separate data set, that is, as a separate curve 122 in FIG. 7. Five exemplary curves 122-1 through 122-5 are shown in FIG. 7, corresponding to five bandwidths identified respectively as 0.025 microns Half Width at Half Maximum ("HWHM"), 0.05 microns HWHM, 0.075 microns HWHM, 0.1 microns HWHM, and 0.125 microns HWHM.

The method moves to an operation 123 in which there is a selection of the combination of filter center wavelength and bandpass that results in the largest value of contrast minus similarity. Such selection provides the optimal IR filter characteristics for the specific trace gas 51, which is methane in the exemplary situation of FIG. 5 which shows the spectrum 107. The curves 122-1, 122-2, and 122-3, for example, provide choices for use in such selection. All curves 122-1 through 122-5 indicate that infrared filters 71 with a center wavelength from 3.2 to approximately 3.37 $\mu$m would not be selected due to poor performance, as indicated by the negative values of contrast minus similarity. That is, the target gas spectrum 107 of FIG. 5 is very similar to the spectrum 110 of competitive gases 53 shown in FIG. 6 within the spectral region between 3.2 to about 3.37 $\mu$m. For infrared filters 71 having a center wavelength between about 3.37 to 3.5 $\mu$m, all curves 122-1 through 122-5 have positive values of contrast minus similarity, indicating an improved degree of contrast between the target gas spectrum 107 shown in FIG. 5 and the spectrum 110 of competitive gases 53 (shown in FIG. 6). Within this improved region from 3.37 to 3.5 $\mu$m, curve 122-5 (corresponding to a filter bandpass of 0.125 am HWHM) provides the poorest system performance since it corresponds to the smallest value of contrast minus similarity. Alternately, curve 122-3 achieves a higher peak value of contrast minus similarity, at the center wavelength of approximately 3.45 $\mu$m. Also, two filter bandpasses (curves 122-2 and 122-3) result in equivalent values of contrast minus similarity (see HWHM of respective 0.05 μm and 0.075 μm). Therefore, these two infrared filters 71 corresponding to curves 122-2 and 122-3 will provide equivalent performance for detecting only the target gas 51 of interest (methane in this example) while rejecting light 58 having wavelengths corresponding to the strong absorption bands of all competitive gases 53. Since the filter bandwidth of curve 122-3 is wider (0.075 μm HWHM), an IR filter 71 having such center wavelength (about 3.45 μm) and bandwidth (0.075 μm HWHM) will transmit a larger signal amplitude of the light 67 to the detectors 82 and 86 than will an IR filter 71 based on curve 122-2 (0.05 μm HWHM).

Having the curves 122-1 through 122-5, for example, certain additional considerations may be reviewed in selecting the optimal center wavelength and optimal bandpass, such as manufacturability of the IR filter 71. An IR filter 71 having a very narrow center wavelength (e.g., less than 0.5 μm) in the visible range (300 to 800 nm) may be manufactured more easily and at less cost than such IR filter 71 in the infrared or ultraviolet range. Also, consideration may be given to the breadth of the optimal bandpass, which may influence manufacturability and cost to manufacture, especially with respect to the particular center wavelength of the IR filter 71.

More preferably, the selection of the optimal center wavelength and optimal bandwidth may be made according to which combination of center wavelength and bandpass results in the largest value of contrast minus similarity for the trace gas 51. For example, a center wavelength of approximately 3.45 μm and the either the 0.05 or 0.075 μm bandpass of curves 122-2 or 122-3, respectively, may be considered as the optimal center wavelength and optimal bandpass. Having made the selection of the optimal center wavelength and optimal bandpass, the method is DONE.

In view of this method, for example, when the GCR subsystem 74 is configured with the IR filter 71 to respond to light 67 transmitted through the detection path 59, the subsystem 74 (with the IR filter 71) is configured to respond to light wavelengths within a band in which there is a high degree of dissimilarity in the atmospheric infrared absorption spectra. The dissimilarity is indicated by wavelengths at which there is high (or strong) infrared absorption by the target gas 51 and low (or weak) infrared absorption by the competitive gas 53.

Figure 8:
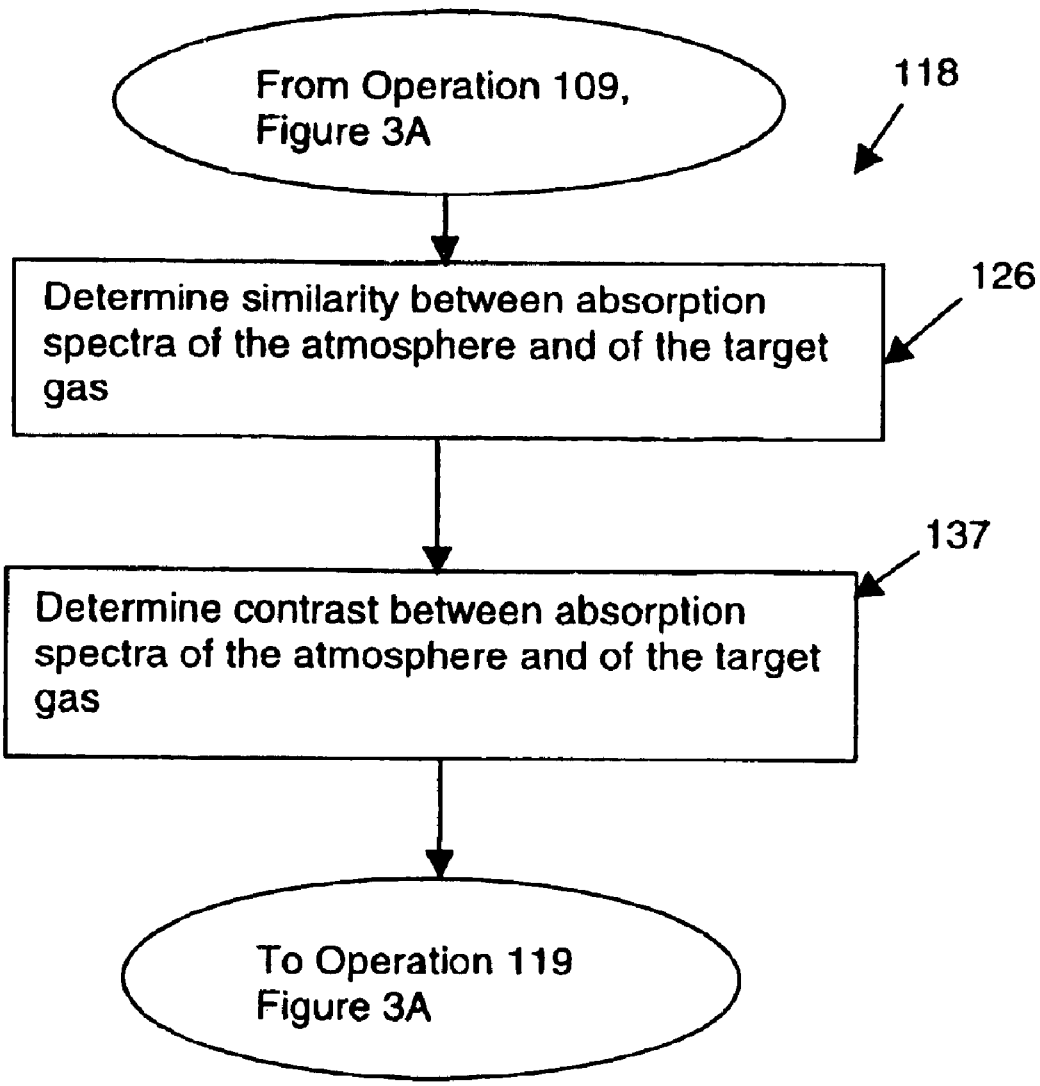
FIG. 8 is a flow chart illustrating suboperations of an operation of the method of FIGS. 3A and 3B for determining similarity and contrast.

FIG. 8 shows in more detail suboperations of operation 118, which involves a suboperation 126 for determining similarity, which is defined, in general, as those spectral regions where both the target gas 51 (represented by tie spectrum 107, FIG. 5) and the atmosphere (represented by the spectrum 110, FIG. 6), possess the overlapping absorption features, i.e., the absorption lines 108D and 17D.

In more detail, suboperation 126 may involve determining a set of similarity data as a function of overlap regions 56 (FIGS. 2A and 2B) within the spectral regions shown in FIGS. 2A and 2B (see absorption spectra 54C and 54T). In FIGS. 5 and 6 the overlap regions may correspond to highly absorbing IR absorption lines 108D and 117D for each of respective competitive gas 53 and target gas 51, and are those regions within the spectral region in which the respective IR absorption spectra 107 and 110 of both the target gas 51 and at least one other competitive gas 53 have absorption characteristics. The set of similarity data includes a plurality of data items (i.e., points on such graphs) within each of a plurality of bandpasses that include such highly absorbing lines 108D and 117D. One of the data items corresponds to the center wavelength within each bandpass.

In still more detail, a similarity determination involves calculating the product of the atmospheric IR absorption (1 minus transmission T) and the target gas cell IR absorption on a wavelength-by-wavelength basis. That is, a change (delta) in similarity is determined by:

$$\partial similarity = T_{filter}(1-T_{atmosphere})(1-T_{cell})\partial \lambda, \quad \text{Equation (3)}$$

where $T_{atmosphere}$ is the wavelength-dependent optical transmission through the atmosphere (such as shown in FIG. 6), $T_{cell}$ is the wavelength-dependent optical transmission through the target gas channel 78 of the GCR subsystem 74 (such as that shown in FIG. 5 for the case of methane), $T_{filter}$ is the wavelength-dependent optical transmission through the IR filter 71, and delta lambda is an increment of wavelength within the bandwidth of the IR filter 71.

An exemplary first operation in the calculation of Equation 3 is to perform a product of absorptions, as follows:

$$\text{Product} = (1-T_{atmosphere})(1-T_{cell}). \quad \text{Equation (4)}$$

Figure 9:
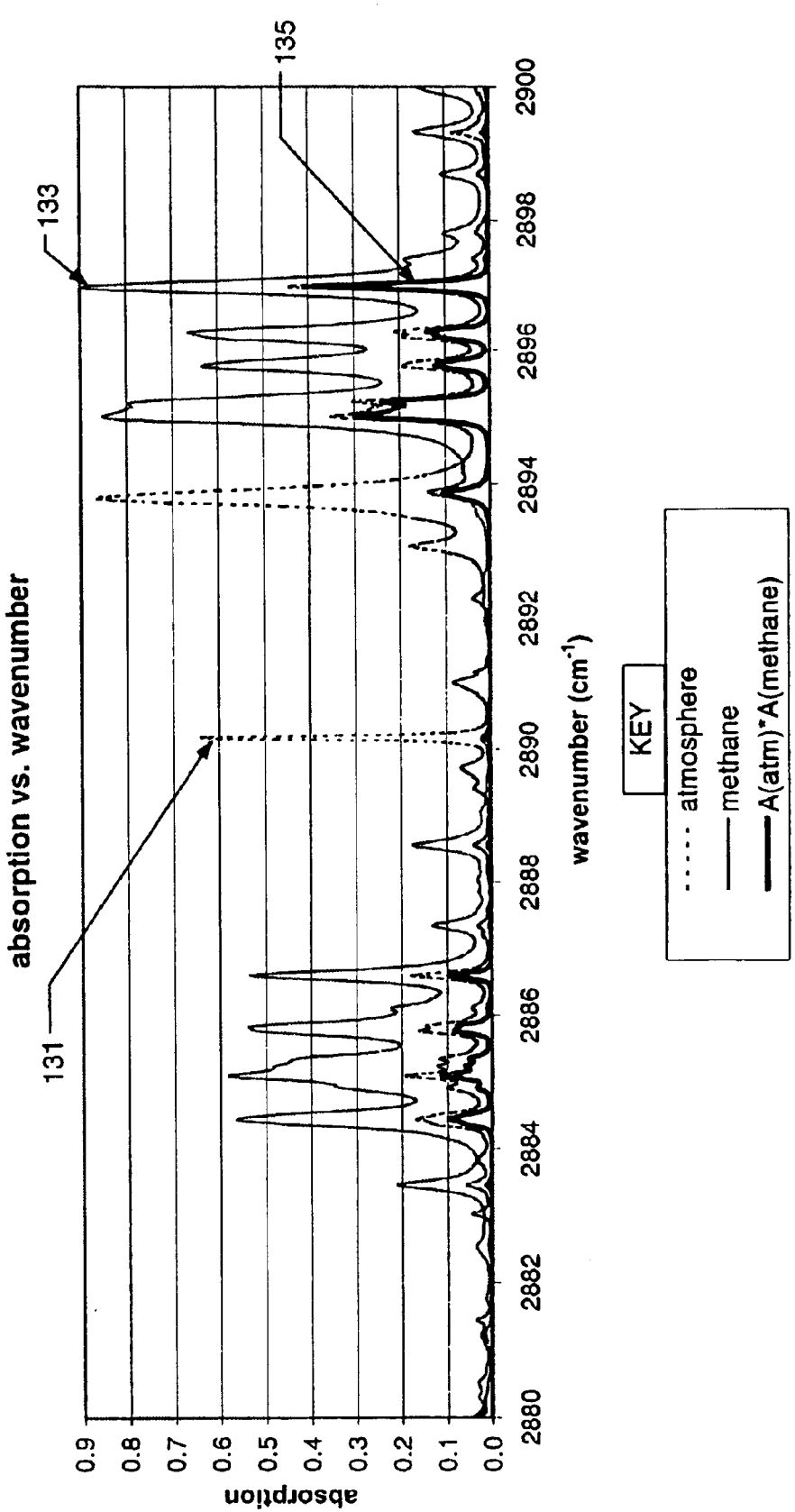
FIG. 9 is a graph illustrating a sub-set of a spectral region of interest in which three absorption curves represent atmospheric absorption in that spectral region, and absorption by a target gas in that spectral region, and the product of the absorptions of the atmosphere and methane as the target gas.

FIG. 9 illustrates a sub-set of the spectral region of interest (e.g., shows wavenumbers 2880 through 2900 cm$^{-1}$) and shows three absorption curves 131, 133, and 135. Curve 131 represents the atmospheric absorption in that spectral region, curve 133 represents the absorption by the target gas 51 in that spectral region, and curve 135 represents the product of the absorptions of curves 131 and 133 for methane as the target gas 51. FIG. 9 shows the spectral regions where the spectrum 110 of the competitive gas 53 (the atmosphere in this case) and the spectrum 107 of the target gas 51 (methane in this example) are similar, or well correlated. A high degree of similarity between these spectra results in a GCR that cannot distinguish between the competitive gas species and the target gas of interest.

To obtain similarity, in operation 126 Equation 3 is computed as follows:

$$similarity \equiv \int_{\lambda_1}^{\lambda_2} T_{filter}(1-T_{atmosphere})(1-T_{cell})\partial \lambda, \quad \text{Equation (5)}$$

where $\lambda_1$ and $\lambda_2$ denote the bandwidth B of the IR filter 71. Operation 126 multiplies the absorption product by the filter transmission profile $T_{filter}$ and an integration is performed over the filter bandwidth $\lambda_2$ to $\lambda_1$.

Still referring to FIG. 8, upon conclusion of the suboperation 126 of operation 118, the method moves to a suboperation 137 for the determination of contrast. Contrast is defined, in general, as those spectral regions where the target gas 51 (represented by the spectrum 107, FIG. 5) has deep absorption features 108D, and the atmosphere (represented by the spectrum 110, FIG. 6), possesses the weak absorption features, i.e., the absorption lines 117W. Thus, the determination of spectral contrast is based on the regions of non-overlapping absorption between the atmospheric spectrum 110 and the spectrum 107 of the target gas 51.

In a general sense, operation 137 may involve determining a set of contrast data as a function of respective non-overlap regions 108D and 117W within the spectral regions of respective FIGS. 5 and 6. The non-overlap regions 117W and 108D are for each of the respective competitive gas 53 and target gas 51 and are those regions within the spectral region in which the target gas absorption spectrum 107 has the high absorption characteristics (lines 108D) but the competitive gas absorption spectrum 110 has the low absorption characteristics (117W). The set of contrast data includes a data item corresponding to each of many possible the bandpasses and center wavelengths of the infrared filter 71.

In more detail, the contrast determination of suboperation 137 involves calculating the product of the atmospheric transmission T and the target gas cell absorption on a wavelength-by-wavelength basis. That is, a change (delta) in contrast is determined by:

$$\partial contrast = T_{filter}(T_{atmosphere})(1-T_{cell})\partial\lambda. \qquad \text{Equation (6)}$$

Figure 10:
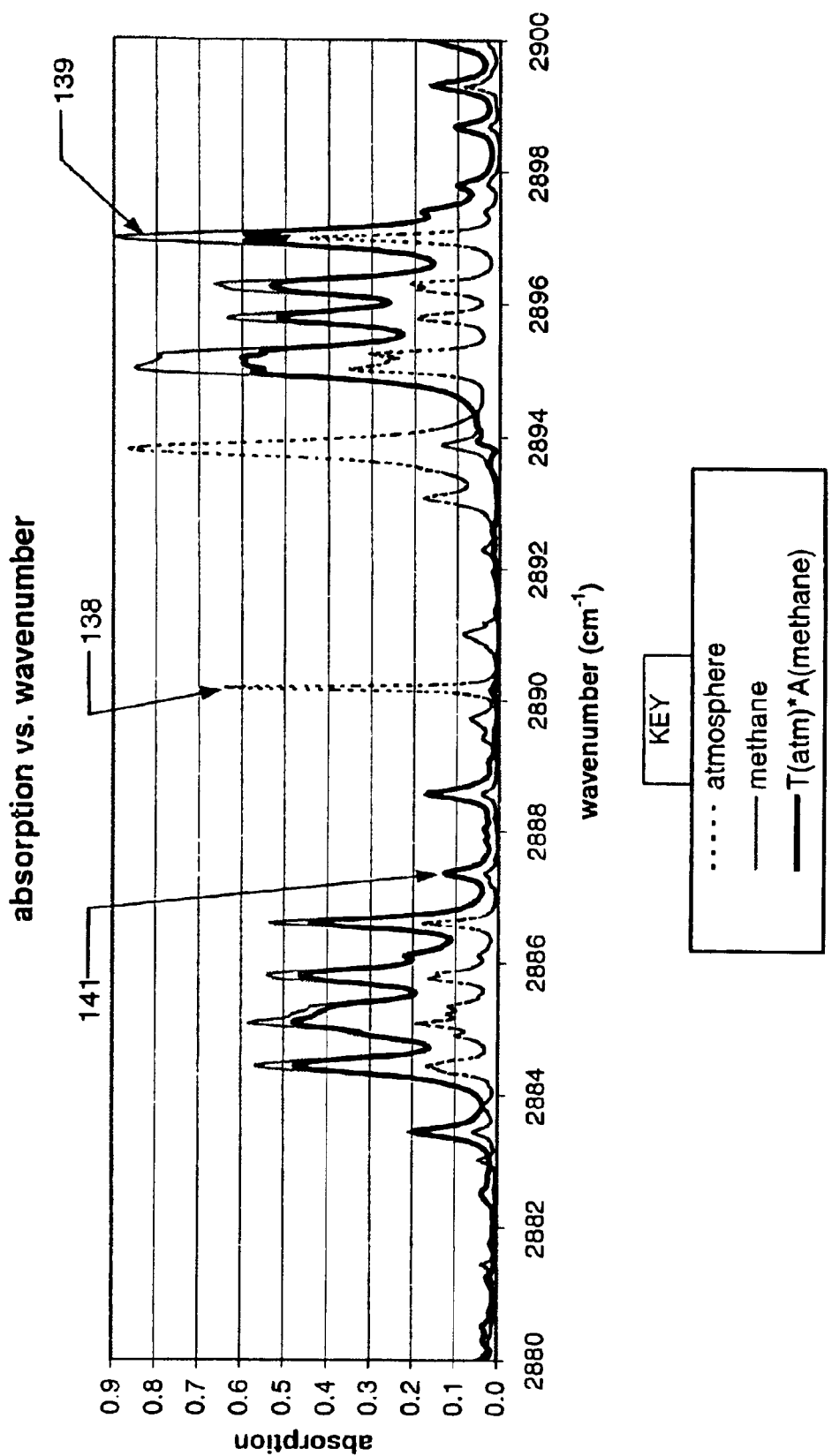
FIG. 10 is a graph illustrating a sub-set of a spectral region of interest in which curves represent atmospheric absorption in that spectral region, and absorption by a target gas in that spectral region, and the product of the atmospheric transmission and absorption of methane as the target gas.

An exemplary first operation in the calculation of Equation 6 is to perform another product of atmospheric transmission and target gas absorption per Equation (7):

$$Product = (T_{atmosphere})(1-T_{cell}); \qquad \text{Equation (7)}$$

where: ($T_{atmosphere}$)=atmospheric transmission and ($1-T_{cell}$)=target gas absorption. FIG. 10 illustrates a sub-set of the spectral region of interest (e.g., shows wavenumbers 2880 through 2900 cm$^{-1}$) and shows three absorption curves 138, 139, and 141. Curve 138 represents the atmospheric transmission in that region, curve 139 represents the absorption by the target gas 51 (methane) in that region, and curve 141 represents the product of the respective transmission of curve 138 and absorption of curve 139 for methane as the target gas 51. FIG. 10 shows the spectral regions where the spectrum 110 of the competitive gas 53 (the atmosphere in this case) and the spectrum 107 of the target gas 53 (methane in this example) are dissimilar, or not well correlated. A high degree of dissimilarity (or contrast) between these respective spectra 107 and 110 results in operation of the GCR subsystem 74 that effectively distinguishes between the competitive gas 53 and the target gas 51 of interest.

To obtain a value of contrast, in operation 137 Equation 6 is computed:

$$contrast \equiv \int_{\lambda_1}^{\lambda_2} T_{filter}(T_{atmosphere})(1 - T_{cell})\partial\lambda. \qquad \text{Equation (8)}$$

Having obtained the value of contrast in suboperation 137, the method moves to operation 119 (FIG. 3A).

Figure 11:
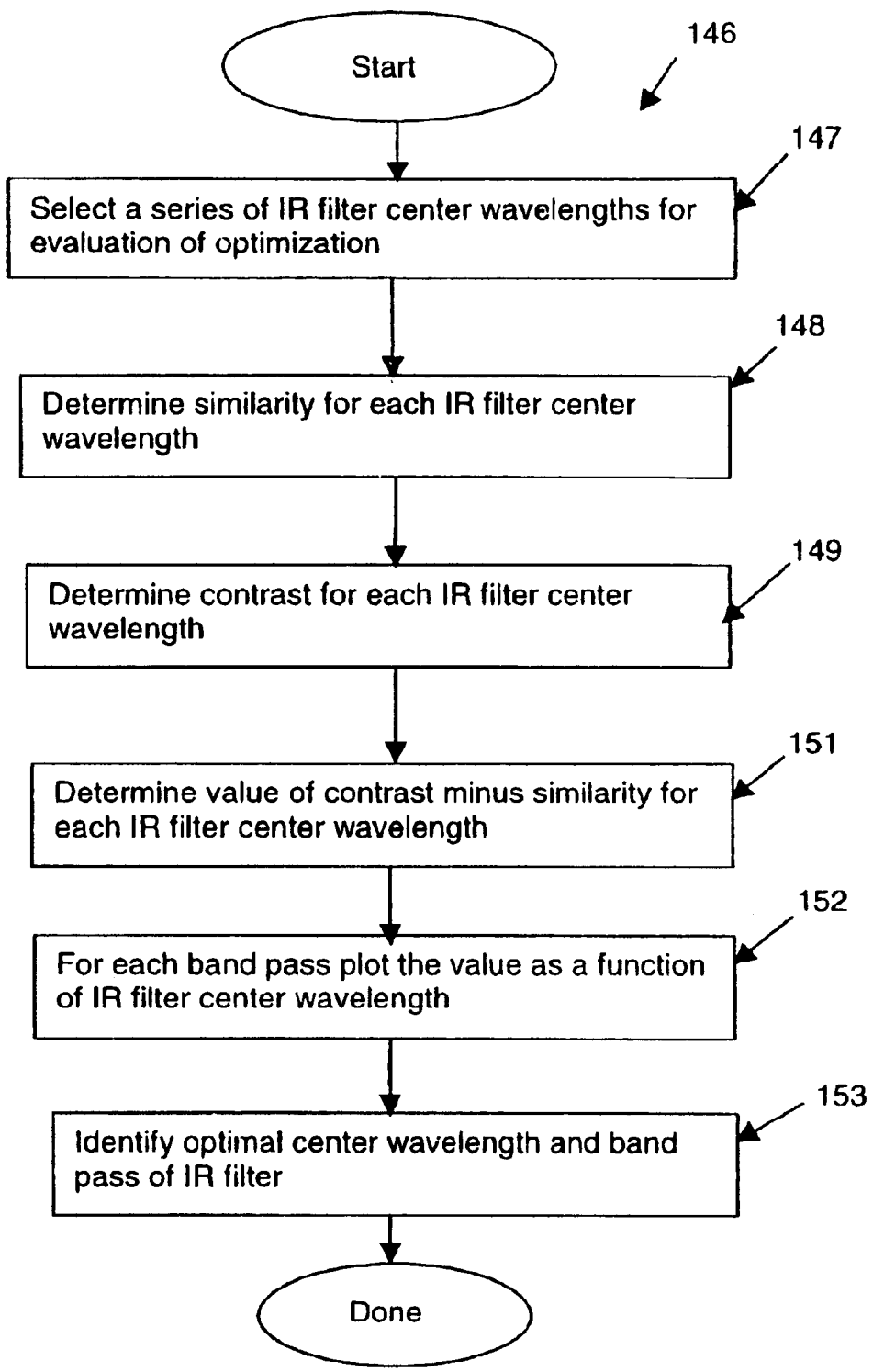
FIG. 11 is a flow chart illustrating other aspects of the method of optimization of characteristics of an IR filter.

In summary, referring to FIG. 11, a method of optimization of the characteristics of the IR filter 71 may be described by a flow chart 146 in which an operation 147 selects the series of IR filter center wavelengths for evaluation (described in more detail in reference to operations 102 and 109 of FIG. 3A). The method moves to operation 148 for determining the similarity for each such IR filter center wavelength and bandpass selected in operations 146, as described in operation 118 (FIG. 3A) and 126 (FIG. 8). The method moves to operation 149 for determining the contrast for each such IR filter center wavelength and bandpass selected in operation 147, as described in operations 118, and 137 (FIG. 8). The method moves to operation 151 for determining the value of contrast minus similarity for each of the IR filter center wavelength and bandpass options identified in operation 147, as described with respect to operation 119. The method moves to operation 152 in which the value of contrast minus similarity is plotted for each of the filter center wavelength and bandwidth options identified in operation 147, the plotting being as a function of filter center wavelength. The plotting provides a separate one of the curves 122 for each IR filter bandpass. The method moves to operation 153 for identifying the optimal center wavelength and optimal bandpass that provides the largest value of contrast minus similarity for the trace gas 51, as described with respect to operation 123 (FIG. 3B).

The optimal center wavelength and optimal bandpass are used to provide the IR filter 71 in the system 50 to optimize the response of the GCR subsystem 74 to a trace amount of a target gas 71 that may be present in the free atmosphere 52 along the detection path 59 to the receiver 68. The detection path 59 may also contain the competitive gas 53 the presence of which in the free atmosphere 52 may interfere with detection of the trace amount of the target gas 51. Based on the IR filter 71 used with the GCR subsystem 74, the GCR subsystem 74 is configured to respond to the light 58 transmitted along the detection path 59 and having a wavelength within the optimal bandpass. The optimal bandpass generally corresponds to strong absorption by the at least one target gas 51 and corresponds to weak absorption by the gases 53 present in the free atmosphere 52 as compared to the strong IR absorption by the target gas 51.

In one embodiment of the system 50, an exemplary IR filter 71 of the receiver 68 may be provided with respect to one competitive gas 53, such as water vapor which is a widely occurring gas. In this case, the absorption spectrum 110 may correspond to water vapor. In another embodiment of the system 50, another exemplary IR filter 71 of the receiver 68 may be provided with respect to competitive gas 53 in the form of water vapor and another non-target gas 53. In this case, the absorption spectrum 110 may correspond to water vapor and the other gas 53.

Figure 12:
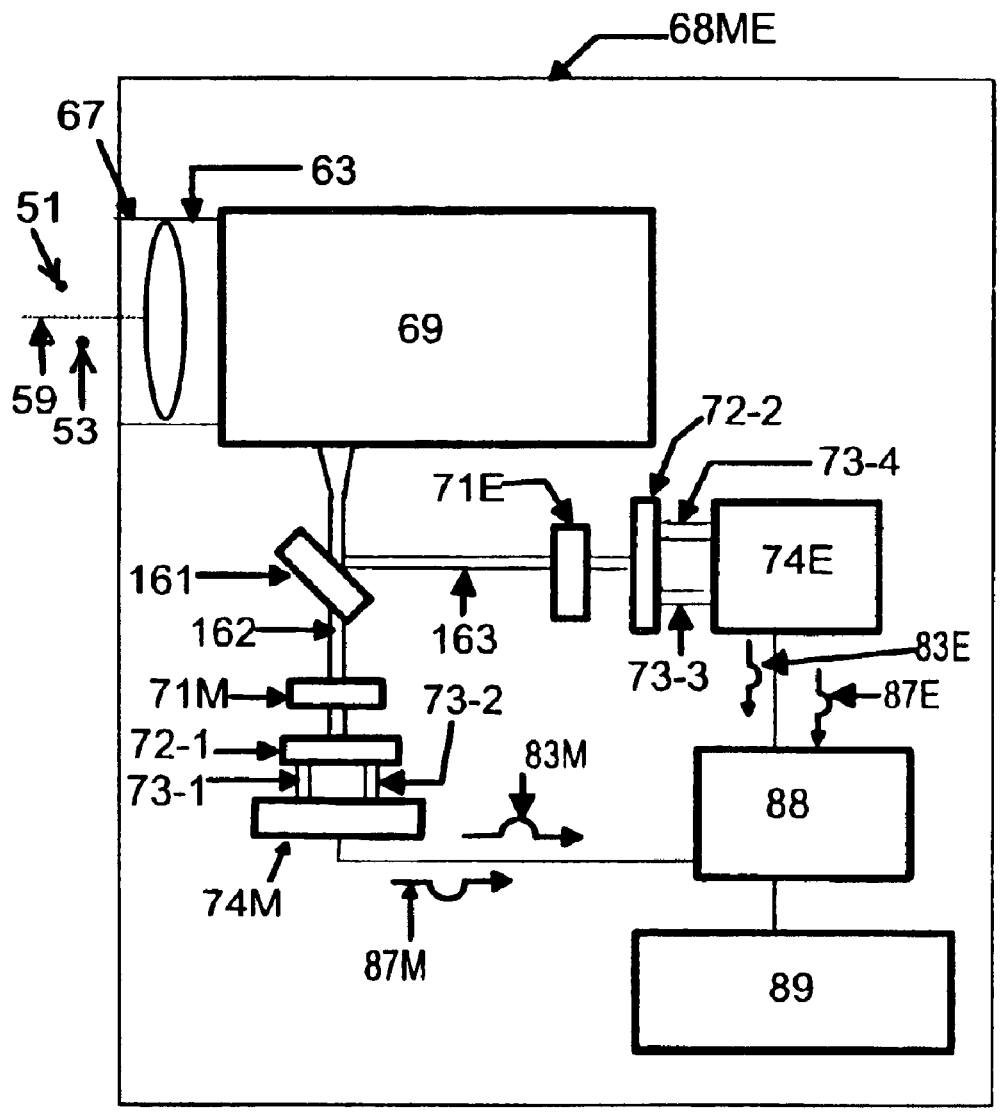
FIG. 12 is a schematic diagram of a system of the present invention configured to detect and distinguish between natural gas as a target gas and other combustible gases as competitive gases.

FIG. 12 shows another embodiment of the system 50 which is configured to detect and distinguish between natural gas as a target gas 51, and other combustible gases as competitive gases 53. As described above, the main constituents of natural gas are methane and ethane. This embodiment of the system 50 may be configured as an optimal natural gas detector by being configured to simultaneously detect both methane and ethane to assure that the detected gas is from a natural gas leak and not from a natural emission source. FIG. 12 shows the receiver 68 portion of the system 50 as a methane/ethane receiver 68ME provided with the receiving telescope 69 which directs a portion of the light beam 67 from the far end 63 to a second beam splitter 161. The light beam 67 is divided into two separate and simultaneous beams 162 and 163 which are respectively directed through two separate IR filters 71M and 71E.

An embodiment of the IR filter 71M may be configured to transmit light 58 from the light beam 67 that was transmitted along the detection path 59 and having a wavenumber within a band taken from the group consisting of: from about 1200 to about 1400 cm$^{-1}$, from about 2800 to about 3200 cm$^{-1}$, from about 2850 to about 3000 cm$^{-1}$, and from about 3000 to about 3200 cm$^{-1}$. These wavenumber bands are preferred wavenumber bands for methane as a target gas 51. More preferrably, an embodiment of the IR filter 71M may be configured to transmit light 58 from the light beam 67 that was transmitted along the detection path 59 and having a wavenumber within a band taken from the group consisting of: from about 2850 to about 3000 cm$^{-1}$, and from about 3000 to about 3200 cm$^{-1}$. These wavenumber bands are more preferred wavenumber bands for methane as a target gas 51. Most preferrably, an embodiment of the IR filter 71M may be configured in the manner described above with respect to FIGS. 3A and 3B through 11 with a methane-optimal central wavelength and a methane-optimal bandpass to provide substantially increased sensitivity to methane as the target gas 51 and substantially increased selectivity of methane to avoid erroneous detection of any competitive gas 53 as methane. The particular methane-optimal center wavelength and methane-optimal bandpass resulting from use of the methods described with respect to FIGS. 3A and 3B through 11 will depend on the field conditions described above, for example.

An embodiment of the IR filter 71E may be configured to transmit light 58 from the light beam 67 that was transmitted along the detection path 59 and having a wavenumber within a band of from about 2970 to 3005 cm$^{-1}$. More preferably, an embodiment of the IR filter 71E may be configured with an ethane-optimized central wavelength and an ethane-optimized bandpass in such manner described above to provide substantially increased sensitivity to ethane as the target gas 51 and substantially increased selectivity of ethane to avoid erroneous detection of any competitive gas 53 as ethane. Most preferably, an embodiment of the IR filter 71M may be configured in the manner described above with respect to FIGS. 3A and 3B through 11 with an ethane-optimal central wavelength and an ethane-optimal bandpass to provide substantially increased sensitivity to ethane as the target gas 51 and substantially increased selectivity of ethane to avoid erroneous detection of any competitive gas 53 as ethane. The particular ethane-optimal center wavelength and optimal ethane-bandpass resulting from use of the methods described with respect to FIGS. 3A and 3B through 11 will depend on the field conditions described above, for example.

The receiver 68ME is configured so that the IR filter 71M transmits the light beam 162 having, for example, the methane-optimal central wavelength and the methane-optimal bandpass. The light beam 162 is transmitted to a methane-ethane embodiment of the beam splitter 72. The beam splitter 72 is configured in two parts 72-1 and 72-2. Each part provides two split light beams 73, including one set of split beams 73-1 and 73-2, and another set of split light beams 73-3 and 73-4, that are transmitted respectively and simultaneously to, and simultaneously enter, one of two of the dual channel gas correlation radiometer (GCR) subsystems 74. One subsystem 74M for methane detection receives the beams 73-1 and 73-2; and one subsystem 74E for ethane detection receives the beams 73-3 and 73-4. Each respective subsystem 74M and 74E is configured in the manner described above with respect to FIG. 1A with two separate channels 76 and 78 that simultaneously receive the respective split light beams 73. Referring to FIG. 1A for the details of the respective subsystems 74M and 74E, the first channel 76 of the methane subsystem 74M is configured with the first detector 82 that outputs blank channel data 83 (referred to here as 83M, for methane) that varies according to whether there is methane 51 in the detection path 59 through which the light beam 67 was transmitted on the way to the receiver 68ME. A second of the beams 73-2 is transmitted through the second channel 78 of the methane subsystem 74M, which is configured with a methane target gas cell 84. The second channel 78 is configured with the second detector 86 which outputs target gas channel data 87 (referred to here as 87M, for methane) that is independent of whether there is methane target gas 51 in the region, i.e. along the detection path 59 through which the light beam 67 was transmitted on the way to the receiver 68ME. The blank channel data 83M and the target channel data 87M are supplied from the methane subsystem 74M to the lock-in amplifier 88, the output of which is applied to the display and data processor 89.

The first channel 76 of the ethane subsystem 74E is configured with a first detector 82 that outputs blank channel data 83 (referred to here as 83E, for ethane) that varies according to whether there is ethane 51 in the detection path 59 through which the light beam 67 was transmitted on the way to the receiver 68. The second channel 78 of the ethane subsystem 74E is configured with a second detector 86 which outputs target gas channel data 87 (referred to here as 87E, for ethane) that is independent of whether there is ethane target gas 51 in the region, i.e. along the detection path 59 through which the light beam 67 was transmitted on the way to the receiver 68. The blank channel data 83E and the target channel data 87E are supplied from the ethane subsystem 74E to the lock-in amplifier 88, the output of which is applied to the display and data processor 89. It may be understood that the splitting of the light beam 67 in this manner by the beam splitter 161 results in the simultaneous reception by the processor 89 of the data 83M, 83E, 87M and 87E for simultaneous processing to simultaneously detect the occurrence of both methane and ethane to assure that the detected gas 51 is from a natural gas leak and not from a natural emission source.

It may be understood that the features of the embodiment 50-1 of the system 50 may be adapted for separate, non-simultaneous detection of ethane and methane as the target gas 51. For example, when conditions of the free atmosphere 52 are stable (relatively invariable as to atmospheric turbulence, etc.), one system 50 (as shown in FIG. 1A or in FIG. 18 as described below) may be provided to detect ethane as a target gas 51 and another such system 50 may be provided to detect methane as a target gas 51. The detection paths 59 of each such system 50 may be close to each other (e.g., within a few inches or a foot). Alternatively, in the system 50 of FIG. 1A one dual channel GCR subsystem 74 may be provided to detect ethane and an additional dual channel GCR subsystem 74 may be combined with the ethane system 50 to detect methane. For example, the beam splitter 72 may be movable to direct the two beams 73-1 and 73-2 first into the ethane subsystem 74 and then into the methane subsystem 74.

As described above with respect to FIGS. 1A and 1B, the modulated collimated light beam 67 has been subjected to the atmospheric conditions along the detection path 59 (e.g., at the successive moments of time t1, t2, t3, etc.) during which the light beam 67 is transmitted from the near end 62 to the far end 63 of the detection path 59. Such atmospheric conditions further modulate the light beam 67, but this further atmospheric modulation is different from the modulation by the modulator 64. The lock-in amplifier 88 selects from this combination of modulated light 58 only the light having the modulation imposed by the modulator 64, such that the data 83 and 87 do not include the effects of atmospheric turbulence, jitter, beam wander, or changes in the index of refraction, for example. Thus, each item of the data 83 and 87 received by the processor 89 at any moment of time represents the influence of the same current atmospheric conditions of the free atmosphere 52 as the light 58 is transmitted along the detection path 59, as may have been modified only by transmission through the respective channels 76 and 78. As described above, the first detector 82 outputs the blank channel data 83 that varies according to whether there is target gas 51 in the detection path 59 through which the light beam 67 was transmitted on the way to the receiver 68. The second detector 86 outputs target gas channel data 87 that is independent of whether there is target gas 51 in the region, i.e. along the detection path 59 through which the light beam 67 was transmitted on the way to the receiver 68. The channels 76 and 78 thus modify the light beam 67 so that together the data 83 and 87 may be processed by the processor 89 to indicate, for example, whether or not there was target gas 51 along the detection path 59 during the successive moments of time during which the light beam 67 was transmitted from the near end 62 to the far end 63 along the detection path 59.

The lock-in amplifier 88 is configured in two parts, one for the first channel 76 and one for the second channel 78. Referring now to FIG. 13, and considering the lock-in amplifier 88-1 for the first channel 76 as an example of the structure and operation for both channels 76 and 78, a crystal oscillator and phase lock-loop circuit 171-1 locks to the frequency and phase of an input in the form of the blank channel data (or signal) 83 from the first channel 76. The crystal oscillator and lock-in circuit 171-1 generates an output 173 modulated at the appropriate frequency. The output 173 is delivered to a mixer 176. In addition, the lock-in amplifier 88-1 accepts a selectable input 172 from either the user (from knowledge of the approximate source modulation frequency) or from the source modulation reference signal 97 (FIG. 1B). A phase-lock-loop circuit 174-1 of the amplifier 88-1 tunes the frequency of an output 175-1 to that of the selectable input 172. A phase shifting circuit 174-2 within the amplifier 88-1 adjusts the electronic phase of the signal 175-1 from the phase lock loop circuit 174-1. An output 175-2 from the phase shifting circuit 174-2 is then provided to the mixer 176. The mixer 176 within the amplifier 88-1 produces the sum and difference frequencies of inputs to the mixer 176 (i.e., outputs 173 and 175-2). An output 177 from the mixer 176 is passed through a low pass filter 178 to remove the sum of the frequencies contained in the signals 175-2 and 173 and thereby passing only the difference frequencies. Finally, the signal 177 that passes through the low pass filter 178 is amplified by an amplifier 178-1, resulting in a lock-in output signal 179. Thus, the amplified signal 179 is proportional to the magnitude of the signal 83 from the blank channel 76 that is at the same frequency as the selectable input 172. The signal 179 is input to the processor 89. Minor changes to the selectable input 172 frequency may be performed under microprocessor control in order to maximize the output signal 179 by varying the phase lock loop 174-1 frequency via control line 180. Phase adjustments may also be performed under microprocessor control in order to maximize the output signal 179. A signal proportional to the phase adjustment performed by the microprocessor may be obtained at output 181. Thus, the lock-in amplifier 88-1 outputs a signal 181 representing the phase and the signal 179 representing the magnitude of the blank channel signal 83 relative to the internal reference. Given this measured phase and magnitude of the blank channel signal 83, the lock-in amplifier 88-1 precisely electronically locks to the phase and frequency of the blank channel signal 83. In a similar manner, the lock-in amplifier 88 for the first channel 78 measures the phase and magnitude of the target channel data 87 and precisely electronically locks to the phase and frequency of the target channel data 87. In this manner, (including when the source modulation reference signal 97, FIGS. 1B, 17, and 18) cannot be used to provide the needed phase and frequency) the modulation of the light 58 at the source 61 enables the modulated light beam 67, itself, via the blank channel data 83 which was derived from the light beam 67, to provide the required phase and frequency to the lock-in amplifier 88 of the receiver 68. In turn, this eliminates the need to extend cabling, or hard wire, between the modulator 64 at the source 61 and the receiver 68. Further, the provision of the lock-in amplifier 88 in the receiver 68, in conjunction with the configuration of the dual channel GCR subsystem 74 for simultaneous channel operation, effectively eliminates from the first and second channel data 83 and 87 the effects on the light beam 67 of atmospheric turbulence, beam wander and drift, source illumination variations, etc. In attempts by other than the present invention to detect target gases 51, these atmospheric and systematic effects often dominate the target gas measurement uncertainty. Thus, the above-described configurations of the source 61 with the modulator 64, and of the receiver 68 with the lock-in amplifier 88, and of the GCR subsystem 74, greatly improve the detectable concentration achievable by the system 50, which may be reduced to the above-described few PPB for ethane detection, for example.

As described above, the data 83 and 87 from the respective blank and target gas channels 76 and 78 are input to the processor 89. The processor 89 is programmed to perform operations of measurement techniques to further reduce the impact of competitive gases 53 on the minimum detectable concentration achievable by the system 50. The programmed operations of the measurement techniques also reduce the impact of broadband scattering, such as produced by aerosols, along the detection path 59. These programmed operations involve measuring a value of a "null" signal under similar atmospheric conditions as exist during the detection and measurement of the concentration of the trace gas 51.

Figure 14:
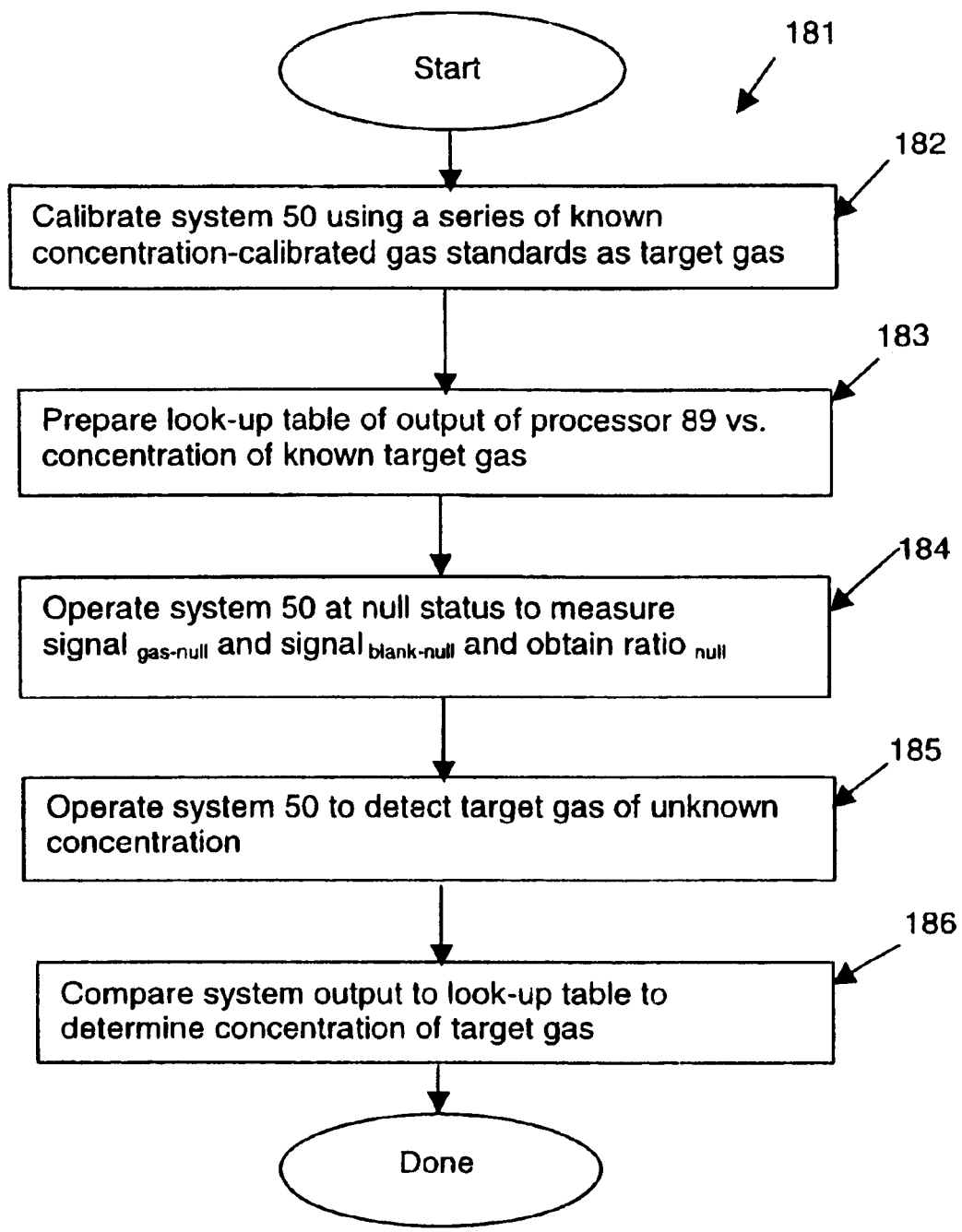
FIG. 14 depicts a flow chart illustrating a method of processing a target gas measurement technique, which relates to a ratio of measured data to null data.

FIG. 14 shows a flow chart 181 having operations of a method of the invention for performing such a measurement technique. The method relates to Equation (1), which may be described in more detail as the following ratio:

$$Output = \frac{Ratio_{measured}}{Ratio_{null}} - 1 = \frac{\left(\frac{Signal_{gas}}{Signal_{blank}}\right)}{\left(\frac{Signal_{gas-null}}{Signal_{blank-null}}\right)} - 1 \qquad \text{Equation (9):}$$

where Output represents the output of the processor 89. In the ratio of Equation (9), $Signal_{gas}$ is the amplitude of the output of the detector 86 (which is the target gas data 87) measured through the gas channel 78, and $Signal_{blank}$ is the amplitude of the output of the detector 82 (which is the blank channel data 83) measured through the blank channel 76. $Ratio_{measured}$ is the ratio formed by dividing $Signal_{gas}$ by $Signal_{blank}$. $Ratio_{null}$ is determined by removing the target gas cell 84 and the blank cell 81 from the respective channels 78 and 76. Under this modified channel configuration, $Signal_{gas-null}$ is the amplitude of the output of the detector 86 (the target gas data 87) measured through the gas channel 78, and $Signal_{blank-null}$ is the amplitude of the output of the detector 82 (the blank channel data 83) measured through the blank channel 76. $Ratio_{null}$ is then calculated as the ratio of these two values. Thus, $Ratio_{null}$ is based on the differences in the optical and electronic responses of the structural elements of the respective blank and target gas channels 76 and 78. Such elements include optics, the detector 86, and typical preamplifier and post-amplifier circuits and analog-to-digital converters (not shown). Each of the blank channel data 83 and target gas channel data 87 is in this manner determined relative to such null value.

The method of the invention shown in FIG. 14 may start by moving to an operation 182 in which calibration of the system 50 is performed to obtain the above Output. In detail, in operation 182 the Equation (9) Output, i.e., the ($Ratio_{measured}/Ratio_{null}$)−1, is determined by operating the system 50 using a series of known, concentration-calibrated gas standards as the target gas 51. Preferably, such calibration of the system 50 may be performed once the system 50 is placed at a particular detection path 59 just prior to detection of an unknown target gas 51. More preferably, such calibration may be performed at the factory as a step in the manufacture of a unit embodying the principles of the system 50.

The method moves to an operation 183 in which a look-up table is created from the above Output. For each known target gas 51, the look-up table lists the Output of the system 50 and corresponding values of the concentration of the known target gas 51 in terms of the units of "concentration× pathlength" (PPM-m or PPB-m).

The method moves to operation 184 in which the system 50 is operated at null status to measure $Signal_{gas-null}$ and $Signal_{blank-null}$ and obtain $Ratio_{null}$. Operation 184 of the method of flow chart 181 is shown in more detail with reference to FIG. 15A. Operation 184 includes a suboperation 192 in which the first and second channels 76 and 78 are modified to null status and a null-calibration is performed. Such modification is performed by removing the target gas cell 84 from the second channel 78 and the blank cell 81 from the first channel 76. Also, the system 50 is placed so as to define a particular detection path 59, and the housings 91 and 92 are aligned so that the light beam 67 is accurately centered as it is received by the receiving telescope 69. Such place may be fixed, e.g., on the ground or on a mobile platform (e.g., on a vehicle described below).

The method moves to suboperation 193 in which light 67 is directed through these modified configurations of the channels 76 and 78, to obtain a value of respective $Signal_{gas-null}$ based on the amplitude of the output of the detector 86 (the target gas data 87) measured through the gas channel 78, and a value of $Signal_{blank-null}$ based on the amplitude of the output of the detector 82 (the blank channel data 83) measured through the blank channel 76. The method moves to an operation 194 in which a value of $Ratio_{null}$ is then calculated as the ratio of these two values $Signal_{gas-null}$ and $Signal_{blank-null}$. The method moves to a suboperation 195 in which the system 50 is returned to operational status with no such bypasses. The method moves to operation 185 (FIG. 14).

In operation 185 the system 50 is operated to detect the target gas 51 of unknown concentration. In preparation for this operation, the target gas cell 84 is configured for detecting such particular target gas 51. Also, the system 50 remains placed so as to define the particular detection path 59, and the housings 91 and 92 remain aligned so that the light beam 67 is accurately centered as it is received by the receiving telescope 69. The system 50 is operated and the Output of the processor 89 is obtained.

The method moves to an operation 186 in which this processor Output of the system 50 is compared to the data in the look-up table. For example, the Output of the system 50 is used to find the value of the concentration of the known target gas 51 that corresponds to the Output. This value found in the look-up table is the concentration of the target gas 51 of unknown concentration expressed in terms of "concentration×pathlength" (PPM-m or PPB-m). The method is DONE.

Figure 15A:
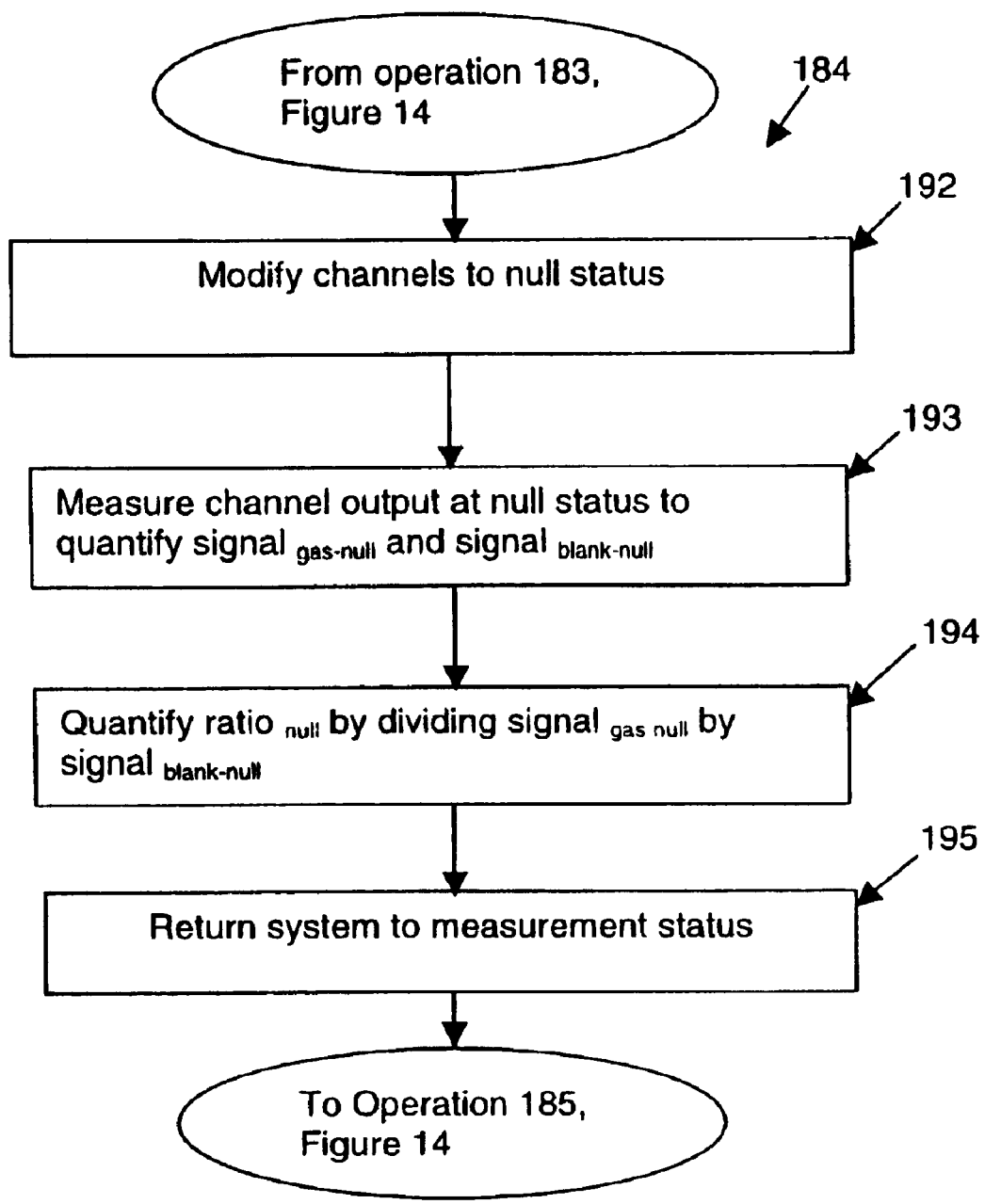
FIGS. 15A and 15B define suboperations of certain operations of the flow chart of FIG. 14.
Figure 15B:
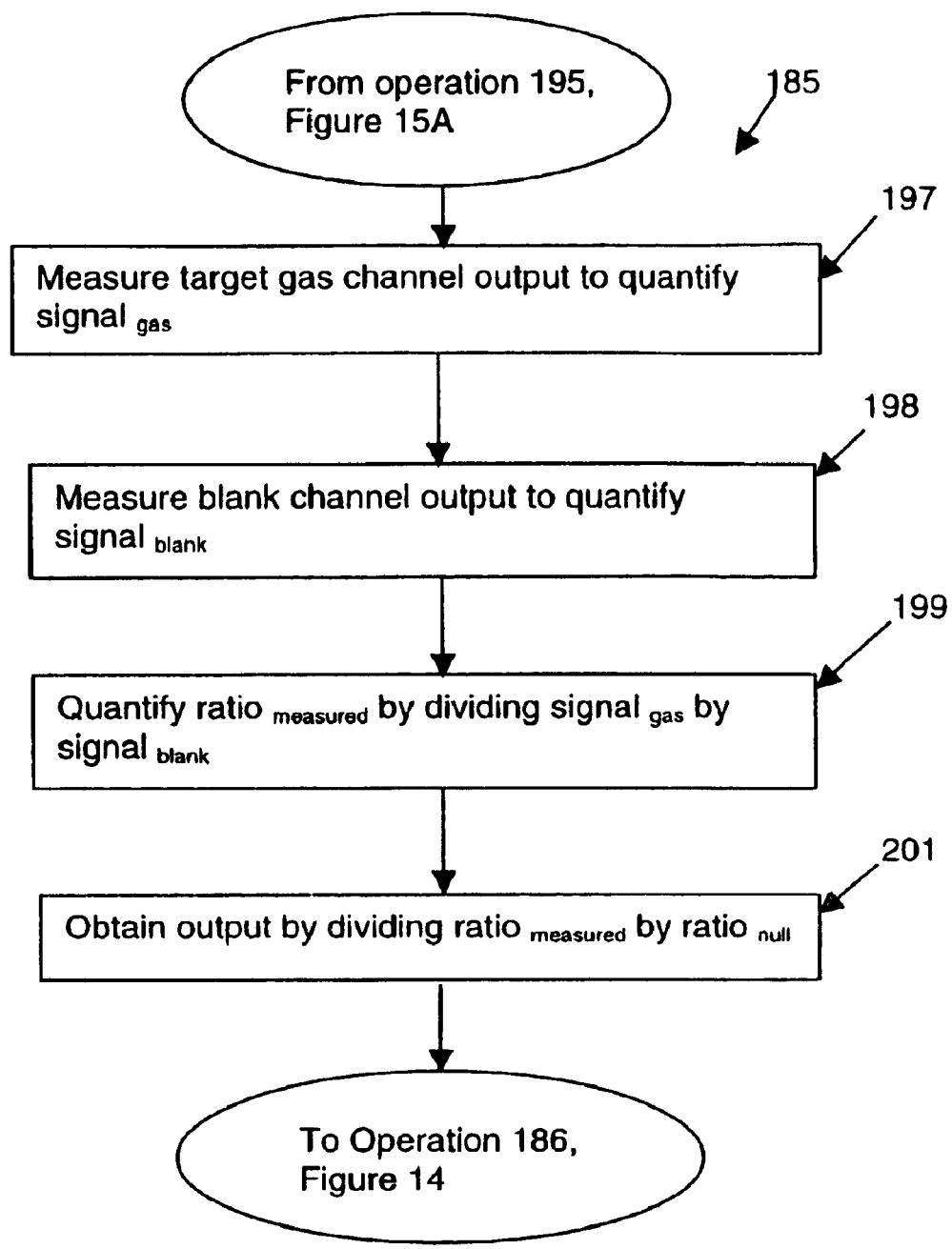

Details of operation 185 of FIG. 14 are shown in FIG. 15B. A suboperation 197 operates the system 50 to measure the amplitude, or value, of the output of the detector 86 (the target gas data 87) through the gas channel 78 to provide a value of $Signal_{gas}$. The method moves to a suboperation 198 in which the amplitude of the output of the detector 82 (the blank channel data 83) measured through the blank channel 76 is obtained to provide a value of $Signal_{blank}$. The method moves to a suboperation 199 in which a value of $Ratio_{measured}$ is obtained by computing the value of a ratio formed by dividing the value of $Signal_{gas}$ by the value of $Signal_{blank}$. The method moves to an operation 201 in which the values obtained in operations 194 and 199 for the respective $Ratio_{null}$ and $Ratio_{measured}$ are used to compute the value of the ratio of $Ratio_{measured}$ to $Ratio_{null}$, i.e., to obtain the value of the above Output. The method then moves to operation 186, FIG. 14.

One advantage of providing $Ratio_{null}$ in the above Equation (9) is the resulting removal of measurement inaccuracies associated with the elements of the system 50. Specifically, $Ratio_{null}$ in Equation (9) removes the effects of alignment variability of the source 61 with respect to the receiver 68, i.e., transmitter-to-receiver alignment variability. Also removed are variabilities of the responsivities of the blank channel detector 82 and the gas channel detector 86, which are in terms of volts of output per optical watt of input. Further removed is variability of channel electronic gain and variability associated with the optical characteristics of the blank channel 76 and of the gas channel 78.

An additional benefit of measuring $Ratio_{null}$ in the field as provided in operations 192 and 193, FIG. 15A (i.e., very close to the time at which $Ratio_{measured}$ is determined) is that such measuring of $Ratio_{null}$ eliminates the effect of broad atmospheric absorbers such as water vapor and aerosols. Such absorbers are broad in the sense that they absorb throughout the entire spectral region of interest established by the IR filter 71. That is, when $Ratio_{null}$ is measured in the field, the Output ($Ratio_{measured}/Ratio_{null}$)−1 is largely independent of atmospheric water vapor concentration, aerosol concentration and potentially other interfering trace gas absorption.

Figure 16:
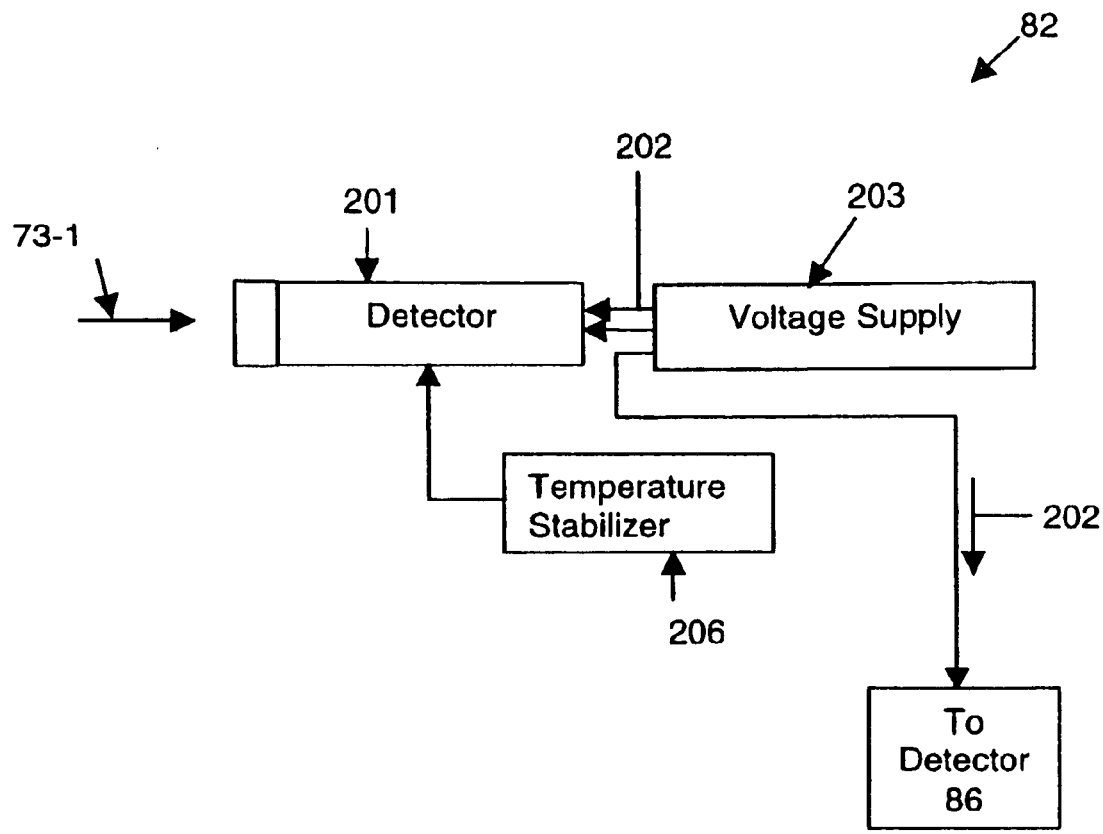
FIG. 16 is a schematic diagram illustrating circuitry for accurately controlling the operation of a light detector.

Referring now to FIG. 16, an embodiment of the system 50 may be configured as follows. The detector 82 for the blank channel 76 is shown in FIG. 16 to illustrate the configuration of both the detectors 82 and 86, which are the same except for the light input. The light beam 73-1 is input to the detector 82 and the light beam 73-2 is input to the detector 86 as shown in FIG. 1A. In FIG. 16 the exemplary detector 82 is shown configured with a respective light detector 201 having a response to the light beam 73-1 that is a function of the light received (i.e., the intensity of the light), of the detector ambient temperature, and of the magnitude of a bias voltage 202 input to the detector 201. A voltage supply 203 is configured to provide each of the detectors 82 and 86 with the common bias voltage 202.

As part of this embodiment of the system 50, a temperature stabilizer 206 is configured for controlling the ambient temperature of each of the detectors 82 and 86. This temperature control is applied during all operations of the system 50 to minimize error due to changes in the sensitivity of the light detectors 201 to the light 58 of the respective beams 73, as measured in amperes of output per watt of optical input. The change in such sensitivity of a typical light detector 201 may be approximately 4% per degree C., and the stabilizer 206 is effective to maintain the detector temperature within a tolerance not to exceed about 0.1 degree C. of a desired detector temperature. The stabilizer 206 limits the temperature-related drift of the detectors 82 and 86 to about ±0.01%, for example.

With the voltage supply 203 and the stabilizer 206 in operation as described, the responses of the two detectors 82 and 86 to the respective light beams 73 are independent of the detector ambient temperature and the bias voltage 202 input to the respective detector 82 and 86, and dependent on the intensity of the respective light beam 73 received by the respective detector 82 and 86.

As described above with respect to FIG. 1A, the source 61 of the system 50 may be configured to direct the light 58 from the transmission location at the near end 62 of the detection path 59 to the far end 63 at the receiver location spaced from the transmission location. In general, such spacing of the ends 62 and 63 may be from about ten feet to about 5300 feet, which in turn provides a similar selected length of the detection path 59. Thus, in the fence line embodiment 50-1 of the system 50 shown in FIG. 1A, for example; this detection path length may be from about 10 feet to about 5300 feet and the separate transmission housing 91 and receiver housing 92 are provided at the respective spaced ends 62 and 63.

Figure 17:
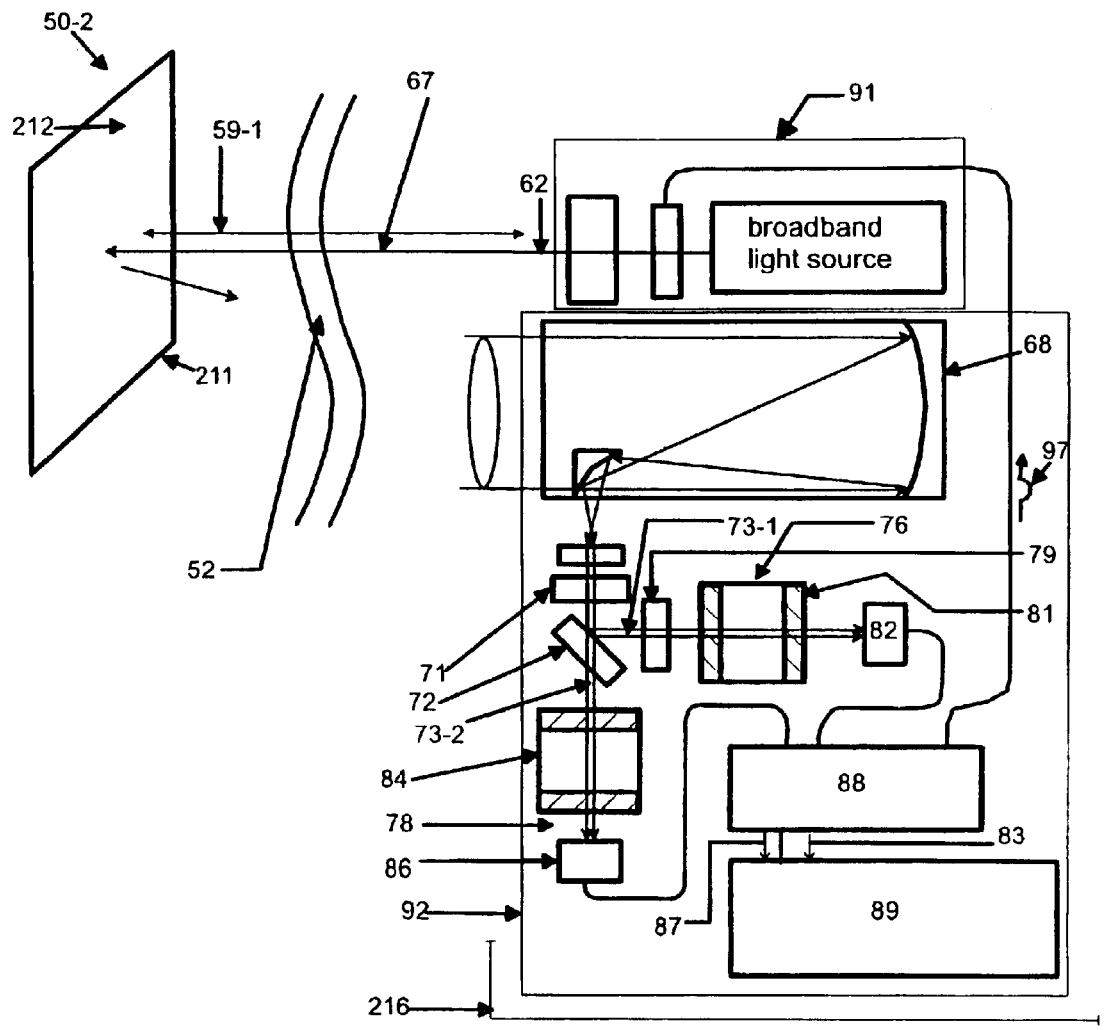
FIG. 17 is a schematic diagram illustrating a vehicle-mounted system for detecting trace amounts of target gases, such as natural gas, remotely along a moderately long detection path in the free atmosphere.

A moderate distance embodiment 50-2 of the system 50 is shown in FIG. 17, in which both the transmission housing 91 and receiver housing 92 are provided at the same near end 62 of the detection path 59. In the embodiment 50-2 the source 61 may be configured to direct the light beam 67 from the transmission location at the near end 62 of the detection path 59 along a first length 59-1 of the detection path 59 to a light beam reflection location 211 at which a reflective surface 212 may be present. Such surface 212 may be a natural surface 212N such as the ground or trees, for example, or a non-natural surface 212A such as that of a wall of a building, for example. The reflective surface 212 reflects the light beam 67 out of the first length 59-1 for return to the receiver 68 at the near end 62 along a second length 59-2 of the detection path 59. The spacing of the near end 62 and the reflection location 211 may be from about fifteen feet to about 1500 feet, which in turn provides another selected length of the detection path 59. In this moderate distance embodiment 50-2 of the system 50 the detection path length (twice the distance from the near end 62 to the reflection location 211) may be as much as about 3000 feet. A typical configuration of the moderate length embodiment 50-2 is to mount both the transmission housing 91 and the receiver housing 92 on a vehicle 216, such as a truck, so that the housings 91 and 92 are provided at the same near end 62. The direction of the detection path 59 is typically away from the vehicle 216, such as away from a road on which the vehicle 216 may be driven, so that any target gas 51 that is away from the vehicle 216 along the detection path 59 to or from the surface 212 may be detected.

Figure 18:
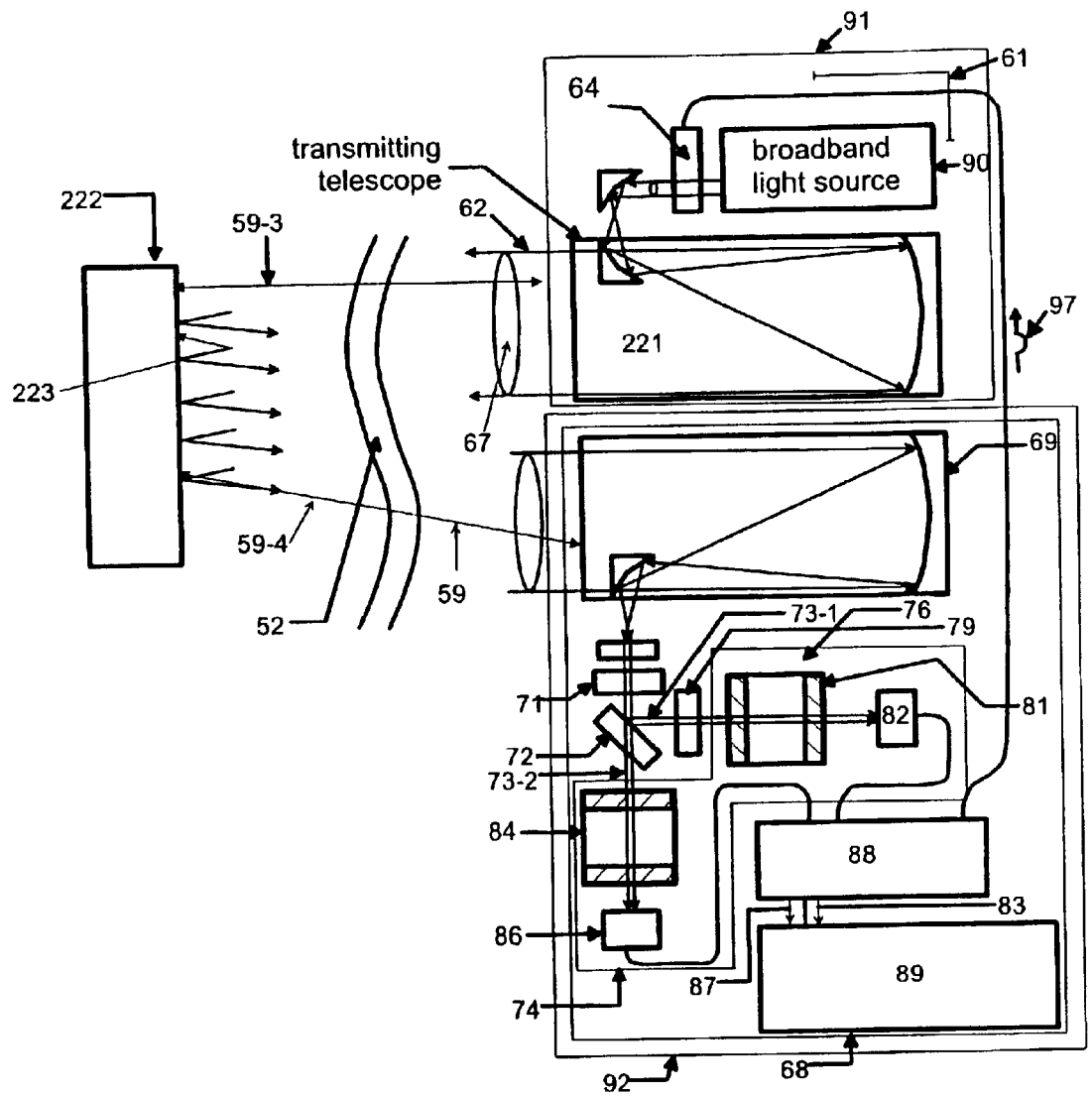
FIG. 18 is a schematic diagram illustrating a stationary system for detecting trace amounts of target gases, such as natural gas, remotely along a long detection path in the free atmosphere.

The embodiment 50-3 of the system 50 is shown in FIG. 18, in which both the transmission housing 91 and receiver housing 92 are provided at the same near end 62 of the detection path 59. In the embodiment 50-3 the source 61 may be configured with a transmitting telescope 221 for long distance direction of the light beam 67 from the transmission location at the one end 62 of the detection path 59 along a second long length 59-3 of the detection path 59 to a light beam reflection location 222 at which a remotely located reflector 223 may be present. Such reflector 223 may be designed to reflect the light beam 67 out of the first length 59-3 for return to the receiving telescope 69 of the receiver 68 at the near end 62 along a fourth length 594 of the detection path 59. The spacing of the near end 62 and the reflection location 222 may be from about 15 to about 2600 feet, which in turn provides another selected length of the detection path 59. In this embodiment 50-3 of the system 50 the detection path length (twice the distance from the near end 62 to the reflection location 222) may be from about thirty feet to about 5300 feet. A typical configuration of the embodiment 50-3 is to mount both the transmission housing 91 and receiver housing 92 fixed to the ground at a known distance from the reflector 223, for example. With this possible path length of up to about a mile, the embodiment 50-3 may be referred to as a long-distance embodiment.

Figure 19:
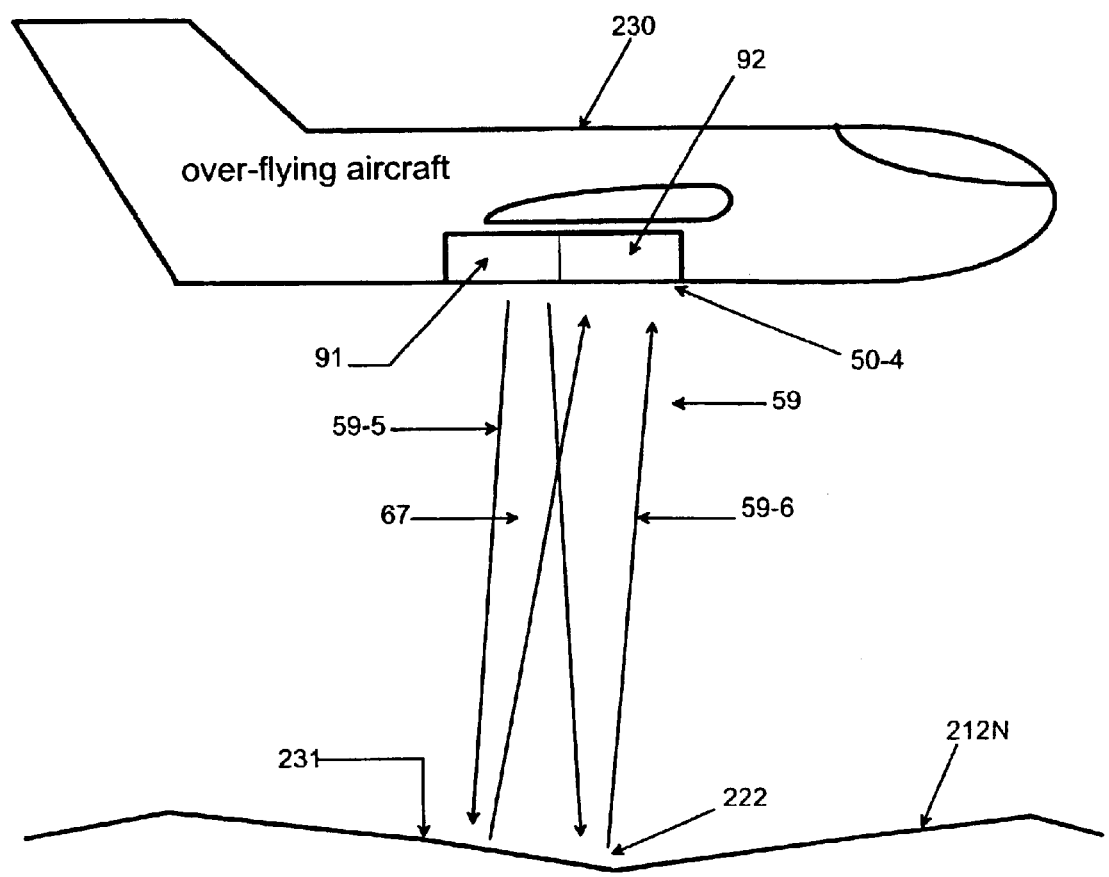
FIG. 19 is a schematic diagram illustrating an airborne system for detecting trace amounts of target gases, such as natural gas, remotely along a long detection path in the free atmosphere.

Another long distance embodiment 50-4 of the system 50 is shown in FIG. 19 as combining the vehicle-mounted aspects of embodiment 50-2 and the long distance detection aspects of the embodiment 50-3. In embodiment 50-4 both the transmission housing 91 and receiver housing 92 are provided on an airborne vehicle, or aircraft, 230, such as an airplane (or helicopter) at the same near end 62 of the detection path 59. Except for the mounting of the housings 91 and 92 on the airborne vehicle 230 rather than on the ground, and the primary use of the ground as a reflective surface 231, embodiments 50-3 and 50-4 are the same. Referring to FIG. 18, the source 61 may be configured with a transmitting telescope 221 for long distance direction of the light beam 67 from the transmission location at the near end 62 of the detection path 59. FIG. 19 shows the beam 67 directed along a second long length 59-5 of the detection path 59 to a light beam reflection location 222 which is typically the ground which acts as the remotely located reflector 231. Such reflector 231 reflects the light beam 67 out of the first length 59-5 for return to the receiver 68 at the near end 62 (FIG. 18) along a long return length 59-6 of the detection path 59. The spacing of the near end 62 and the reflection location 222 may be from about 0 (i.e. when the aircraft 230 is on the ground) to about 2500 feet, which in turn provides another selected length of the detection path 59. In this long distance airborne embodiment 50-4 of the system 50, the detection path length (twice the distance from the near end 62 to the reflection location 222) may be from about 0 feet to about 5000 feet, for example. The direction of the detection path 59 is typically directly downward away from the aircraft 230 toward the ground 231 so that any target gas 51 that is away from the aircraft 230 along the detection path 59 may be detected.

Because of the variable conditions along the long lengths of the detection paths 59 of the embodiments 50-1 through 50-4, and because of the additional reflection conditions which may vary widely as the aircraft 230 flies, each of the systems 50 for these embodiments 50-1 through 50-4 is preferably configured with the above-described features listed below to provide the ability to detect a low minimum detectable concentration of the target gas. The low minimum detectable concentration may vary according to the IR absorption characteristics of the target gas 51. Considering the above-referenced ethane and methane gases as exemplary target gases 51, the system 50 takes advantage of the high depth of IR absorption by ethane to provide a lower minimum detectable concentration of ethane than is provided for methane. Despite the lower depth of IR absorption by methane (than by ethane), the system 50 still provides a minimum detectable concentration of methane (about 50 PPB) that is orders of magnitude lower than that of the above-described prior art instruments.

The listed features include the source 61 provided with the broadband source of light 90, and the modulator 64 at the source 61. The light source 90 may be the arc lamp or a configuration of a thermal emission source (e.g., a plasma glow lamp). The GCR subsystem 74 is provided with the beam splitter 72 so that the split beams 73-1 and 73-2 are processed simultaneously to achieve improved measurement sensitivity and accuracy. The IR filter 71 is optimized to have the optimized central wavelength and the optimized bandpass as described with respect to FIGS. 3A and 3B, which provide substantially increased sensitivity to the particular target gas 51 and substantially increased selectivity of such target gas 51 to avoid erroneous detection of any competitive gas 53 as the target gas 51. The lock-in amplifier 88 is configured for generating the amplified signal 179 proportional to the magnitude of the signal 83 from the blank channel 76 that is at the same frequency as the selectable input 172. The detectors 82 and 86 are provided with the stabilizer 206 and the voltage supply 203 to improve system sensitivity. Also, as described with respect to the most preferred embodiment of FIGS. 14 and 15B, the processing method of obtaining the Output based on Equation (9) using the ($Ratio_{measured}$/$Ratio_{null}$)−1 is used to remove measurement inaccuracies associated with the elements of the system 50, variabilities of the responsivities of the blank channel detector 82 and the gas channel detector 86, as well as the variability of channel electronic gain and variability associated with the optical characteristics of the blank channel 76 and of the gas channel 78. Finally, $Ratio_{null}$ is measured in the field (i.e., very close to the time at which $Ratio_{measured}$ is determined) to eliminate the effect of the broad atmospheric absorbers.

It may be understood that other embodiments of the system 50 may also be configured for use in detecting target gases 51 along a short detection path 59, e.g., of from about 10 feet to about 100 feet in length. Also, the housings 91 and 92 may be stationary and in the fence line configuration shown in FIG. 1A. The embodiment 50-5 is referred to as a short detection path stationary embodiment of the system 50. In view of the reduced length of the detection path 59 and the lack of adverse reflection conditions (that may vary widely, as in the mobile embodiments 50-2 or 50-4), one may not need to include in the short detection path stationary embodiment 50-5 of the system 50 one or more of the last mentioned features.

In more detail, for example, in addition to the factors of atmospheric conditions along the detection path 59, the length of the detection path 59 is a factor related to the detection, determination, and measurement of the target gas 51. The longer the detection path 59, the more the atmospheric conditions along the detection path 59 may absorb, scatter, or reflect the light beam 67 that is directed along the detection path 59, and the more such conditions may temporally vary the light of the beam 67. Thus, the relatively short detection paths 59 described with respect to embodiment 50-5 may be subject to different (less severe) atmospheric conditions than the longer detection paths 59 described with respect to FIGS. 18 and 19, for example. The atmospheric conditions to which the respective embodiments 50-3 and 50-4 of the system 50 of FIGS. 18 and 19 may be exposed render it more necessary to have the features of the system 50 to obtain a minimum detectable concentration of the few PPB (for ethane, for example). Also, surfaces 212N (FIG. 19) of naturally occurring objects, such as the surface of the ground, or the surfaces of buildings or other things made by people (e.g., the reflector 222, FIG. 18), may have differing light reflecting characteristics. Thus, the detection path situation described with respect to FIG. 1A (having no reflective surface 212 along the detection path 59) may present different (less severe) detection, determination, and measurement circumstances due to the respective reflective surfaces 223 and 231 shown in FIGS. 18 and 19. Similarly, the long detection paths 59 shown in FIGS. 18 and 19 may present a combination of circumstances based on both the reflective and the atmospheric conditions, both of which present different (more severe) detection, determination, and measurement circumstances that render it more necessary to have the features of the system 50 to obtain such a minimum detectable concentration of a few PPB.

In view of the foregoing description, it may be understood that the present invention fills these above-described needs by providing the described methods of and system 50 for distinguishing between the target gas 51 and other gases 53 that are normally in the free atmosphere 52 at the same time and in the same place as the target gas 51. The present invention fills such needs for trace gas detection in the natural gas industry by an ability to distinguish between natural gas as a trace gas 51 and other combustible gases 53. Also provided is a more optimal natural gas detector that simultaneously detects both methane and ethane to assure that the detected methane is from a natural gas leak, so as to avoid false natural gas alarms based on the detection, for example, of leaking propane tanks, etc. Further, the method and system 50 substantially increase the detection distance by providing the described detection along the long detection paths 59. Thus, by the present invention the distance from the system 50 to a location of the target gas 51 that is to be detected may be up to about one mile. As a result, mobile platforms, such as the trucks 216 and the aircraft 230, may be used to carry the system 50 during high-speed remote monitoring along long detection paths 59. In addition, the system 50 provides high sensitivity to the target gas 51 independently of atmospheric turbulence and variability, and the above-described undesired influences are removed from the Output of the processor 89 so as to isolate the Output representing the trace gas 51. It may also be understood that in the subsystem 74 the channels 76 and 78 are configured so that the simultaneously measured data 83 and 87 vary from each other based substantially only on the presence of the target gas 51 in the detection path 59 at the time the broadband modulated light 67 is directed into the free atmosphere 52 along the detection path 52.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. Apparatus for detecting at least one specific target gas in the free atmosphere, the apparatus comprising:
   a source of light configured to direct light into a region in which the at least one target gas may be present;
   at least one gas correlation radiometer for responding to light transmitted through the region; and
   a modulator for modulating the light before the light is directed into the region.

2. Apparatus as recited in claim 1, wherein the modulator is configured to modulate the amplitude of the light.

3. Apparatus as recited in claim 1, wherein the modulator is configured to modulate the frequency of the light.

4. Apparatus as recited in claim 1, wherein the light is broadband light and the modulator is configured to output the broadband light having either modulated amplitude or modulated frequency, the modulator causing the light to have source phase and frequency unrelated to the conditions of the free atmosphere; and
   the apparatus further comprising:
      a phase-lock circuit configured to precisely electronically lock to the source phase and frequency of the light transmitted through the region to render the at least one gas correlation radiometer responsive to substantially only the target gas in the free atmosphere and not to the conditions of the free atmosphere other than the presence of the target gas.

5. Apparatus as recited in claim 1, wherein the at least one gas correlation radiometer is configured to respond to light transmitted through the region and having a wavelength within a band in which there is a high degree of dissimilarity in the infrared absorption spectra, the dissimilarity being indicated by wavelengths at which there is high infrared absorption by the target gas and low infrared absorption by the at least one competitive gas.

6. Apparatus as recited in claim 1, wherein the at least one target gas is methane and the at least one gas correlation radiometer is configured to respond to light transmitted through the region and having a wavenumber within a band of about 1000 to about 3500 cm$^{-1}$.

7. Apparatus as recited in claim 1, wherein the at least one target gas is methane and the at least one gas correlation radiometer is configured to respond to light transmitted through the region and having a wavenumber within a band taken from the group consisting of: about 1200 to about 1400 cm$^{-1}$, about 2800 to about 3200 cm$^{-1}$ about 2850 to about 3000 cm$^{-1}$, and about 3000 to about 3200 cm$^{-1}$.

8. Apparatus as recited in claim 1, wherein the at least one target gas is methane and the at least one gas correlation radiometer is configured to respond to light transmitted through the region and having a wavenumber within a band consisting of either about 2850 to about 3000 cm$^{-1}$, or about 3000 to about 3200 cm$^{-1}$.

9. Apparatus as recited in claim 1, wherein the at least one target gas is ethane and the at least one gas correlation radiometer is configured to respond to light transmitted through the region and having a wavenumber within a band of 2970 to 3005 cm$^{-1}$.

10. An apparatus as recited in claim 1, wherein:
the first gas correlation radiometer has a separate background channel and a separate gas channel;
the background channel is configured with a blank cell to output blank channel data that varies according to whether there is target gas in the region; and
the gas channel of the first gas correlation radiometer is configured with a target gas cell to output target gas channel data that is independent of whether there is target gas in the region;
the apparatus further comprising:
a computer programmed to process the data resulting from the detection of the target gas in the region into which the light is transmitted, the data being processed by computing for the respective blank channel data and target gas channel data a value of an output, where the:

output is a function of Ratio$_{measured}$/Ratio$_{null}$;

wherein Ratio$_{measured}$ is the ratio of the target gas channel data to the blank channel data, and
wherein Ratio$_{null}$ is the ratio of the target gas channel data measured without the target gas cell in the target gas channel to the blank channel data measured without the blank cell in the blank channel.

11. Apparatus as recited in claim 1, wherein the at least one target gas are methane and ethane, and wherein:
the source of light is configured to direct light into a region in which the methane and the ethane may be present; and
the at least one gas correlation radiometer comprises two gas correlation radiometers;
a methane detector one of the gas correlation radiometers is configured to respond to light transmitted through the region and having a wavenumber within a band of about 1000 to about 3500 cm$^{-1}$, and an ethane detector one of the gas correlation radiometers is configured to respond to light transmitted through the region and having a wavenumber within a band of about 2970 to about 3005 cm$^{-1}$; and wherein:

the two gas correlation radiometers are configured to respectively simultaneously detect any methane and ethane in the region into which the light is transmitted so that the combined output of the two gas correlation radiometers may indicate the presence in the region of natural gas.

12. An apparatus as recited in claim 11, wherein each of the two gas correlation radiometers has a separate background channel and a separate gas channel, the background channel of the methane gas correlation radiometer is configured with a blank cell to output blank methane data that varies according to whether there is methane in the region, the gas channel of the methane gas correlation radiometer is configured with a methane cell to output methane channel data that is independent of whether there is methane in the region, the background channel of the ethane gas correlation radiometer is configured with a blank cell to output blank ethane data that varies according to whether there is ethane in the region, and the gas channel of the ethane gas correlation radiometer is configured with an ethane cell to output ethane channel data that is independent of whether there is ethane in the region;
the apparatus further comprising:
a computer programmed to process the data resulting from the simultaneous detection of the ethane and methane in the region into which the light is transmitted, the data being processed by computing, for each of the respective ethane channel data and blank ethane data, and the methane channel data and blank methane data, a value of an output, where the:

output for ethane is a function of Ratio$_{measured\ E}$/Ratio$_{null\ E}$;

wherein Ratio$_{measured\ E}$ is the ratio of the ethane channel data to the blank ethane data, and
wherein Ratio$_{null\ E}$ is the ratio of the ethane channel data measured without the ethane cell in the respective gas channel of the respective ethane gas correlation radiometer to the blank ethane data measured without the blank cell in the respective blank channel of the respective ethane gas correlation radiometer; and wherein the output for methane is a function of Ratio$_{measured\ M}$/Ratio$_{null\ M}$;

wherein Ratio$_{measured\ M}$ is the ratio of the methane channel data to the blank methane data, and
wherein Ratio$_{null\ M}$ is the ratio of the methane channel data measured without the methane cell in the respective methane gas channel of the respective methane gas correlation radiometer, to the blank methane data measured without the blank cell in the respective blank channel of the respective methane gas correlation radiometer.

13. An apparatus as recited in claim 1, further comprising:
a first housing configured to contain the source and the modulator at a light transmission location along a detection path in the free atmosphere; and
a second housing configured to contain the at least one gas correlation radiometer at a light receiving location along the detection path in the free atmosphere and spaced from the light transmission location by at least thirty feet.

14. An apparatus as recited in claim 1, further comprising:
a housing configured to support the source, the at least one gas correlation radiometer and the modulator; the housing being configured to be secured to a movable vehicle adapted to move the housing relative to a surface; and wherein the modulator is configured to direct the modulated light into the region against the surface so that a reflected light beam is returned from the surface in the free atmosphere to the at least one gas correlation radiometer in the housing.

15. An apparatus as recited in claim 14, wherein the vehicle is an airborne vehicle and the surface includes the surface of the earth and structures on the surface, and wherein:

the source and the modulator are configured to transmit the modulated light to the surface and any of the structures when the airborne vehicle is at an altitude in a range of from about 10 feet to about 2500 feet; and the at least one gas correlation radiometer is adapted to detect the reflected light beam returned from the surface and any of the structures through the free atmosphere to the at least one gas correlation radiometer in the housing at the altitude in the range of from about ten feet to about 2500 feet.

16. An apparatus as recited in claim 1, further comprising:

a housing configured to contain the light source, the gas correlation radiometer and the modulator at a light transmission location along a detection path in the region of the free atmosphere so that the modulator directs the modulated light into the region along the detection path; and a body spaced from the housing and configured to reflect the modulated light transmitted from the modulator so that a reflected modulated light beam is returned from the body along the detection path in the free atmosphere;

wherein the at least one gas correlation radiometer is configured to receive the reflected modulated light beam.

17. An apparatus as recited in claim 1, further comprising:

a housing configured to contain the light source, the gas correlation radiometer and the modulator at a light transmission location along a detection path in the region of the free atmosphere so that the modulator directs the modulated light into the region along the detection path to a surface having a characteristic of reflecting the modulated light so that a reflected modulated light beam is returned from the surface along the detection path in the free atmosphere;

wherein the at least one gas correlation radiometer is configured to receive the reflected modulated light beam.

18. Apparatus for detecting a specific target gas in the free atmosphere, the apparatus comprising:

a source of light configured to direct light into a region in the free atmosphere in which the specific target gas may be present; and a first gas correlation radiometer having first and second channels for responding to light transmitted through the region, the first gas correlation radiometer also having a first beam splitter configured to separate the light into first and second beams after the light has been transmitted through the region and to direct the first beam into the first channel and to direct the second beam into the second channel;

each of the channels separately responding to the respective light beam for separately generating a signal, the separate signals together indicating whether or not the specific target gas is in the free atmosphere through which the light is transmitted.

19. An apparatus as recited in claim 18, wherein:

each of the channels also simultaneously responds to the respective light beam for separately generating the respective signal.

20. Apparatus as recited in claim 19, wherein the region may contain conditions that absorb or reflect the light and temporally vary the light transmitted through the region to the beam splitter, the apparatus further comprising:

a housing configured to mount the apparatus in a vehicle that is movable relative to the region; and wherein:

the first channel is configured to have the respective separate response to the respective first light beam that is independent of the presence of the target gas in the region and dependent on the presence of gases other than the target gas and dependent on reflections of the light in the region, wherein the second channel is configured to have the respective separate response to the respective second light beam that is dependent on the presence of the target gas in the region and dependent on the presence of gases other than the target gas and dependent on reflections of the light in the region, so that the simultaneously generated signals of the gas correlation radiometer will vary from each other based only on the presence of the target gas in the region at the time of the transmission of the light through the region.

21. Apparatus as recited in claim 19, wherein each of the first and second channels is configured with a respective light detector having a response to the light that is a function of the light received, detector ambient temperature, and a bias voltage input to the detector, the apparatus further comprising:

a voltage supply configured to provide each of the detectors with a common bias voltage; and a temperature stabilizer for controlling the detector ambient temperature of each of the detectors;

wherein different responses of the two detectors to the light are independent of detector ambient temperature and the bias voltage input to the detector and dependent on the light received by the respective detector.

22. Apparatus as recited in claim 19, wherein the temperature stabilizer controls the detector temperature of each of the detectors to within a tolerance not to exceed about 0.1 degree C. of a desired detector temperature.

23. An apparatus as recited in claim 19, wherein the target gas is natural gas consisting primarily of methane and ethane, and wherein the free atmosphere may contain conditions that absorb, scatter or reflect the light and temporally vary the light transmitted through the region to the first beam splitter, the apparatus further comprising:

a second gas correlation radiometer configured to respond to light transmitted through the region and having a wavenumber within a band of about 1000 to about 3500 $cm^{-1}$, the second gas correlation radiometer having third and fourth channels, the second gas correlation radiometer also having a second beam splitter configured to separate the light to be received by the second gas correlation radiometer into third and fourth beams after the light has been transmitted through the region and to direct the third beam into the third channel and to direct the fourth beam into the fourth channel;

a first housing configured to contain the source of light at a light transmission location along a detection path in the region;

a second housing configured to contain the first and second gas correlation radiometers at a light receiving location along the detection path in the region and spaced from the light transmission location by from about ten feet to 3500 feet; and wherein:

the first gas correlation radiometer is configured to respond to light transmitted through the region and having a wavenumber within a band of about 2970 to about 3005 cm$^{-1}$;

the first and second channels of the first gas correlation radiometer are configured to separately and simultaneously with each other respond to the respective first and second light beams for separately and simultaneously generating signals that together indicate whether ethane is in the free atmosphere through which the light is transmitted;

the third and fourth channels of the second gas correlation radiometer are configured to separately and simultaneously with each other and with the first and second channels of the first gas correlation radiometer respond to the respective third and fourth light beams for separately and simultaneously generating signals that together indicate whether methane is in the free atmosphere through which the light is transmitted; and the first and second gas correlation radiometers are configured to simultaneously detect any ethane and methane in the region into which the light is transmitted so that as the conditions absorb, scatter or reflect the light and temporally vary the light transmitted through the region to the beam splitters the combined signals of the first and second gas correlation radiometers may indicate the presence in the region of natural gas.

24. An apparatus as recited in claim 19, further comprising:

a modulator for modulating the light before the light is directed into the region.

25. Apparatus as recited in claim 19, wherein the target gas is natural gas consisting primarily of methane and ethane, and wherein the region contains conditions that absorb, scatter or reflect the light and temporally vary the light transmitted through the region to the beam splitter, the apparatus further comprising:

a housing configured to mount the apparatus in a vehicle that is movable relative to the region so that as the light is transmitted through the region to the beam splitter the conditions through which the light is transmitted from time to time may be different and portions of the region through which the light is transmitted from time to time may or may not contain methane or ethane;

a second gas correlation radiometer in the housing and configured to respond to light transmitted through the region and having a wavenumber within a band of about 1000 to about 3500 cm$^{-1}$; the second gas correlation radiometer having third and fourth channels, the second gas correlation radiometer also having a second beam splitter configured to separate the light to be received by the second gas correlation radiometer into third and fourth beams after the light has been transmitted through the region and to direct the third beam into the third channel and to direct the fourth beam into the fourth channel; and wherein:

the first gas correlation radiometer is configured to respond to light transmitted through the region and having a wavenumber within a band of about 2970 to about 3005 cm$^{-1}$;

the first and second channels of the first gas correlation radiometer are configured to separately and simultaneously with each other respond to the respective first and second light beams for separately and simultaneously generating signals that together indicate whether ethane is in the free atmosphere through which the light is transmitted;

the third and fourth channels of the second gas correlation radiometer are configured to separately and simultaneously with each other and with the first and second channels of the first gas correlation radiometer respond to the respective third and fourth light beams for separately and simultaneously generating signals that together indicate whether methane is in the free atmosphere through which the light is transmitted; and the first and second gas correlation radiometers are configured to simultaneously detect any ethane and methane in the region into which the light is transmitted so that as the vehicle moves relative to the region and the conditions absorb, scatter or reflect the light and temporally vary the light transmitted through the region to the beam splitters the combined signals of the first and second gas correlation radiometers may indicate the presence in the region of natural gas.

26. An apparatus as recited in claim 25, wherein the vehicle is an airborne vehicle and the region may be bounded by the surface of the earth and structures on the surface of the earth, and wherein:

the source is configured to transmit the light along a transmission path to the surface and to the structures when the airborne vehicle is at an altitude in a range of from about 10 feet to about 2500 feet; and the first and second gas correlation radiometers are adapted to detect the reflected light beam returned from the surface and any of the structures in the free atmosphere along a reflection path to the gas correlation radiometers in the housing at the altitude in the range of from about 10 feet to about 2500 feet;

the first and second gas correlation radiometers are adapted to detect natural gas present in either the transmission path or the reflection path.

27. An apparatus as recited in claim 19, further comprising:

a housing configured to contain the light source and the first gas correlation radiometer at a light transmission location along a detection path in the region of the free atmosphere so that the light source directs the light into the region along the detection path; and a body spaced from the housing and configured to reflect the light transmitted from the light source so that a reflected light beam is returned from the body along the detection path in the free atmosphere;

wherein the first gas correlation radiometer is configured to receive the reflected light beam.

28. Apparatus as recited in claim 19 wherein the first gas correlation radiometer is configured to respond to light transmitted through the region and having a wavelength within a band in which there is a high degree of dissimilarity in the infrared absorption spectra, the dissimilarity being indicated by wavelengths at which there is high infrared absorption by the target gas and low infrared absorption by the at least one competitive gas.

29. Apparatus for detecting natural gas in the free atmosphere anywhere along a detection path having a path length of from about ten feet to about fifty three hundred feet, the apparatus comprising:

a source of light configured to direct the light along the detection path within a region of the free atmosphere in which the natural gas may be present anywhere along the detection path;

a beam splitter system configured to divide the light into four separate beams after the light has been transmitted along the detection path through the region, two of the beams being methane detection beams and two of the beams being ethane detection beams;

a methane detection gas correlation radiometer configured to respond to first selected light of the two methane detection beams, the first selected light having a wavenumber within a methane detection band of about 1000 to about 3500 $cm^{-1}$; and an ethane detection gas correlation radiometer configured to respond to second selected light of the two ethane detection beams, the second selected light having a wavenumber within an ethane detection band of about 2970 to about 3005 $cm^{-1}$.

30. An apparatus as recited in claim 29, wherein:
the ethane and methane gas correlation radiometers are configured to simultaneously and separately detect any respective ethane and methane in the region into which the light is transmitted, the simultaneous detection of ethane and methane by the respective gas correlation radiometers indicating the presence of natural gas in the region along the detection path.

31. Apparatus as recited in claim 29, wherein the apparatus distinguishes the natural gas from all other gases in the path; and wherein:
the methane detection gas correlation radiometer is configured with a first channel responsive to one of the respective methane detection beams, the respective response is independent of the presence of the methane in the detection path and dependent on the presence of ethane and the gases other than methane in the detection path;

the ethane detection gas correlation radiometer is configured with a second channel responsive to one of the respective ethane detection beams, the respective response is independent of the presence of the ethane in the path and dependent on the presence of methane and the gases other than ethane in the path;

the methane gas correlation radiometer is configured with a third channel responsive to the other of the respective methane detection beams, the respective response is dependent on the presence of the methane in the path and dependent on the presence of ethane and the gases other than methane in the path;

the ethane gas correlation radiometer is configured with a fourth channel responsive to the other of the ethane detection beams, the respective response is dependent on the presence of the ethane in the path and dependent on the presence of methane and the gases other than ethane in the path;

the responses of the first channel and of the third channel of the methane detection gas correlation radiometer are simultaneous and vary from each other based only on the presence of methane in the detection path at the time of the transmission of the light through the detection path;

the responses of the second channel and of the fourth channel are simultaneous and vary from each other based only on the presence of ethane in the detection path at the time of the transmission of the light through the detection path; and the responses of the respective methane and ethane detection gas correlation radiometers are simultaneous and separate to simultaneously detect any respective methane and ethane in the detection path into which the light is transmitted, the respective simultaneous detection of methane and ethane by the gas correlation radiometers indicating the presence of natural gas in the region somewhere along the detection path.

32. An apparatus as recited in claim 31, the apparatus further comprising:
a computer programmed to process data resulting from the simultaneous detection of the ethane and methane along the detection path along which the light is transmitted, the data being processed by computing, for each of the respective data from the second channel and the fourth channel, and the respective data from the first channel and the third channel, a value of an output, where the:

output for ethane is a function of $Ratio_{measured\ E}/Ratio_{null\ E}$;

wherein $Ratio_{measured\ E}$ is the ratio of the second channel data to the fourth channel data, and wherein $Ratio_{null\ E}$ is the ratio of the second channel data measured without an ethane cell in the respective second channel to the fourth channel data measured without a blank cell in the respective fourth channel; and wherein the output for methane is a function of $Ratio_{measured\ M}/Ratio_{null\ M}$;

wherein $Ratio_{measured\ M}$ is the ratio of the first channel data to the third channel data, and wherein $Ratio_{null\ M}$ is the ratio of the first channel data measured without a methane cell in the respective first channel to the third channel data measured without a blank cell in the respective third channel.

33. Apparatus as recited in claim 29, wherein:
the responses of the methane gas correlation radiometer to the two methane beams are simultaneous and vary from each other based only on the presence of methane in the detection path at the time of the transmission of the light through the detection path;

the responses of ethane gas correlation radiometer to the two ethane beams are simultaneous and vary from each other based only on the presence of ethane in the detection path at the time of the transmission of the light through the detection path; and each of the gas correlation radiometers is configured with two light detectors, each detector having a response to the light that is a function of the light received, detector ambient temperature, and a bias voltage input to the detector; and the apparatus further comprising:
a voltage supply configured to provide each of the two light detectors of each of the two gas correlation radiometers with a common bias voltage; and a temperature stabilizer for controlling the detector ambient temperature of each of the detectors;

wherein different responses of the two light detectors of each of the two gas correlation radiometers to the light are independent of detector ambient temperature and the bias voltage input to the detector and dependent on the light received by the respective detector.

34. Apparatus as recited in claim 29, further comprising:
a first housing configured to contain the source of light at a light transmission location at one end of the detection path; and
a second housing configured to contain the beam splitter system and the respective ethane and methane gas correlation radiometers at a light receiving location at the other end of the detection path.

35. An apparatus as recited in claim 29, further comprising:
a modulator for modulating the light before the light is directed into the region.

36. An apparatus as recited in claim 29, further comprising:
a housing configured to support the source, the beam splitter system, and the ethane and methane detection gas correlation radiometers, the housing being configured to be secured to a movable vehicle adapted to move the housing relative to a surface; and
wherein the source is configured to direct the light along the detection path against the surface so that a reflected light beam is returned from the surface in the free atmosphere to both of the ethane and methane gas correlation radiometers in the housing.

37. An apparatus as recited in claim 36, wherein the vehicle is an airborne vehicle and the surface includes the surface of the earth and structures on the surface, and wherein:
the source is configured to transmit the light to the surface and any of the structures when the airborne vehicle is at an altitude in a range of from about 10 feet to about 2500 feet; and
both of the ethane and methane gas correlation radiometers are adapted to detect the reflected light beam returned from the surface and any of the structures through the free atmosphere to both of the gas correlation radiometers in the housing at the altitude in the range of from about 10 feet to about 2500 feet.

38. An apparatus as recited in claim 29, further comprising:
a housing configured to contain the light source, the beam splitter system, and both of the gas correlation radiometers at a light transmission location so that the light source directs the light into the region along a detection path; and
a body spaced from the housing and configured to reflect the light transmitted from the housing so that a reflected light beam is returned from the body along the detection path in the free atmosphere;
wherein both of the gas correlation radiometers are configured to receive the reflected light beam.

39. An apparatus as recited in claim 29, further comprising:
a housing configured to mount the light source, the beam splitter system, and both of the gas correlation radiometers at a light transmission location along a detection path in the region of the free atmosphere so that the light source directs the light to a surface adapted to reflect the light and return a reflected light beam along the detection path to both of the gas correlation radiometers;
wherein the gas correlation radiometers are configured to receive the reflected light beam for detection of natural gas anywhere along the detection path.

40. Apparatus as recited in claim 29, wherein the detection path may contain conditions that absorb, scatter or reflect the light and temporally vary the light transmitted to the beam splitter system, the apparatus further comprising:
a housing configured to contain the source of light and the ethane and methane gas correlation radiometers; and
a mount configured to secure the housing to a movable vehicle adapted to move the housing relative to a surface; and
wherein the source is configured to direct the light into the region against the surface so that a reflected light beam is returned from the surface in the free atmosphere along the detection path to the ethane and methane gas correlation radiometers in the housing.

41. An apparatus as recited in claim 40, wherein the movable vehicle is an airborne vehicle and the surface includes the surface of the earth and structures on the surface, and wherein:
the source is configured to transmit the modulated light to the surface and any of the structures when the airborne vehicle is at an altitude in a range of from about 10 feet to about 2500 feet; and
the ethane and methane gas correlation radiometers are adapted to detect the reflected light beam returned from the surface and any of the structures along the detection path through the free atmosphere to the respective ethane and methane gas correlation radiometers in the housing at the altitude in the range of from about 10 feet to about 2500 feet.

42. An apparatus as recited in claim 29, further comprising:
a housing configured to contain the light source, the beam splitter system, and the ethane and methane detection gas correlation radiometers at a light transmission location at one end of the detection path in the region of the free atmosphere so that the light source directs the light into the region along the detection path; and
a body spaced from the housing and configured to reflect the light transmitted from the source so that a reflected light beam is returned from the body along the detection path in the free atmosphere;
wherein each of the ethane and methane detection gas correlation radiometers is configured to receive the reflected light beam.

43. An apparatus as recited in claim 29, further comprising:
a modulator for modulating the light before the light is directed into the region, the modulator causing the first and second light of the four separate beams to have source phase and frequency unrelated to the conditions of the free atmosphere; and
a phase-lock circuit for each of the gas correlation radiometers configured to precisely electronically lock to the source phase and frequency of the four separate beams.

44. Apparatus for detecting a specific target gas in the free atmosphere, the apparatus comprising:
a source configured to direct light into a region of the free atmosphere in which the target gas may be present and in which there is likely to be at least one competitive other gas the presence of which may interfere with detection of the specific target gas; and
a gas correlation radiometer configured to respond to light from the source transmitted through the region, the gas correlation radiometer having an infrared filter configured with a band pass having a limited range, the limited range being selected according to the following operations:

identifying a first absorption spectrum of the target gas corresponding to selected gas concentration, temperature, pressure, and path length;

identifying a second absorption spectrum of the at least one other competitive gas, the second absorption spectrum corresponding to the selected gas concentration, temperature, pressure, and path length; and selecting as the limited range a range of light wavelengths corresponding to both strong infrared absorption by the target gas and to weak infrared absorption by the competitive other gas.

45. Apparatus for detecting a specific target gas in the free atmosphere, the apparatus comprising:

a source configured to direct light into a region of the free atmosphere in which the target gas may be present and in which there is likely to be at least one competitive other gas the presence of which may interfere with detection of the specific target gas; and a gas correlation radiometer configured to respond to light from the source transmitted through the region, the gas correlation radiometer having an infrared filter configured with a band pass having a limited range, the limited range being selected according to the following operations:

identifying a first absorption spectrum of the target gas corresponding to selected gas concentration, temperature, pressure, and path length;

identifying a second absorption spectrum of the at least one other competitive gas, the second absorption spectrum corresponding to the selected gas concentration, temperature, pressure, and path length; and comparing the first absorption spectrum to the second absorption spectrum to identify one wavelength range in which there is a high degree of dissimilarity in the infrared absorption spectra, the dissimilarity being indicated by wavelengths at which there is high infrared absorption by the target gas and low infrared absorption by the at least one competitive gas.

46. An apparatus as recited in claim 45, the operations for the selection of the limited range further comprising:

selecting the identified wavelength range as the limited range of the band pass of the infrared filter.

47. Apparatus for detecting a reduced minimum concentration of a particular target gas anywhere along a detection path having a given length in the free atmosphere, the particular target gas having a rich infrared absorption spectrum, the apparatus comprising:

a source configured to direct light into the free atmosphere along the detection path, the given length of the detection path being from a first end to a second end and having a value in a range of from about 100 feet to about one mile, the light being broadband light within a wavelength band of from about 0.2 micrometers to about 100 micrometers;

a crystal controller oscillator configured to modulate the light with a frequency accuracy and control of about 1 part in $10^6$ before the light is directed into the free atmosphere along the detection path;

an infrared filter configured to receive the broadband modulated light, the filter being configured with a band pass that is optimal for detecting the particular target gas, the optimal band pass including infrared absorption features of the particular target gas to be detected and a suitable transmission region produced by all common gaseous constituents of the free atmosphere other than the particular target gas, within the band pass there being a relatively small degree of spectral overlap between the infrared absorption features of the target gas and that of the atmospheric spectrum;

a beam splitter configured to receive the light from the source and to simultaneously direct the light into first and second separate light paths;

a dual channel gas correlation radiometer having a first channel configured to receive light in the first separate light path and to provide an infrared absorption spectrum corresponding to the particular target gas, the first channel being configured with optical elements which have an effect on spectral features of the light transmitted through the first channel, the radiometer having a second channel configured to receive light in the second separate light path and to transmit the modulated light without substantial infrared absorption of the particular target gas, the second channel being configured with optical elements which have an effect on spectral features of the light transmitted through the second channel;

a separate detector for light transmitted through each of the respective first channel and second channel, the separate detectors simultaneously providing a respective measured first signal and a respective measured second signal based on the intensity and wavelength of the respective light transmitted through the respective first channel and second channel;

a lock-in amplifier configured to receive the electronic signals produced by the first and second channel detectors and to isolate the modulated broadband light signal from any ambient steady-state thermal emission background that may be present along the detection path;

a stabilization system configured to stabilize the temperature of the first channel detector and of the second channel detector and to stabilize a bias voltage supplied to the first channel detector and to the second channel detector; and a processor responsive to the separate simultaneous measured first and second signals, the processor being programmed for determining the average concentration of the trace amount of the target gas along the detection path in the free atmosphere through which the modulated broadband light was transmitted, the programming including instructions for computing a value of a null ratio having a denominator based on the output of the second channel detector in response to the light in the second separate path that bypasses the optical elements of the second channel, the null ratio having a numerator based on the output of the first channel detector in response to the light in the first separate path that bypasses the optical elements of the first channel, the processor being programmed to compute the value of the average concentration of the trace amount of the target gas along the detection path in the free atmosphere as a function of the value of a computational ratio, the computational ratio having a numerator formed by the ratio of the value of the measured first signal to the value of the measured second signal, the computational ratio having a denominator formed by the null ratio.

48. Apparatus as recited in claim 47, wherein the detection path may contain conditions that absorb, scatter or reflect the light and temporally vary the light transmitted through the region to the beam splitter, the apparatus further comprising:

a housing configured to mount the apparatus on a vehicle that is movable relative to the detection path so that as the light is transmitted through the detection path to the infrared filter the conditions through which the light is transmitted from time to time may be different and portions of the detection path along which the light is transmitted from time to time may or may not contain the particular target gas; and wherein:

the first channel is also configured to have a response to the light in the first separate light path dependent on the presence in the detection path of gases other than the particular target gas and dependent on reflections of the light in the detection path;

the second channel is also configured to have a response to the light in the second separate light path dependent on the presence of the particular target gas in the detection path and dependent on the presence in the detection path of gases other than the particular target gas and dependent on reflections of the light in the region, so that the simultaneous measured first and second signals vary from each other based substantially only on the presence of the particular target gas in the detection path at the time the broadband modulated light is directed into the free atmosphere along the detection path.

49. Apparatus as recited in claim 47, wherein each of the separate detectors is configured with a respective response to light that is a function of the light received, detector ambient temperature, and a bias voltage input to the detector, the apparatus further comprising:

a voltage supply configured to provide each of the detectors with a common bias voltage; and a temperature stabilizer for controlling the detector ambient temperature of each of the detectors;

wherein different responses of the separate detectors to the light are independent of detector ambient temperature and the bias voltage input to the detector and dependent on the light received by the respective detector.

50. Apparatus as recited in claim 47, wherein the temperature stabilizer controls the detector ambient temperature of each of the detectors to within a tolerance not to exceed about 0.1 degree C. of a desired ambient detector temperature.

51. An apparatus as recited in claim 47, wherein the target gas is natural gas consisting primarily of methane and ethane, and wherein the free atmosphere may contain conditions that absorb, scatter or reflect the light and temporally vary the light transmitted through the region to the beam splitter, and wherein the beam splitter is further configured to direct the modulated broadband light into third and fourth separate light paths simultaneously with the direction of the first and second separate light paths, the apparatus further comprising:

a second dual channel gas correlation radiometer configured to respond to light transmitted along the detection path and having a wavenumber within a band of about 1000 to about 3500 $cm^{-1}$, the second gas correlation radiometer having third and fourth channels configured to respectively receive the light in the third and fourth separate light paths, the third channel being configured to receive light in the third separate light path and transmit light that is independent of whether there is methane in the region, the fourth channel being configured to receive light in the fourth separate path and output light that varies according to whether there is methane in the region;

a first housing configured to contain the source of light and the oscillator at the first end of the detection path;

a second housing configured to contain the beam splitter, the amplifier, the infrared filter, both of the gas correlation radiometers, the detectors, the stabilization system, and the processor at the second end of the detection path; and wherein:

the gas correlation radiometer having the first and second channels is configured to respond to light transmitted along the detection path and having a wavenumber within a band of about 2970 to about 3005 $cm^{-1}$;

the separate detectors for the respective first and second channels are configured to separately and simultaneously with each other respond to the light in the respective first and second light paths for separately and simultaneously providing the respective first and second measured signals that together indicate whether ethane is somewhere in the detection path through which the light is transmitted;

the apparatus further comprising:

a separate detector configured for light transmitted through each of the respective third and fourth channels of the second gas correlation radiometer and configured to separately and simultaneously with each other and with the detectors for the first and second channels respond to light in the respective third and fourth light paths for separately and simultaneously providing respective third and fourth measured signals that together indicate whether methane is in the free atmosphere through which the light is transmitted; and wherein:

the gas correlation radiometers are configured to simultaneously detect any ethane and methane in the detection path into which the light is transmitted so that as the conditions absorb, scatter or reflect the light and temporally vary the light transmitted through the detection path to the beam splitter the combined first, second, third, and fourth measured signals provided by the detectors may indicate the presence somewhere along the detection path of natural gas.

52. An apparatus as recited in claim 47, wherein:

each of the separate detectors is configured with a respective response to light that is a function of the light received, detector ambient temperature, and a bias voltage input to the detector, the apparatus further comprising:

a voltage supply configured to provide each of the detectors with a common bias voltage; and a temperature stabilizer for controlling the detector ambient temperature of each of the detectors; and wherein different responses of the separate detectors to the light are independent of detector ambient temperature and the bias voltage input to the detector and dependent on the light received by the respective detector.

53. An apparatus as recited in claim 47, wherein the target gas is natural gas consisting primarily of methane and ethane, and wherein the detection path may contain conditions that absorb, scatter or reflect the light and temporally vary the light transmitted through the detection path to the infrared filter, and wherein the beam splitter is further configured to direct the light into third and fourth separate light paths simultaneously with the direction of the first and second separate light paths, the apparatus further comprising:

a housing configured to mount the apparatus on a vehicle that is movable relative to the detection path so that as the light is transmitted through the detection path to the infrared filter the conditions through which the light is transmitted from time to time may be different and portions of detection path through which the light is transmitted from time to time may or may not contain methane or ethane;

a second gas correlation radiometer in the housing and configured to respond to light transmitted along the detection path and having a wavenumber within a band of about 1000 to about 3500 cm$^{-1}$, the second gas correlation radiometer having third and fourth channels configured to respectively receive the light in the third and fourth separate light paths, the third channel being configured to receive light in the third separate light path and transmit light that is independent of whether there is methane in the region, the fourth channel being configured to receive light in the fourth separate path and transmit light that varies according to whether there is methane in the region; and wherein:

the first-recited gas correlation radiometer is configured to respond to light transmitted through the region and having a wavenumber within a band of about 2970 to about 3005 cm$^{-1}$ and transmit light that is independent of whether there is methane in the region, the fourth channel being configured to receive light in the fourth separate path and output light that varies according to whether there is methane in the region;

the separate detectors for the respective first and second channels are configured to separately and simultaneously with each other respond to the light in the respective first and second light paths for separately and simultaneously providing the respective first and second measured signals that together indicate whether ethane is somewhere in the detection path through which the light is transmitted;

the apparatus further comprising:

a separate detector configured for light transmitted through each of the respective third and fourth channels of the second gas correlation radiometer and configured to separately and simultaneously with each other respond to light in the respective third and fourth light paths for separately and simultaneously with each other providing respective third and fourth measured signals that together indicate whether methane is in the free atmosphere through which the light is transmitted; and wherein:

the detectors and the gas correlation radiometers are configured to detect any ethane and methane in the detection path into which the light is transmitted so that as the conditions absorb, scatter or reflect the light and temporally vary the light transmitted through the detection path to the beam splitter the combined first, second, third, and fourth measured signals provided by the detectors may indicate the presence of natural gas somewhere along the detection path.

54. An apparatus as recited in claim 53, wherein the detectors and the gas correlation radiometers are configured to simultaneously detect any ethane and methane in the detection path into which the light is transmitted.

55. An apparatus as recited in claim 53, wherein the vehicle is an airborne vehicle and an intermediate point of the detection path between the first end and the second end of the detection path may be defined by the surface of the earth and structures on the surface of the earth, and wherein:

the source is configured to transmit the light along the detection path to the surface and to the structures when the airborne vehicle is at an altitude in a range of from about 10 feet to about 2500 feet and to cause the light to be reflected from the surface and any of the structures along a reflection path;

the first-recited and second gas correlation radiometers are adapted to detect the reflected light returned from the surface and any of the structures along the reflection path to the housing at the altitude in the range of from about 10 feet to about 2500 feet; and the detectors and the first and second gas correlation radiometers are configured to detect natural gas present in either the detection path or the reflection path.

56. An apparatus as recited in claim 47, wherein the first channel of the dual gas correlation radiometer is configured with a material having the infrared absorption spectrum corresponding to the particular target gas so that the detector for the first channel outputs the measured first signal having a value that is independent of whether or not the particular target gas is anywhere along the detection path, and wherein the second channel of the dual gas correlation radiometer is configured with a blank cell to transmit the light without substantial infrared absorption of the particular target gas so that the detector for the second channel outputs the measured second signal having a value that is a function of whether or not there is target gas anywhere along the detection path; the apparatus further comprising:

a computer programmed to process the measured first and second signals, the programming being to compute, for the respective first and second signals, a value of an output representing the trace amount of the target gas anywhere along the detection path, where the:

output is a function of Ratio$_{measured}$/Ratio$_{null}$;

wherein Ratio$_{measured}$ is the ratio of the first measured signal to the second measured signal, and wherein Ratio$_{null}$ is the ratio of the first measured signal output by the detector corresponding to the first channel without the material in the first channel to the second measured signal output by the detector corresponding to the second channel without the blank cell in the second channel.

57. An apparatus as recited in claim 47, further comprising:

a housing configured to contain the apparatus at a light transmission location at the first end of the detection path so that the light source directs the light along the detection path; and a body spaced from the housing and configured to reflect the light transmitted from the light source so that a reflected light beam is returned from the body along the detection path in the free atmosphere to the housing for reception by the infrared filter.

58. A method for detecting the presence of a trace amount of a specific target gas within the free atmosphere, the method comprising the operations of:

transmitting broadband light into the free atmosphere along a detection path in which the specific target gas may be present;

at an end of the detection path splitting the broadband light into two separate and simultaneous portions of the broadband light;

providing a dual channel gas correlation radiometer, a target gas channel of the dual channels being a first channel configured with a target gas absorption spectrum, a blank channel one of the dual channels being a second channel configured to receive light from the detection path and output light that varies according to whether there is target gas in the region; and configuring the first channel and the second channel to simultaneously detect the separate respective portions of the broadband light after the broadband light has been transmitted through the detection path.

59. A method as recited in claim 58, further comprising the operations of:

before the configuring operation, performing the following method to optimize the simultaneous detection of the portions of the light by the gas correlation radiometer to the trace amount of the target gas present in the free atmosphere along the detection path to the gas correlation radiometer, the following method being a method of optimizing a response of a gas correlation radiometer to a trace amount of a target gas present in the free atmosphere along a detection path to the gas correlation radiometer, wherein the detection path may also contain at least one competitive other gas the presence of which in the free atmosphere may interfere with detection of the trace amount of the target gas, the method comprising the operations of:

identifying a spectral region of a first absorption spectrum of the target gas, the spectrum corresponding to selected parameters of target gas concentration, target gas temperature, target gas pressure, and path length through the target gas, the spectral region having a plurality of high absorption characteristics and low absorption characteristics;

for the spectral region, providing a second absorption spectrum of the at least one other competitive gas, the second absorption spectrum corresponding to the selected parameters and including non-absorbing regions corresponding to the low-absorption characteristics of the first absorption spectrum;

determining a set of similarity data as a function of overlap regions within the spectral region, the overlap regions being for each of the at least one other competitive gas and the target gas and being those regions within the spectral region in which the respective absorption spectra of both the target gas and the at least one other competitive gas have absorption characteristics, the set of similarity data including a plurality of data items within each of a plurality of bandwidths, one of the data items corresponding to a center wavelength within each bandwidth;

determining a set of contrast data as a function of non-overlap regions within the spectral region, the non-overlap regions being for each of the at least one other competitive gas and the target gas and being those regions within the spectral region in which the first absorption spectrum has high absorption characteristics but the second absorption spectrum has low absorption characteristics, the set of contrast data including a plurality of data items within each of a plurality of bandwidths, one of the data items corresponding to a center wavelength within each bandwidth;

preparing a graph corresponding to each of the bandwidths, each graph being a plot of the data points, each data point having an ordinate axis value based on a contrast data item minus a similarity data item, each data point having an abscissa axis value based on one of the center wavelengths;

from one of the prepared graphs, selecting as a center wavelength of an infrared filter for use with the gas correlation radiometer the center wavelength corresponding to the highest value of the contrast data item minus the similarity data item of all of the graphs;

selecting as the bandwidth of the infrared filter the bandwidth corresponding to the graph having the highest value of the contrast data item minus the similarity data item of all of the graphs; and providing the infrared filter having the selected center wavelength and bandwidth for use with the gas correlation radiometer to filter light transmitted through the free atmosphere to the gas correlation radiometer.

60. A method as recited in claim 58, wherein the first-mentioned providing operation configures each of the first and second channels with a respective light detector having a response to the light that is a function of the light received, detector ambient temperature, and a bias voltage input to the detector, the method further comprising the operations of:

applying a common bias voltage to each of the detectors; and controlling the detector temperature of each of the detectors;

wherein different responses of the two detectors to the light are independent of detector ambient temperature and independent of the bias voltage input to the detector and dependent on the light received by the respective detector.

61. A method as recited in claim 60, wherein the controlling operation controls the detector temperature of each of the detectors to within about 0.1 degree C. of a desired detector temperature.

62. A method as recited in claim 58, wherein:

the operation of providing the dual channel gas correlation radiometer is for detection of ethane as the target gas, the first channel being configured with an ethane absorption spectrum, the blank channel one of the dual channels being the second channel configured with the pathway that is optically inert with respect to ethane; and the method further comprising:

providing a second dual channel gas correlation radiometer for detection of methane as the target gas simultaneously with the detection of the ethane, the second dual channel gas correlation radiometer having a third channel corresponding to the first channel and being configured with a methane absorption spectrum, the second dual channel gas correlation radiometer having a fourth channel corresponding to the blank channel and being configured with the pathway that is optically inert with respect to methane; and programming a computer to process data resulting from the simultaneous detection of the target gases ethane and methane along the detection path along which the light is transmitted, the processing by the programmed computer being, for each of the first, second, third, and fourth channels of the respective dual channel gas correlation radiometers, a value of an output, where the:

output for ethane is a function of $\text{Ratio}_{measured\ E}/\text{Ratio}_{null\ E}$;

wherein $\text{Ratio}_{measured\ E}$ is the ratio of a third channel detection output to a fourth channel detection output, and wherein Ratio$_{null}$ is the ratio of third channel detection output measured without an ethane cell in the respective third channel to fourth channel detection output measured without an optically inert pathway in the respective fourth channel; and wherein the output for methane is a function of Ratio$_{measured\ M}$/Ratio$_{null\ M}$;

wherein Ratio$_{measured\ M}$ is the ratio of a first channel detection output to a second channel detection output, and wherein Ratio$_{null\ M}$ is the ratio of the first channel detection output measured without a methane cell in the respective first channel to the second channel detection output measured without an optically inert pathway in the respective second channel.

63. A method as recited in claim 58, further comprising the operation of:

modulating the broadband light and then transmitting the modulated light into the free atmosphere.

* * * * *